US010355213B2

(12) United States Patent
Facchetti et al.

(10) Patent No.: US 10,355,213 B2
(45) Date of Patent: Jul. 16, 2019

(54) DITHIOPHENETHIADIAZOLE SEMICONDUCTORS AND RELATED DEVICES

(71) Applicants: Flexterra, Inc., Skokie, IL (US); RAYNERGY TEK INC., Hsinchu (TW)

(72) Inventors: Antonio Facchetti, Chicago, IL (US); Zhihua Chen, Skokie, IL (US); Chuang-Yi Liao, Hsinchu (TW)

(73) Assignees: FLEXTERRA, INC., Skokie, IL (US); RAYNERGY TEK INC., Hsinchu (TW)

( * ) Notice: Subject to any disclaimer, the term of this patent is extended or adjusted under 35 U.S.C. 154(b) by 0 days.

(21) Appl. No.: 15/772,923

(22) PCT Filed: Jan. 9, 2017

(86) PCT No.: PCT/US2017/012697
§ 371 (c)(1),
(2) Date: May 2, 2018

(87) PCT Pub. No.: WO2017/120572
PCT Pub. Date: Jul. 13, 2017

(65) Prior Publication Data
US 2018/0323375 A1    Nov. 8, 2018

Related U.S. Application Data

(60) Provisional application No. 62/276,844, filed on Jan. 9, 2016.

(51) Int. Cl.
*H01L 51/00* (2006.01)
*C08G 61/12* (2006.01)
(Continued)

(52) U.S. Cl.
CPC ........ *H01L 51/0036* (2013.01); *C07D 513/14* (2013.01); *C08G 61/12* (2013.01); *C08G 61/123* (2013.01); *C08G 61/126* (2013.01); *H01L 51/0071* (2013.01); *H01L 51/0074* (2013.01); *C08G 2261/146* (2013.01); *C08G 2261/149* (2013.01); *C08G 2261/1412* (2013.01); *C08G 2261/1424* (2013.01); *C08G 2261/164* (2013.01); *C08G 2261/226* (2013.01);
(Continued)

(58) Field of Classification Search
CPC ...... C08G 2261/3223; C08G 2261/126; C08G 2261/124; C08G 2261/95; C08G 2261/91; C08G 61/12; C08G 61/123; C08G 61/126; C07D 417/14; C07D 513/14; H01L 51/36; H01L 51/71; H01L 51/74; C08K 3/045; C08L 65/00
See application file for complete search history.

(56) References Cited

U.S. PATENT DOCUMENTS

2016/0149138 A1* 5/2016 Facchetti ............ H01L 51/0036
136/263

* cited by examiner

*Primary Examiner* — Shane Fang
(74) *Attorney, Agent, or Firm* — WPAT, PC

(57) ABSTRACT

The present invention relates to new semiconducting compounds having at least one optionally substituted dithieno [1,2,3]thiadiazole moiety. The compounds disclosed herein can exhibit high carrier mobility and/or efficient light absorption/emission characteristics, and can possess certain processing advantages such as solution-processability and/ or good stability at ambient conditions.

23 Claims, 2 Drawing Sheets

(51) Int. Cl.
*C07D 513/14* (2006.01)
*H01L 51/05* (2006.01)
*C08K 3/04* (2006.01)

(52) U.S. Cl.
CPC ............. *C08G 2261/3223* (2013.01); *C08G 2261/3225* (2013.01); *C08G 2261/3243* (2013.01); *C08G 2261/3246* (2013.01); *C08G 2261/344* (2013.01); *C08G 2261/364* (2013.01); *C08G 2261/414* (2013.01); *C08G 2261/91* (2013.01); *C08G 2261/92* (2013.01); *C08K 3/045* (2017.05); *H01L 51/0525* (2013.01); *H01L 51/0558* (2013.01); *Y02E 10/549* (2013.01)

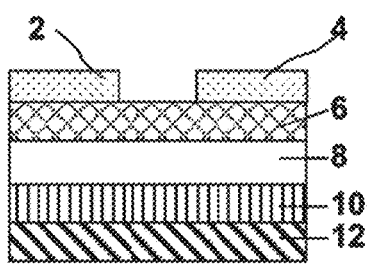
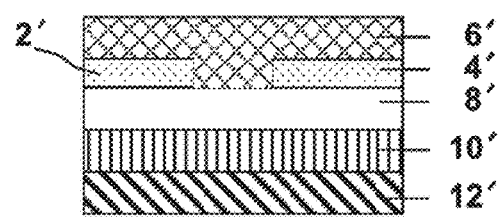
Figure 1a     Figure 1b
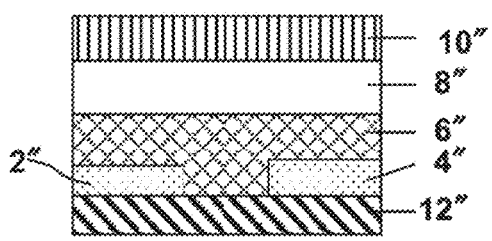
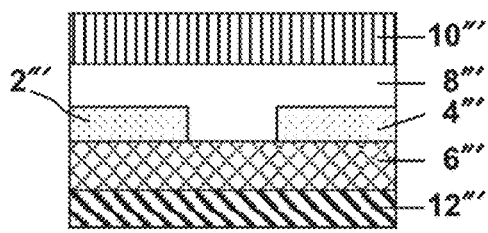
Figure 1c     Figure 1d

DITHIOPHENETHIADIAZOLE SEMICONDUCTORS AND RELATED DEVICES

CROSS REFERENCE TO RELATED APPLICATIONS

This application claims priority to and the benefit of U.S. Provisional Patent Application Ser. No. 62/276,844, filed on Jan. 9, 2016, the disclosure of which is incorporated by reference in its entirety.

BACKGROUND

Flexible and printed electronics is a revolutionary new concept for fabricating optoelectronic devices using high-throughput, inexpensive solution processes (e.g., printing methodologies) on flexible plastic foils, which contrasts sharply with the highly specialized and expensive facilities and equipment required for silicon fabrication. By using the appropriate materials, these technologies could enable inexpensive, lightweight, flexible, optically transparent, and unbreakable components for displays, cell phones, medical diagnostics, RFID tags, and solar modules which can then be integrated with textiles, printed batteries, solar cells, and aircraft and satellite structures. The enabling material component of all these technologies (among other essential materials) is the semiconductor where charge transport, light absorption, and/or light generation occur. To broaden device functionalities and applications, two types of semiconductors are required: p-type (hole-transporting) and n-type (electron-transporting). The use and combination of these two types of semiconductors enables the fabrication of elementary electronic building blocks for driving displays, harvesting light, generating light, carrying out logic operations, and sensor functions.

Several p- and n-channel molecular semiconductors have achieved acceptable device performance and stability. For example, OTFTs based on acenes and oligothiophenes (p-channel) and perylenes (n-channel) exhibit carrier mobilities ($\mu$'s)>1 $cm^2$/Vs in ambient conditions. However, molecular semiconductors typically are less easily processable via printing methodologies than polymeric semiconductors due to solution viscosity requirements.

Accordingly, the art desires new semiconducting compounds, particularly those having good stability, processing properties, and/or charge transport characteristics in ambient conditions.

SUMMARY

In light of the foregoing, the present teachings provide organic semiconducting compounds that can address various deficiencies and shortcomings of the prior art, including those outlined above. Compounds according to the present teachings can exhibit properties such as optimized optical absorption, good charge transport characteristics and chemical stability in ambient conditions, low-temperature processability, large solubility in common solvents, and processing versatility (e.g., via various solution processes). As a result, optoelectronic devices such as OPV cells that incorporate one or more of the present compounds as a photoactive layer can exhibit high performance in ambient conditions, for example, demonstrating one or more of low band-gap, high fill factor, high open circuit voltage, and high power conversion efficiency, and preferably all of these criteria. Similarly, other organic semiconductor-based devices such as OTFTs can be fabricated efficiently using the organic semiconductor materials described herein.

Generally, the present teachings provide semiconducting compounds that include one or more divalent dithieno[1,2,3]thiadiazole moieties. Such divalent dithieno[1,2,3]thiadiazole moieties can be represented by formula (I):

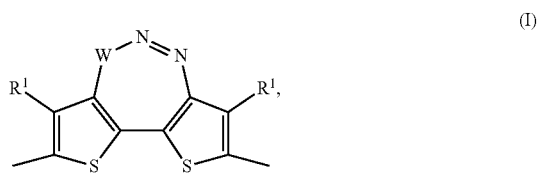

(I)

where W is a chalcogen and $R^1$ is H or a substituent. In some embodiments, the present compound is a polymer having one or more repeating units $M_1$ each of which includes at least one dithieno[1,2,3]thiadiazole moiety, and where the polymer has a degree of polymerization (n) ranging from at least 3. In certain embodiments, the polymer is a homopolymer including only repeating units $M_1$. In other embodiments, the polymer also includes at least one other repeating unit $M_2$ that does not include any dithieno[1,2,3]thiadiazole moiety. Such $M_2$ unit can be selected from:

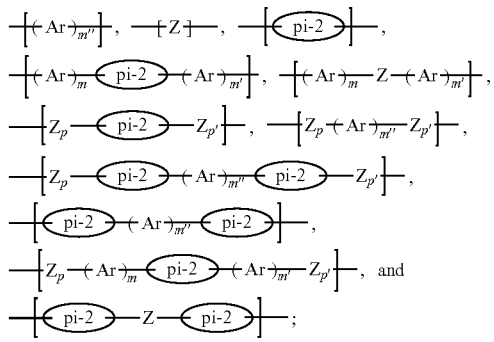

wherein pi-2, Ar, Z, m, m', m", p, and p' are as defined herein. In some embodiments, the present compound is a molecular compound including at least one dithieno[1,2,3]thiadiazole moiety and a plurality of linear and/or cyclic conjugated moieties, such that the compound as a whole provides a pi-extended conjugated system.

The present teachings also provide methods of preparing such compounds and semiconductor materials based on such compounds, as well as various compositions, composites, and devices that incorporate the compounds and semiconductor materials disclosed herein.

The foregoing as well as other features and advantages of the present teachings will be more fully understood from the following figures, description, examples, and claims.

BRIEF DESCRIPTION OF DRAWINGS

It should be understood that the drawings described below are for illustration purpose only. The drawings are not necessarily to scale, with emphasis generally being placed upon illustrating the principles of the present teachings. The drawings are not intended to limit the scope of the present teachings in any way.

FIGS. 1a, 1b, 1c and 1d illustrate four different configurations of thin film transistors: FIG. 1a shows bottom-gate top contact, FIG. 1b shows bottom-gate bottom-contact, FIG. 1c shows top-gate bottom-contact, and FIG. 1d shows top-gate top-contact; each of which can be used to incorporate one or more compounds of the present teachings, particularly as the channel (semiconductor) materials.

DETAILED DESCRIPTION

Figure 2:
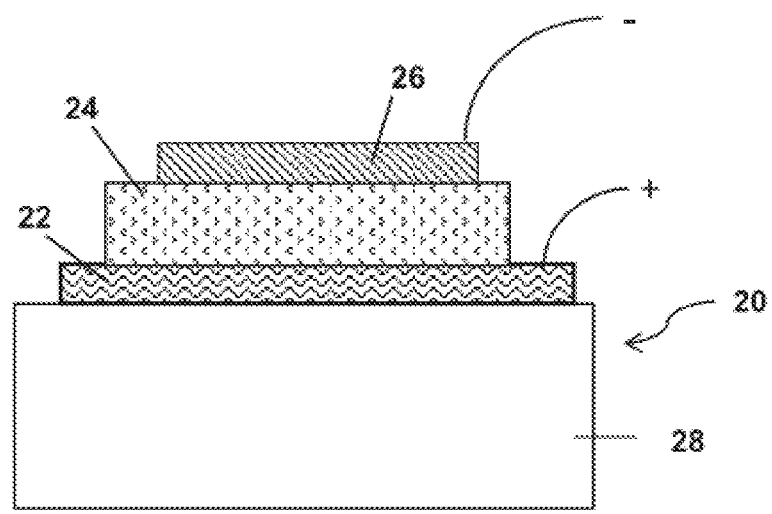
FIG. 2 illustrates a representative structure of a bulk-heterojunction organic photovoltaic device (also known as a solar cell), which can incorporate one or more compounds of the present teachings as the donor and/or acceptor materials.

Throughout the application, where compositions are described as having, including, or comprising specific components, or where processes are described as having, including, or comprising specific process steps, it is contemplated that compositions of the present teachings also consist essentially of, or consist of, the recited components, and that the processes of the present teachings also consist essentially of, or consist of, the recited process steps.

In the application, where an element or component is said to be included in and/or selected from a list of recited elements or components, it should be understood that the element or component can be any one of the recited elements or components and can be selected from a group consisting of two or more of the recited elements or components. Further, it should be understood that elements and/or features of a composition, an apparatus, or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

It should be understood that the order of steps or order for performing certain actions is immaterial so long as the present teachings remain operable. Moreover, two or more steps or actions may be conducted simultaneously.

As used herein, a "p-type semiconductor material" or a "donor" material refers to a semiconductor material, for example, an organic semiconductor material, having holes as the majority current or charge carriers. In some embodiments, when a p-type semiconductor material is deposited on a substrate, it can provide a hole mobility in excess of about $10^{-5}$ cm$^2$/Vs. In the case of field-effect devices, a p-type semiconductor also can exhibit a current on/off ratio of greater than about 10.

As used herein, an "n-type semiconductor material" or an "acceptor" material refers to a semiconductor material, for example, an organic semiconductor material, having electrons as the majority current or charge carriers. In some embodiments, when an n-type semiconductor material is deposited on a substrate, it can provide an electron mobility in excess of about $10^{-5}$ cm$^2$/Vs. In the case of field-effect devices, an n-type semiconductor also can exhibit a current on/off ratio of greater than about 10.

As used herein, "mobility" refers to a measure of the velocity with which charge carriers, for example, holes (or units of positive charge) in the case of a p-type semiconductor material and electrons (or units of negative charge) in the case of an n-type semiconductor material, move through the material under the influence of an electric field. This parameter, which depends on the device architecture, can be measured using a field-effect device or space-charge limited current measurements.

As used herein, a compound can be considered "ambient stable" or "stable at ambient conditions" when a transistor incorporating the compound as its semiconducting material exhibits a carrier mobility that is maintained at about its initial measurement when the compound is exposed to ambient conditions, for example, air, ambient temperature, and humidity, over a period of time. For example, a compound can be described as ambient stable if a transistor incorporating the compound shows a carrier mobility that does not vary more than 20% or more than 10% from its initial value after exposure to ambient conditions, including, air, humidity and temperature, over a 3 day, 5 day, or 10 day period.

As used herein, fill factor (FF) is the ratio (given as a percentage) of the actual maximum obtainable power, ($P_m$ or $V_{mp}*J_{mp}$), to the theoretical (not actually obtainable) power, ($J_{sc}*V_{oc}$). Accordingly, FF can be determined using the equation:

$$FF=(V_{mp}*J_{mp})/(J_{sc}*V_{oc})$$

where $J_{mp}$ and $V_{mp}$ represent the current density and voltage at the maximum power point ($P_m$), respectively, this point being obtained by varying the resistance in the circuit until J*V is at its greatest value; and $J_{sc}$ and $V_{oc}$ represent the short circuit current and the open circuit voltage, respectively. Fill factor is a key parameter in evaluating the performance of solar cells. Commercial solar cells typically have a fill factor of about 0.60% or greater.

As used herein, the open-circuit voltage ($V_{oc}$) is the difference in the electrical potentials between the anode and the cathode of a device when there is no external load connected.

As used herein, the power conversion efficiency (PCE) of a solar cell is the percentage of power converted from incident light to electrical power. The PCE of a solar cell can be calculated by dividing the maximum power point ($P_m$) by the input light irradiance (E, in W/m$^2$) under standard test conditions (STC) and the surface area of the solar cell ($A_c$ in m$^2$). STC typically refers to a temperature of 25° C. and an irradiance of 1000 W/m$^2$ with an air mass 1.5 (AM 1.5) spectrum.

As used herein, a component (such as a thin film layer) can be considered "photoactive" if it contains one or more compounds that can absorb photons to produce excitons for the generation of a photocurrent.

As used herein, "solution-processable" refers to compounds (e.g., polymers), materials, or compositions that can be used in various solution-phase processes including spin-coating, printing (e.g., inkjet printing, gravure printing, offset printing and the like), spray coating, electrospray coating, drop casting, dip coating, and blade coating.

As used herein, a "polymeric compound" (or "polymer") refers to a molecule including a plurality of one or more repeating units connected by covalent chemical bonds. A polymeric compound can be represented by the general formula:

*—(—M—)—* wherein M is the repeating unit or monomer. The polymeric compound can have only one type of repeating unit as well as two or more types of different repeating units. When a polymeric compound has only one type of repeating unit, it can be referred to as a homopolymer. When a polymeric compound has two or more types of different repeating units, the term "copolymer" or "copolymeric compound" can be used instead. For example, a copolymeric compound can include repeating units $$*\text{-}(M^a)\text{-}* \text{ and } *\text{-}(M^b)\text{-}*,$$

where $M^a$ and $M^b$ represent two different repeating units. Unless specified otherwise, the assembly of the repeating units in the copolymer can be head-to-tail, head-to-head, or tail-to-tail. In addition, unless specified otherwise, the copolymer can be a random copolymer, an alternating copolymer, or a block copolymer. For example, the general formula:

$$*\text{-}(M^a_x\text{-}M^b_y)\text{-}*$$

can be used to represent a copolymer of $M^a$ and $M^b$ having x mole fraction of $M^a$ and y mole fraction of $M^b$ in the copolymer, where the manner in which comonomers $M^a$ and $M^b$ is repeated can be alternating, random, regiorandom, regioregular, or in blocks. In addition to its composition, a polymeric compound can be further characterized by its degree of polymerization (n) and molar mass (e.g., number average molecular weight ($M_n$) and/or weight average molecular weight ($M_w$) depending on the measuring technique(s)).

As used herein, "heteroatom" refers to an atom of any element other than carbon or hydrogen and includes, for example, nitrogen, oxygen, silicon, sulfur, phosphorus, and selenium.

As used herein, "halo" or "halogen" refers to fluoro, chloro, bromo, and iodo.

As used herein, "oxo" refers to a double-bonded oxygen (i.e., =O).

As used herein, "alkyl" refers to a straight-chain or branched saturated hydrocarbon group. Examples of alkyl groups include methyl (Me), ethyl (Et), propyl (e.g., n-propyl and iso-propyl), butyl (e.g., n-butyl, iso-butyl, sec-butyl, tert-butyl), pentyl groups (e.g., n-pentyl, iso-pentyl, neopentyl), hexyl groups, and the like. In various embodiments, an alkyl group can have 1 to 40 carbon atoms (i.e., $C_{1-40}$ alkyl group), for example, 1-20 carbon atoms (i.e., $C_{1-20}$ alkyl group). In some embodiments, an alkyl group can have 1 to 6 carbon atoms, and can be referred to as a "lower alkyl group." Examples of lower alkyl groups include methyl, ethyl, propyl (e.g., n-propyl and iso-propyl), and butyl groups (e.g., n-butyl, iso-butyl, sec-butyl, tert-butyl). In some embodiments, alkyl groups can be substituted as described herein. An alkyl group is generally not substituted with another alkyl group, an alkenyl group, or an alkynyl group.

As used herein, "haloalkyl" refers to an alkyl group having one or more halogen substituents. At various embodiments, a haloalkyl group can have 1 to 40 carbon atoms (i.e., $C_{1-40}$ haloalkyl group), for example, 1 to 20 carbon atoms (i.e., $C_{1-20}$ haloalkyl group). Examples of haloalkyl groups include $CF_3$, $C_2F_5$, $CHF_2$, $CH_2F$, $CCl_3$, $CHCl_2$, $CH_2Cl$, $C_2Cl_5$, and the like. Perhaloalkyl groups, i.e., alkyl groups where all of the hydrogen atoms are replaced with halogen atoms (e.g., $CF_3$ and $C_2F_5$), are included within the definition of "haloalkyl." For example, a $C_{1-40}$ haloalkyl group can have the formula $C_zH_{2z+1-t}X^0_t$, where $X^0$, at each occurrence, is F, Cl, Br or I, z is an integer in the range of 1 to 40, and t is an integer in the range of 1 to 81, provided that t is less than or equal to 2z+1. Haloalkyl groups that are not perhaloalkyl groups can be substituted as described herein.

As used herein, "alkoxy" refers to —O-alkyl group. Examples of alkoxy groups include, but are not limited to, methoxy, ethoxy, propoxy (e.g., n-propoxy and isopropoxy), t-butoxy, pentoxyl, hexoxyl groups, and the like. The alkyl group in the —O-alkyl group can be substituted as described herein.

As used herein, "alkylthio" refers to an —S-alkyl group. Examples of alkylthio groups include, but are not limited to, methylthio, ethylthio, propylthio (e.g., n-propylthio and isopropylthio), t-butylthio, pentylthio, hexylthio groups, and the like. The alkyl group in the —S-alkyl group can be substituted as described herein.

As used herein, "alkenyl" refers to a straight-chain or branched alkyl group having one or more carbon-carbon double bonds. Examples of alkenyl groups include ethenyl, propenyl, butenyl, pentenyl, hexenyl, butadienyl, pentadienyl, hexadienyl groups, and the like. The one or more carbon-carbon double bonds can be internal (such as in 2-butene) or terminal (such as in 1-butene). In various embodiments, an alkenyl group can have 2 to 40 carbon atoms (i.e., $C_{2-40}$ alkenyl group), for example, 2 to 20 carbon atoms (i.e., $C_{2-20}$ alkenyl group). In some embodiments, alkenyl groups can be substituted as described herein. An alkenyl group is generally not substituted with another alkenyl group, an alkyl group, or an alkynyl group.

As used herein, "alkynyl" refers to a straight-chain or branched alkyl group having one or more triple carbon-carbon bonds. Examples of alkynyl groups include ethynyl, propynyl, butynyl, pentynyl, hexynyl, and the like. The one or more triple carbon-carbon bonds can be internal (such as in 2-butyne) or terminal (such as in 1-butyne). In various embodiments, an alkynyl group can have 2 to 40 carbon atoms (i.e., $C_{2-40}$ alkynyl group), for example, 2 to 20 carbon atoms (i.e., $C_{2-20}$ alkynyl group). In some embodiments, alkynyl groups can be substituted as described herein. An alkynyl group is generally not substituted with another alkynyl group, an alkyl group, or an alkenyl group.

As used herein, a "cyclic moiety" can include one or more (e.g., 1-6) carbocyclic or heterocyclic rings. In embodiments where the cyclic moiety is a "polycyclic moiety," the "polycyclic moiety" can include two or more rings fused to each other (i.e., sharing a common bond) and/or connected to each other via a spiro atom. The cyclic moiety can be a cycloalkyl group, a heterocycloalkyl group, an aryl group, or a heteroaryl group (i.e., can include only saturated bonds, or can include one or more unsaturated bonds regardless of aromaticity), and can be optionally substituted as described herein. In embodiments where the cyclic moiety is a "monocyclic moiety," the "monocyclic moiety" can include a 3-20 membered carbocyclic or heterocyclic ring. A monocyclic moiety can include a $C_{6-20}$ aryl group (e.g., $C_{6-14}$ aryl group) or a 5-20 membered heteroaryl group (e.g., 5-14 membered heteroaryl group), each of which can be optionally substituted as described herein.

As used herein, "cycloalkyl" refers to a non-aromatic carbocyclic group including cyclized alkyl, alkenyl, and alkynyl groups. In various embodiments, a cycloalkyl group can have 3 to 20 carbon atoms, for example, 3 to 14 carbon atoms (i.e., $C_{3-14}$ cycloalkyl group). A cycloalkyl group can be monocyclic (e.g., cyclohexyl) or polycyclic (e.g., containing fused, bridged, and/or spiro ring systems), where the carbon atoms are located inside or outside of the ring system. Any suitable ring position of the cycloalkyl group can be covalently linked to the defined chemical structure. Examples of cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcaryl, adamantyl, and spiro[4.5] decanyl groups, as well as their homologs, isomers, and the like. In some embodiments, cycloalkyl groups can be substituted as described herein.

As used herein, "cycloheteroalkyl" refers to a non-aromatic cycloalkyl group that contains at least one ring heteroatom selected from O, S, Se, N, P, and Si (e.g., O, S, and N), and optionally contains one or more double or triple bonds. A cycloheteroalkyl group can have 3 to 20 ring atoms, for example, 3 to 14 ring atoms (i.e., 3-14 membered cycloheteroalkyl group). One or more N, P, S, or Se atoms (e.g., N or S) in a cycloheteroalkyl ring may be oxidized (e.g., morpholine N-oxide, thiomorpholine S-oxide, thiomorpholine S,S-dioxide). In some embodiments, nitrogen or phosphorus atoms of cycloheteroalkyl groups can bear a substituent, for example, a hydrogen atom, an alkyl group, or other substituents as described herein. Cycloheteroalkyl groups can also contain one or more oxo groups, such as oxopiperidyl, oxooxazolidyl, dioxo-(1H,3H)-pyrimidyl, oxo-2(1H)-pyridyl, and the like. Examples of cycloheteroalkyl groups include, among others, morpholinyl, thiomorpholinyl, pyranyl, imidazolidinyl, imidazolinyl, oxazolidinyl, pyrazolidinyl, pyrazolinyl, pyrrolidinyl, pyrrolinyl, tetrahydrofuranyl, tetrahydrothiophenyl, piperidinyl, piperazinyl, and the like. In some embodiments, cycloheteroalkyl groups can be substituted as described herein.

As used herein, "aryl" refers to an aromatic monocyclic hydrocarbon ring system or a polycyclic ring system in which two or more aromatic hydrocarbon rings are fused (i.e., having a bond in common with) together or at least one aromatic monocyclic hydrocarbon ring is fused to one or more cycloalkyl and/or cycloheteroalkyl rings. An aryl group can have 6 to 22 carbon atoms in its ring system (e.g., $C_{6-14}$ aryl group), which can include multiple fused rings. In some embodiments, a polycyclic aryl group can have from 8 to 22 carbon atoms. Any suitable ring position of the aryl group can be covalently linked to the defined chemical structure. Examples of aryl groups having only aromatic carbocyclic ring(s) include phenyl, 1-naphthyl (bicyclic), 2-naphthyl (bicyclic), anthracenyl (tricyclic), phenanthrenyl (tricyclic), pentacenyl (pentacyclic) and like groups. Examples of polycyclic ring systems in which at least one aromatic carbocyclic ring is fused to one or more cycloalkyl and/or cycloheteroalkyl rings include, among others, benzo derivatives of cyclopentane (i.e., an indanyl group, which is a 5,6-bicyclic cycloalkyl/aromatic ring system), cyclohexane (i.e., a tetrahydronaphthyl group, which is a 6,6-bicyclic cycloalkyl/aromatic ring system), imidazoline (i.e., a benzimidazolinyl group, which is a 5,6-bicyclic cycloheteroalkyl/aromatic ring system), and pyran (i.e., a chromenyl group, which is a 6,6-bicyclic cycloheteroalkyl/aromatic ring system). Other examples of aryl groups include benzodioxanyl, benzodioxolyl, chromanyl, indolinyl groups, and the like. In some embodiments, aryl groups can be substituted as described herein. In some embodiments, an aryl group can have one or more halogen substituents, and can be referred to as a "haloaryl" group. Perhaloaryl groups, i.e., aryl groups where all of the hydrogen atoms are replaced with halogen atoms (e.g., —$C_6F_5$), are included within the definition of "haloaryl." In certain embodiments, an aryl group is substituted with another aryl group and can be referred to as a biaryl group. Each of the aryl groups in the biaryl group can be substituted as disclosed herein.

As used herein, "arylalkyl" refers to an -alkyl-aryl group, where the arylalkyl group is covalently linked to the defined chemical structure via the alkyl group. An arylalkyl group is within the definition of a —Y—$C_{6-14}$ aryl group, where Y is as defined herein. An example of an arylalkyl group is a benzyl group (—$CH_2$—$C_6H_5$). An arylalkyl group can be optionally substituted, i.e., the aryl group and/or the alkyl group, can be substituted as disclosed herein.

As used herein, "heteroaryl" refers to an aromatic monocyclic ring system containing at least one ring heteroatom selected from oxygen (O), nitrogen (N), sulfur (S), silicon (Si), and selenium (Se) or a polycyclic ring system where at least one of the rings present in the ring system is aromatic and contains at least one ring heteroatom. Polycyclic heteroaryl groups include two or more heteroaryl rings fused together and monocyclic heteroaryl rings fused to one or more aromatic carbocyclic rings, non-aromatic carbocyclic rings, and/or non-aromatic cycloheteroalkyl rings. A heteroaryl group, as a whole, can have, for example, 5 to 22 ring atoms and contain 1-5 ring heteroatoms (i.e., 5-20 membered heteroaryl group). The heteroaryl group can be attached to the defined chemical structure at any heteroatom or carbon atom that results in a stable structure. Generally, heteroaryl rings do not contain O—O, S—S, or S—O bonds. However, one or more N or S atoms in a heteroaryl group can be oxidized (e.g., pyridine N-oxide, thiophene S-oxide, thiophene S,S-dioxide). Examples of heteroaryl groups include, for example, the 5- or 6-membered monocyclic and 5-6 bicyclic ring systems shown below:

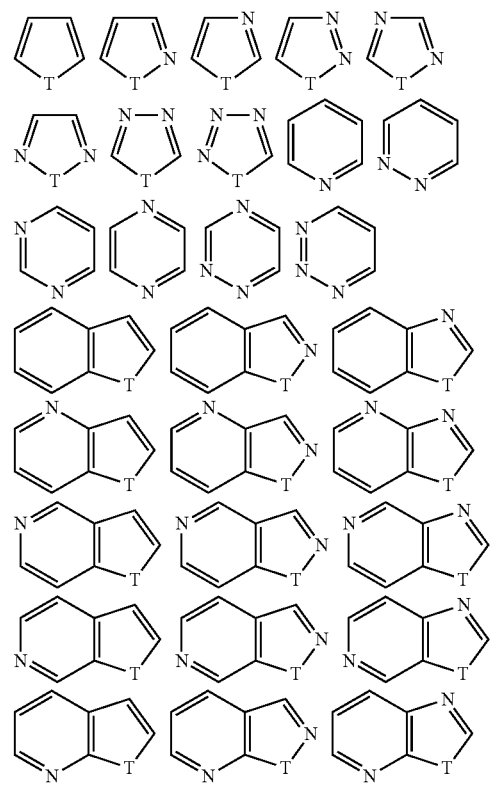

where T is O, S, NH, N-alkyl, N-aryl, N-(arylalkyl) (e.g., N-benzyl), $SiH_2$, SiH(alkyl), $Si(alkyl)_2$, SiH(arylalkyl), $Si(arylalkyl)_2$, or Si(alkyl)(arylalkyl). Examples of such heteroaryl rings include pyrrolyl, furyl, thienyl, pyridyl, pyrimidyl, pyridazinyl, pyrazinyl, triazolyl, tetrazolyl, pyrazolyl, imidazolyl, isothiazolyl, thiazolyl, thiadiazolyl, isoxazolyl, oxazolyl, oxadiazolyl, indolyl, isoindolyl, benzofuryl, benzothienyl, quinolyl, 2-methylquinolyl, isoquinolyl, quinoxalyl, quinazolyl, benzotriazolyl, benzimidazolyl, benzothiazolyl, benzisothiazolyl, benzisoxazolyl, benzoxadiazolyl, benzoxazolyl, cinnolinyl, 1H-indazolyl, 2H-indazolyl, indolizinyl, isobenzofuyl, naphthyridinyl, phthalazinyl, pteridinyl, purinyl, oxazolopyridinyl, thiazolopyridinyl, imidazopyridinyl, furopyridinyl, thienopyridinyl, pyridopyrimidinyl, pyridopyrazinyl, pyridopyridazinyl, thienothiazolyl, thienoxazolyl, thienoimidazolyl groups, and the like. Further examples of heteroaryl groups include 4,5,6,7-tetrahydroindolyl, tetrahydroquinolinyl, benzothienopyridinyl, benzofuropyridinyl groups, and the like. In some embodiments, heteroaryl groups can be substituted as described herein.

Compounds of the present teachings can include a "divalent group" defined herein as a linking group capable of forming a covalent bond with two other moieties. For example, compounds of the present teachings can include a divalent $C_{1-20}$ alkyl group (e.g., a methylene group), a divalent $C_{2-20}$ alkenyl group (e.g., a vinylyl group), a divalent $C_{2-20}$ alkynyl group (e.g., an ethynylyl group). a divalent $C_{6-14}$ aryl group (e.g., a phenylyl group); a divalent 3-14 membered cycloheteroalkyl group (e.g., a pyrrolidylyl), and/or a divalent 5-14 membered heteroaryl group (e.g., a thienylyl group).

The electron-donating or electron-withdrawing properties of several hundred of the most common substituents, reflecting all common classes of substituents have been determined, quantified, and published. The most common quantification of electron-donating and electron-withdrawing properties is in terms of Hammett σ values. Hydrogen has a Hammett σ value of zero, while other substituents have Hammett σ values that increase positively or negatively in direct relation to their electron-withdrawing or electron-donating characteristics. Substituents with negative Hammett σ values are considered electron-donating, while those with positive Hammett σ values are considered electron-withdrawing. See Lange's Handbook of Chemistry, 12th ed., McGraw Hill, 1979, Table 3-12, pp. 3-134 to 3-138, which lists Hammett σ values for a large number of commonly encountered substituents and is incorporated by reference herein.

It should be understood that the term "electron-accepting group" can be used synonymously herein with "electron acceptor" and "electron-withdrawing group". In particular, an "electron-withdrawing group" ("EWG") or an "electron-accepting group" or an "electron-acceptor" refers to a functional group that draws electrons to itself more than a hydrogen atom would if it occupied the same position in a molecule. Examples of electron-withdrawing groups include, but are not limited to, halogen or halo (e.g., F, Cl, Br, I), —$NO_2$, —CN, —NC, —$S(R^o)_2^+$, $N(R^o)_3^+$, —$SO_3H$, —$SO_2R^o$, —$SO_3R^o$, —$SO_2NHR^o$, —$SO_2N(R^o)_2$, —COOH, —$COR^o$, —$COOR^o$, —$CONHR^o$, —$CON(R^o)_2$, $C_{1-40}$ haloalkyl groups, $C_{6-14}$ aryl groups, and 5-14 membered electron-poor heteroaryl groups; where $R^o$ is a $C_{1-20}$ alkyl group, a $C_{2-20}$ alkenyl group, a $C_{2-20}$ alkynyl group, a $C_{1-20}$ haloalkyl group, a $C_{1-20}$ alkoxy group, a $C_{6-14}$ aryl group, a $C_{3-14}$ cycloalkyl group, a 3-14 membered cycloheteroalkyl group, and a 5-14 membered heteroaryl group, each of which can be optionally substituted as described herein. For example, each of the $C_{1-20}$ alkyl group, the $C_{2-20}$ alkenyl group, the $C_{2-20}$ alkynyl group, the $C_{1-20}$ haloalkyl group, the $C_{1-20}$ alkoxy group, the $C_{6-14}$ aryl group, the $C_{3-14}$ cycloalkyl group, the 3-14 membered cycloheteroalkyl group, and the 5-14 membered heteroaryl group can be optionally substituted with 1-5 small electron-withdrawing groups such as F, Cl, Br, —$NO_2$, —CN, —NC, —$S(R^o)_2^+$, —$N(R^o)_3^+$, —$SO_3H$, —$SO_2R^o$, —$SO_3R^o$, —$SO_2NHR^o$, —$SO_2N(R^o)_2$, —COOH, —$COR^o$, —$COOR^o$, —$CONHR^o$, and —$CON(R^o)_2$.

It should be understood that the term "electron-donating group" can be used synonymously herein with "electron donor". In particular, an "electron-donating group" or an "electron-donor" refers to a functional group that donates electrons to a neighboring atom more than a hydrogen atom would if it occupied the same position in a molecule. Examples of electron-donating groups include —OH, —$OR^o$, —$NH_2$, —$NHR^o$, —$N(R^o)_2$, and 5-14 membered electron-rich heteroaryl groups, where $R^o$ is a $C_{1-20}$ alkyl group, a $C_{2-20}$ alkenyl group, a $C_{2-20}$ alkynyl group, a $C_{6-14}$ aryl group, or a $C_{3-14}$ cycloalkyl group.

Various unsubstituted heteroaryl groups can be described as electron-rich (or π-excessive) or electron-poor (or π-deficient). Such classification is based on the average electron density on each ring atom as compared to that of a carbon atom in benzene. Examples of electron-rich systems include 5-membered heteroaryl groups having one heteroatom such as furan, pyrrole, and thiophene; and their benzofused counterparts such as benzofuran, benzopyrrole, and benzothiophene. Examples of electron-poor systems include 6-membered heteroaryl groups having one or more heteroatoms such as pyridine, pyrazine, pyridazine, and pyrimidine; as well as their benzofused counterparts such as quinoline, isoquinoline, quinoxaline, cinnoline, phthalazine, naphthyridine, quinazoline, phenanthridine, acridine, and purine. Mixed heteroaromatic rings can belong to either class depending on the type, number, and position of the one or more heteroatom(s) in the ring. See Katritzky, A. R and Lagowski, J. M., *Heterocyclic Chemistry* (John Wiley & Sons, New York, 1960).

At various places in the present specification, substituents of monomers A and B are disclosed in groups or in ranges. It is specifically intended that the description include each and every individual subcombination of the members of such groups and ranges. For example, the term "$C_{1-6}$ alkyl" is specifically intended to individually disclose $C_1$, $C_2$, $C_3$, $C_4$, $C_5$, $C_6$, $C_1$-$C_6$, $C_1$-$C_5$, $C_1$-$C_4$, $C_1$-$C_3$, $C_1$-$C_2$, $C_2$-$C_6$, $C_2$-$C_5$, $C_2$-$C_4$, $C_2$-$C_3$, $C_3$-$C_6$, $C_3$-$C_5$, $C_3$-$C_4$, $C_4$-$C_6$, $C_4$-$C_5$, and $C_5$-$C_6$ alkyl. By way of other examples, an integer in the range of 0 to 40 is specifically intended to individually disclose 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, and 40, and an integer in the range of 1 to 20 is specifically intended to individually disclose 1, 2, 3, 4, 5, 6, 7, 8, 9, 10, 11, 12, 13, 14, 15, 16, 17, 18, 19, and 20. Additional examples include that the phrase "optionally substituted with 1-5 substituents" is specifically intended to individually disclose a chemical group that can include 0, 1, 2, 3, 4, 5, 0-5, 0-4, 0-3, 0-2, 0-1, 1-5, 1-4, 1-3, 1-2, 2-5, 2-4, 2-3, 3-5, 3-4, and 4-5 substituents.

Compounds described herein can contain an asymmetric atom (also referred as a chiral center) and some of the compounds can contain two or more asymmetric atoms or centers, which can thus give rise to optical isomers (enantiomers) and diastereomers (geometric isomers). The present teachings include such optical isomers and diastereomers, including their respective resolved enantiomerically or diastereomerically pure isomers (e.g., (+) or (−) stereoisomer) and their racemic mixtures, as well as other mixtures of the enantiomers and diastereomers. In some embodiments, optical isomers can be obtained in enantiomerically enriched or pure form by standard procedures known to those skilled in the art, which include, for example, chiral separation, diastereomeric salt formation, kinetic resolution, and asymmetric synthesis. The present teachings also encompass cis- and trans-isomers of compounds containing alkenyl moieties (e.g., alkenes, azo, and imines). It also should be understood that compounds of the present teachings encompass all possible regioisomers in pure form and mixtures thereof. It may be possible to separate such isomers, for example, using standard separation procedures known to those skilled in the art, for example, column chromatography, thin-layer chromatography, simulated moving-bed chromatography, and high-performance liquid chromatography. However, mixtures of regioisomers can be used similarly to the uses of each individual regioisomer of the present teachings.

It is specifically contemplated that the depiction of one regioisomer includes any other regioisomers and any regioisomeric mixtures unless specifically stated otherwise.

As used herein, a "leaving group" ("LG") refers to a charged or uncharged atom (or group of atoms) that can be displaced as a stable species as a result of, for example, a substitution or elimination reaction. Examples of leaving groups include, but are not limited to, halogen (e.g., Cl, Br, I), azide ($N_3$), thiocyanate (SCN), nitro ($NO_2$), cyanate (CN), water ($H_2O$), ammonia ($NH_3$), and sulfonate groups (e.g., $OSO_2$—R, wherein R can be a $C_{1-10}$ alkyl group or a $C_{6-14}$ aryl group each optionally substituted with 1-4 groups independently selected from a $C_{1-10}$ alkyl group and an electron-withdrawing group) such as tosylate (toluenesulfonate, OTs), mesylate (methanesulfonate, OMs), brosylate (p-bromobenzenesulfonate, OBs), nosylate (4-nitrobenzenesulfonate, ONs), and triflate (trifluoromethanesulfonate, OTf).

Throughout the specification, structures may or may not be presented with chemical names. Where any question arises as to nomenclature, the structure prevails.

The present teachings relate to molecular and polymeric compounds that can be used as organic semiconductor materials. The present compounds can have good solubility in various common organic solvents and good stability in air. When incorporated into optical, electronic or optoelectronic devices including, but not limited to, organic photovoltaic or solar cells, organic light emitting diodes, and organic field effect transistors, the present compounds can confer various desirable performance properties.

More specifically, the present teachings provide semiconducting compounds that include one or more moieties represented by formula (I):

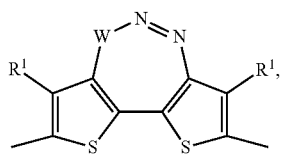
(I)

where W is selected from the group consisting of S, Se, and Te; and
each $R^1$ independently is selected from the group consisting of H, halogen, —CN, $NO_2$, $R^2$, -L-$R^3$, OH, $OR^2$, $OR^3$, $NH_2$, $NHR^2$, $N(R^2)_2$, $NR^2R^3$, $N(R^3)_2$, SH, $SR^2$, $SR^3$, $S(O)_2OH$, —$S(O)_2OR^2$, —$S(O)_2OR^3$, C(O)H, C(O)$R^2$, C(O)$R^3$, C(O)OH, C(O)$OR^2$, C(O)$OR^3$, C(O)$NH_2$, C(O)$NHR^2$, C(O)N($R^2)_2$, C(O)$NR^2R^3$, C(O)N($R^3)_2$, $SiH_3$, $SiH(R^2)_2$, $SiH_2(R^2)$, and $Si(R^2)_3$, wherein L is selected from the group consisting of a divalent $C_{1-40}$ alkyl group, a divalent $C_{2-40}$ alkenyl group, a divalent $C_{1-40}$ haloalkyl group, and a covalent bond; each $R^2$ independently is selected from a $C_{1-40}$ alkyl group, a $C_{2-40}$ alkenyl group, a $C_{2-40}$ alkynyl group, and a $C_{1-40}$ haloalkyl group; and each $R^3$ independently is selected from the group consisting of a $C_{3-10}$ cycloalkyl group, a $C_{6-14}$ aryl group, a $C_{6-14}$ haloaryl group, a 3-12 membered cycloheteroalkyl group, and a 5-14 membered heteroaryl group, each of which optionally is substituted with 1-5 substituents independently selected from the group consisting of halogen, —CN, $NO_2$, $R^2$, $OR^2$, and $SR^2$.

In preferred embodiments, the one or more moieties represented by formula (I) are optionally substituted dithieno[1,2,3]thiadiazole moieties represented by formula (II):

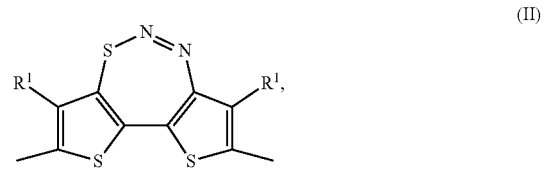
(II)

wherein $R^1$ is as defined herein. For example, $R^1$ can be selected from the group consisting of F, Cl, —CN, —$NO_2$, $R^2$, $OR^2$, and $SR^2$, wherein $R^2$ is selected from the group consisting of a linear or branched $C_{1-40}$ alkyl group, a linear or branched $C_{2-40}$ alkenyl group, and a linear or branched $C_{1-40}$ haloalkyl group. In other embodiments, $R^1$ is H and the one or more moieties represented by formula (I) are unsubstituted dithieno[1,2,3]thiadiazole moieties represented by formula (III):

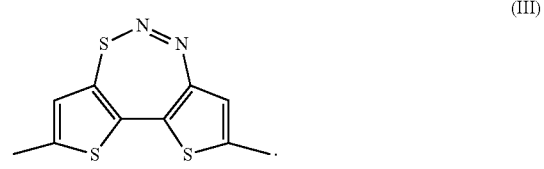
(III)

In some embodiments, the present compound is a polymer having one or more repeating units $M_1$, where each $M_1$ includes at least one moiety represented by formula (I), and where the polymer has a degree of polymerization (n) ranging from at least 3.

Other than the moieties represented by formula (I), repeating units $M_1$ optionally can include one or more spacers (Sp) which can be either non-cyclic (Z) or cyclic, particularly monocyclic (Ar) or polycyclic (pi-2), which together with the moieties of formula (I) can provide a pi-extended conjugated group. For example, $M_1$ can be selected from the group consisting of:

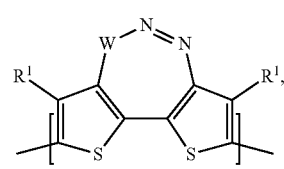

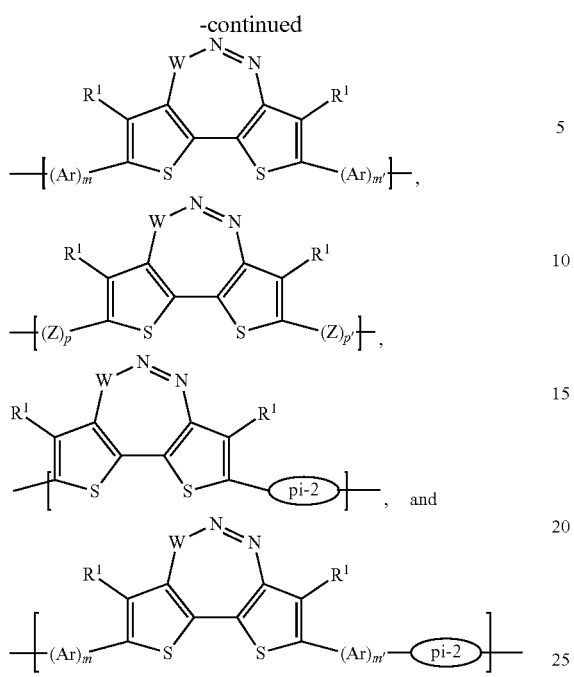

wherein:

pi-2 is an optionally substituted conjugated polycyclic moiety;

Ar, at each occurrence, independently is an optionally substituted 5- or 6-membered aryl or heteroaryl group;

Z is a conjugated noncyclic linker;

m and m' independently are 0, 1, 2, 3, 4, 5 or 6, provided that at least one of m and m' is not 0; and p and p' independently are 0 and 1, provided that at least one of p and p' is 1.

To illustrate, the polycyclic conjugated moiety, pi-2, can be an optionally substituted $C_{8-26}$ aryl group or 8-26 membered heteroaryl group. For example, pi-2 can have a planar and pi-extended conjugated cyclic core which can be optionally substituted as disclosed herein. Examples of suitable cyclic cores include naphthalene, anthracene, tetracene, pentacene, perylene, pyrene, coronene, fluorene, indacene, indenofluorene, and tetraphenylene, as well as their analogs in which one or more carbon atoms can be replaced with a heteroatom such as O, S, Si, Se, N, or P.

In certain embodiments, pi-2 can be selected from the group consisting of:

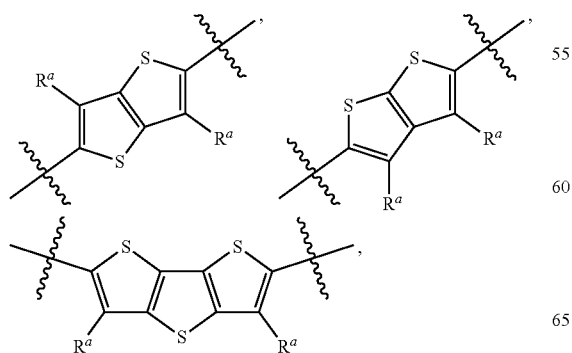

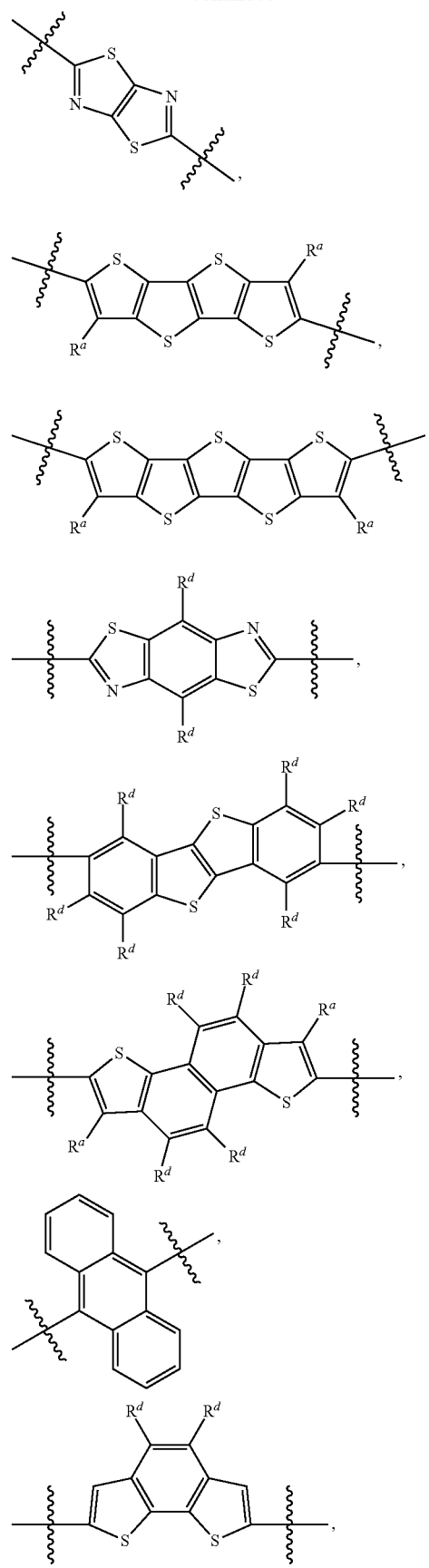

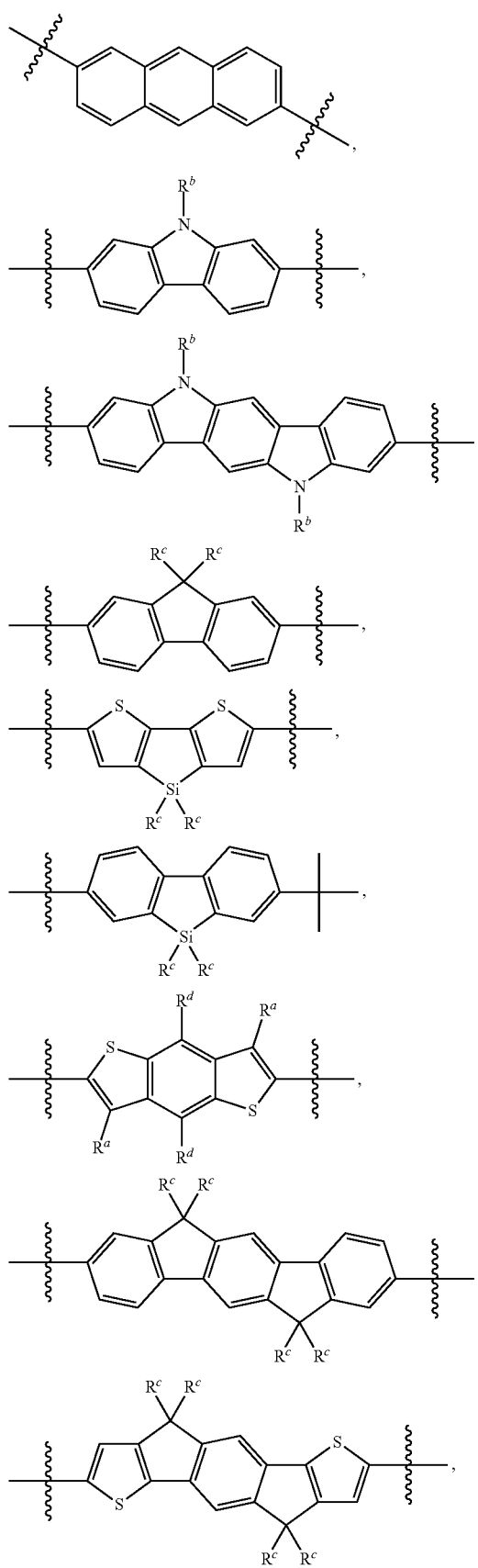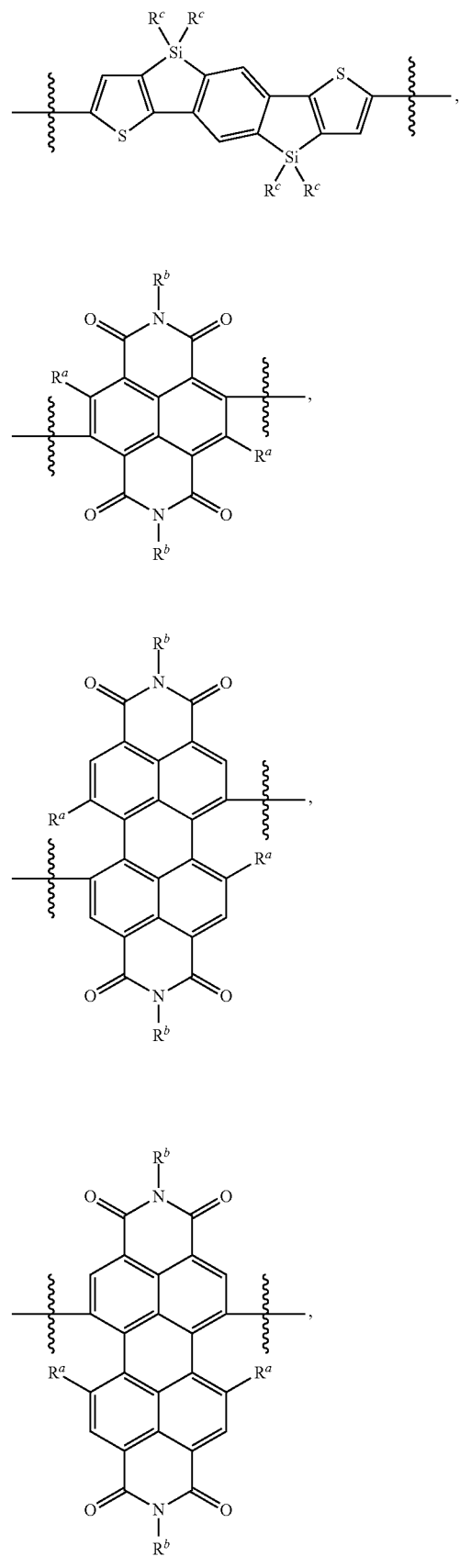

-continued
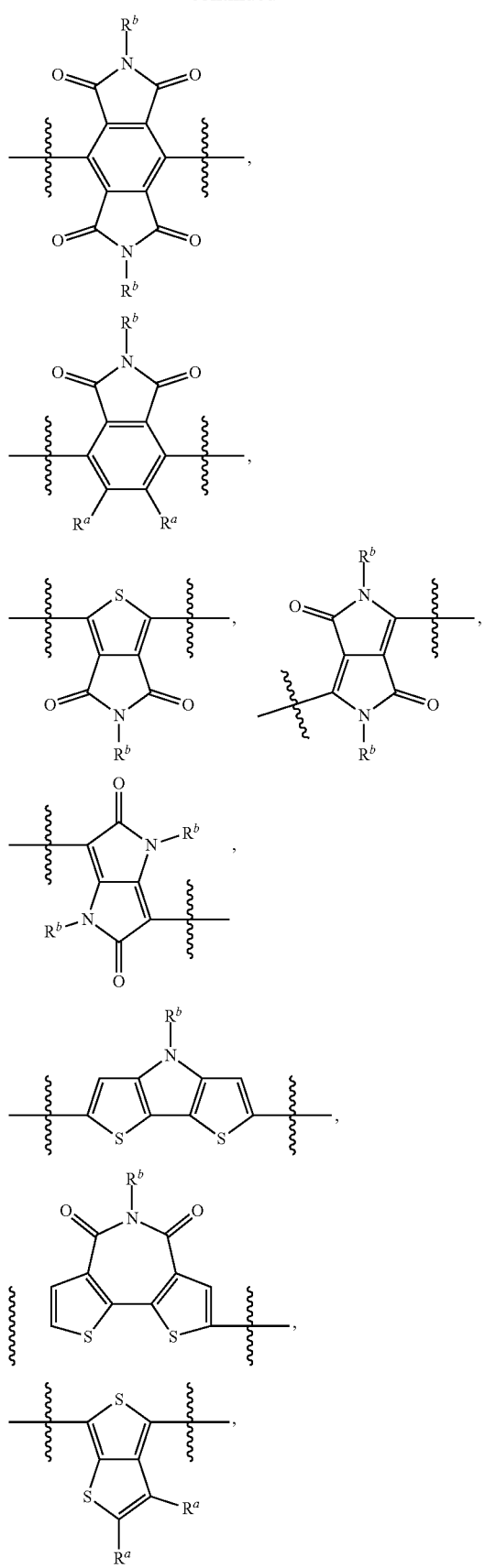
-continued
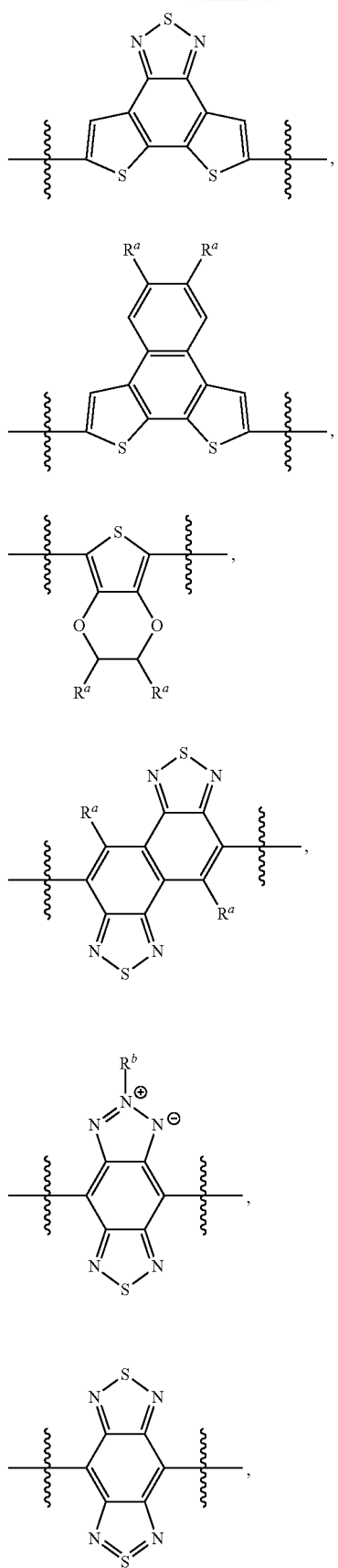

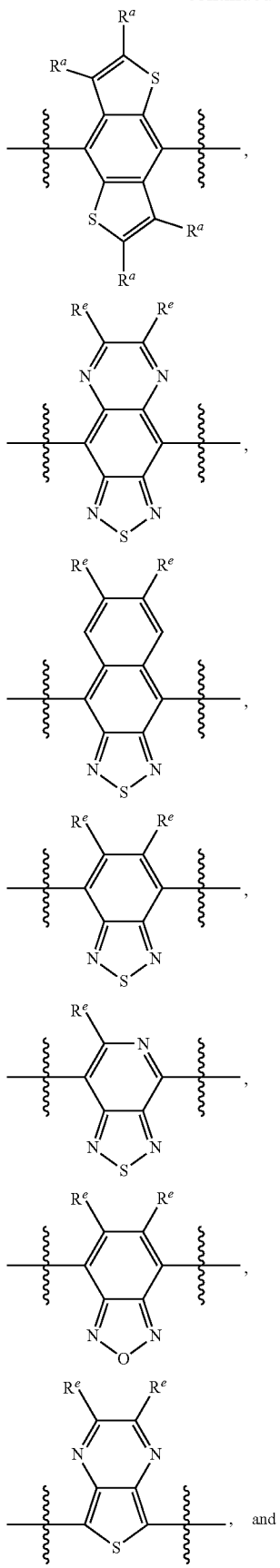

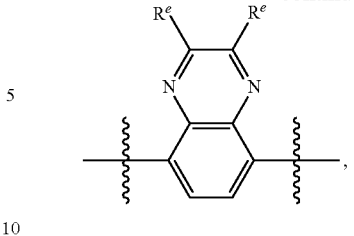

wherein:
$R^a$ is selected from the group consisting of H, F, Cl, —CN, R, —OR, —SR, —C(O)R, —OC(O)R, and —C(O)OR;
$R^b$ is selected from the group consisting of H, R, and -L-$R^f$;
$R^c$ is H or R;
$R^d$ is selected from the group consisting of H, F, Cl, —CN, R, —OR, —SR, —C(O)R, —OC(O)R, —C(O)OR, and -L-$R^f$;
$R^e$ is selected from the group consisting of H, F, Cl, —CN, R, —OR, —SR, —C(O)R, —OC(O)R, —C(O)OR, and $R^f$;
$R^f$ is a $C_{6-20}$ aryl group or a 5-20-membered heteroaryl group, each optionally substituted with 1-8 groups independently selected from the group consisting of F, Cl, —CN, R, —OR, and —SR;
L is selected from the group consisting of —O—, —S—, —C(O)—, —OC(O)—, —C(O)O—, and a covalent bond; and
R is selected from the group consisting of a $C_{1-40}$ alkyl group, a $C_{1-40}$ haloalkyl group, a $C_{2-40}$ alkenyl group, and a $C_{2-40}$ alkynyl group.

The monocyclic conjugated moiety, Ar, at each occurrence, independently can be an optionally substituted 5- or 6-membered (hetero)aryl group. For example, Ar can be selected from the group consisting of a phenyl group, a thienyl group, a thiazolyl group, an isothiazolyl group, a thiadiazolyl group, a furyl group, an oxazolyl group, an isoxazolyl group, an oxadiazolyl group, a pyrrolyl group, a triazolyl group, a tetrazolyl group, a pyrazolyl group, an imidazolyl group, a pyridyl group, a pyrimidyl group, a pyridazinyl group, and a pyrazinyl group, each of which optionally can be substituted with 1-4 $R^5$ groups independently selected from a halogen, CN, a $C_{1-40}$ alkyl group, a $C_{1-40}$ haloalkyl group, a $C_{1-40}$ alkoxy group, and a $C_{1-40}$ alkylthio group.

By way of example, each Ar in $(Ar)_m$ and/or $(Ar)_{m'}$ that is present (i.e., when m and/or m' is 1, 2, 3, 4, 5 or 6) can be represented by:

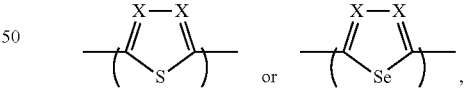

where each X independently can be selected from the group consisting of N, CH, and $CR^4$, wherein $R^4$ can be selected from the group consisting of F, Cl, —CN, $R^2$, $OR^2$, $SR^2$, $C(O)R^2$, $OC(O)R^2$, and $C(O)OR^2$, where $R^2$ is as defined herein. To illustrate further, $(Ar)_m$ or $(Ar)_{m'}$ when present can be selected from the group consisting of:

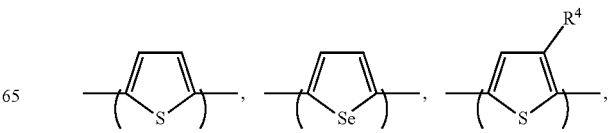

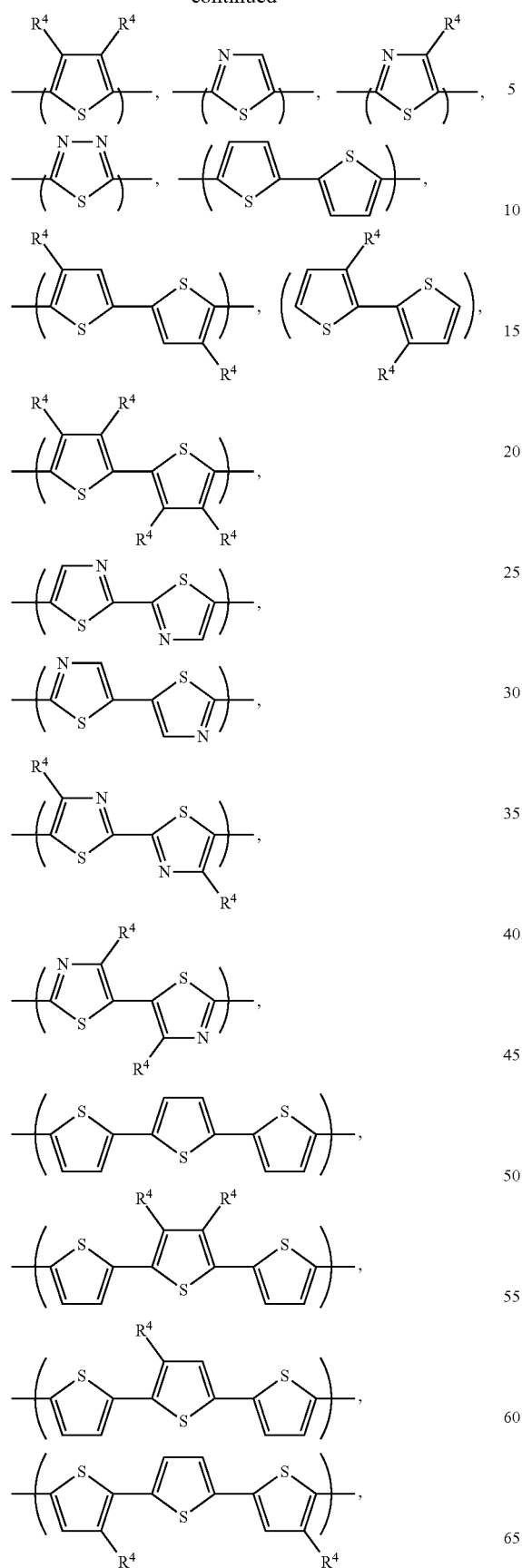
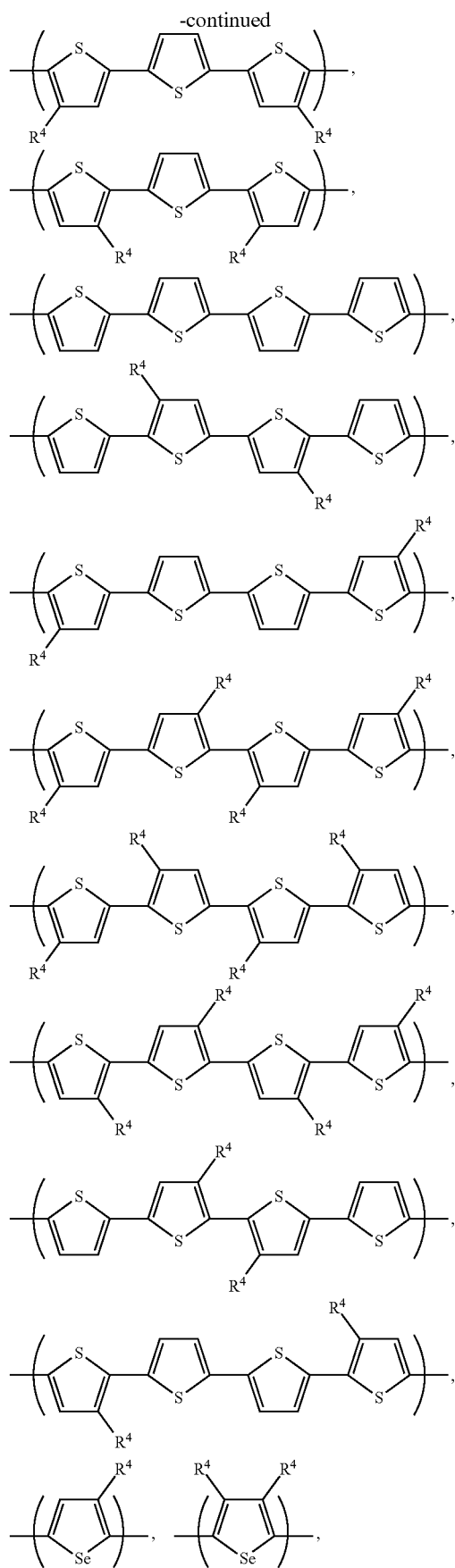

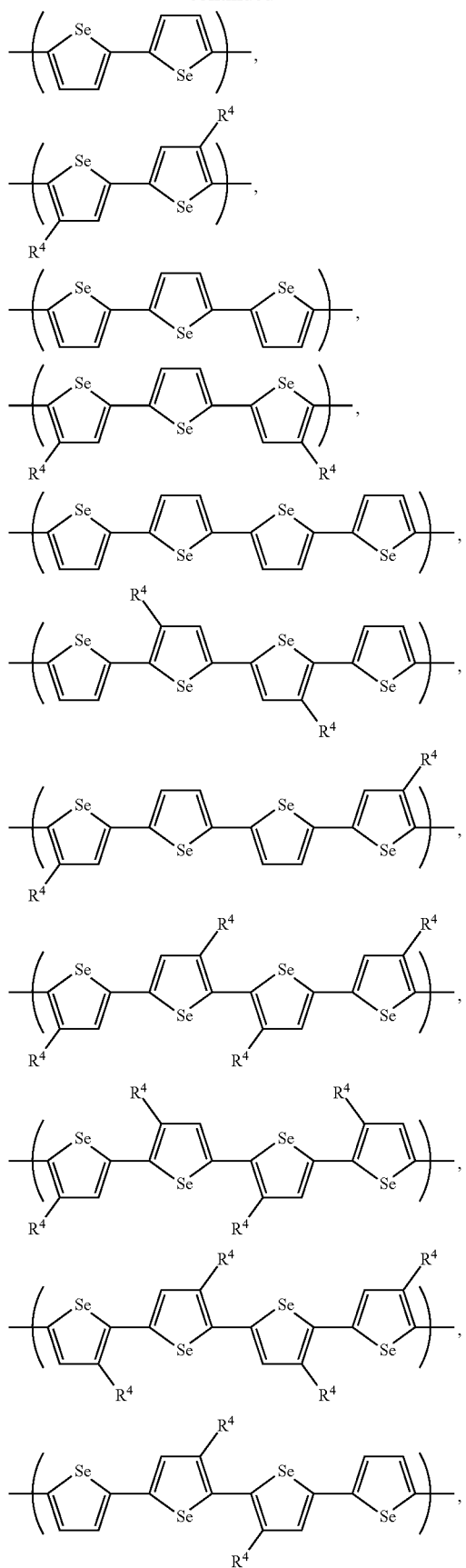

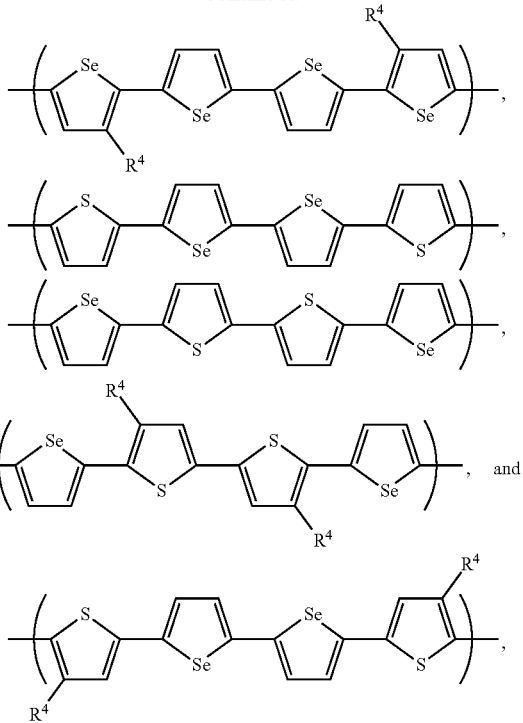

where, for example, each $R^4$ independently is selected from the group consisting of F, Cl, CN, $R^2$, $OR^2$, and $SR^2$, where $R^2$ is a linear or branched $C_{1-40}$ alkyl or haloalkyl group.

The conjugated noncyclic linker, Z, can include one or more double or triple bonds. For example, Z can be a divalent ethenyl group (i.e., having one double bond), a divalent ethynyl group (i.e., having one tripe bond), a $C_{4-40}$ alkenyl or alkynyl group that includes two or more conjugated double or triple bonds, or some other linear or branched conjugated systems that can include heteroatoms such as Si, N, P, and the like. In certain embodiments, Z can be selected from:

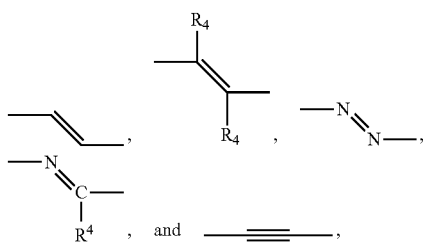

wherein $R^4$ is as defined herein. In particular embodiments, Z can be selected from:

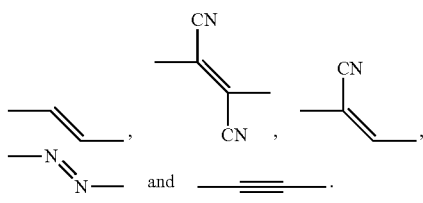

In preferred embodiments, the present polymer includes a repeating unit $M_1$ selected from the group consisting of:

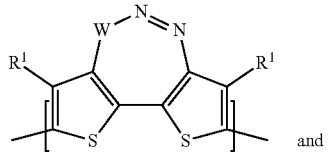
and
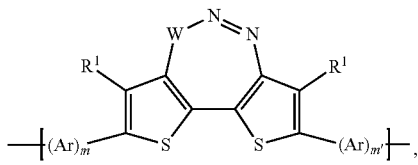

where Ar, $R^1$, W, m, and m' are as defined herein.

More preferably, $M_1$ is selected from the group consisting of:

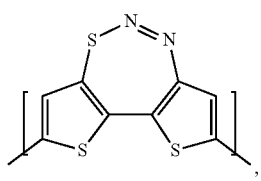

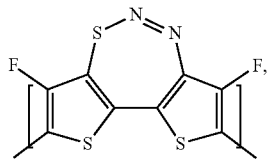

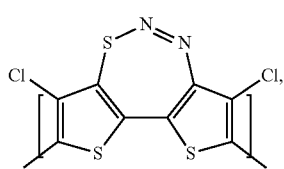

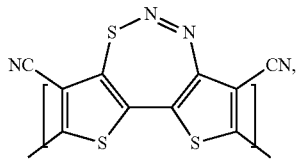

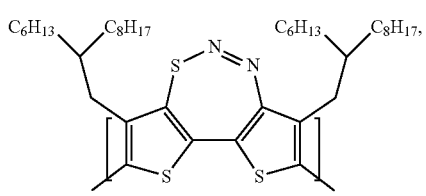

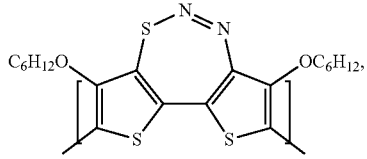

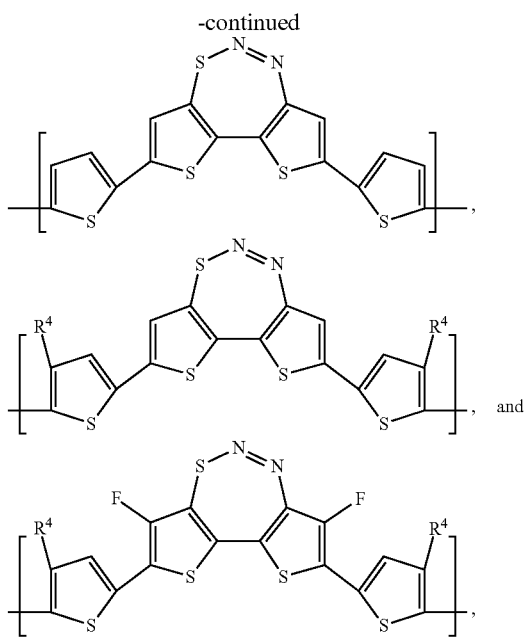

wherein $R^4$ can be selected from the group consisting of $R^2$, $OR^2$, and $SR^2$, where $R^2$ is a linear or branched $C_{1-40}$ alkyl or haloalkyl group.

In certain embodiments, the present polymer can be a homopolymer including only identical repeating units $M_1$. In other embodiments, the polymer can be a copolymer including two or more different repeating units $M_1$. In yet other embodiments, the polymer can be a copolymer including at least one repeating unit $M_1$ and at least one other repeating unit $M_2$ that does not include any moiety of formula (I). Such $M_2$ units can include one or more non-cyclic (Z), monocyclic (Ar), and/or polycyclic (pi-2) conjugated linkers, which together provide a pi-extended conjugated group. For example, $M_2$ can be selected from:

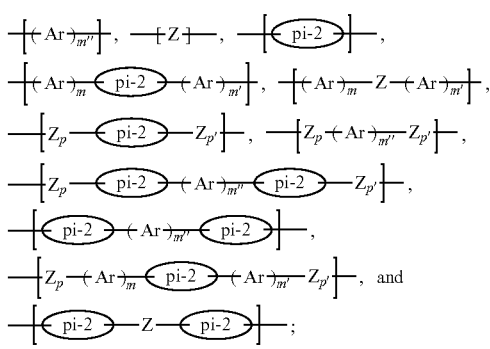

wherein pi-2, Ar, Z, m, m', m", p, and p' are as defined herein.

To illustrate, in certain embodiments, $M_2$ can have the formula:

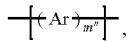

wherein m" is selected from 1, 2, 3, or 4; and Ar is as defined herein. For example, $M_2$ can be selected from the group consisting of:

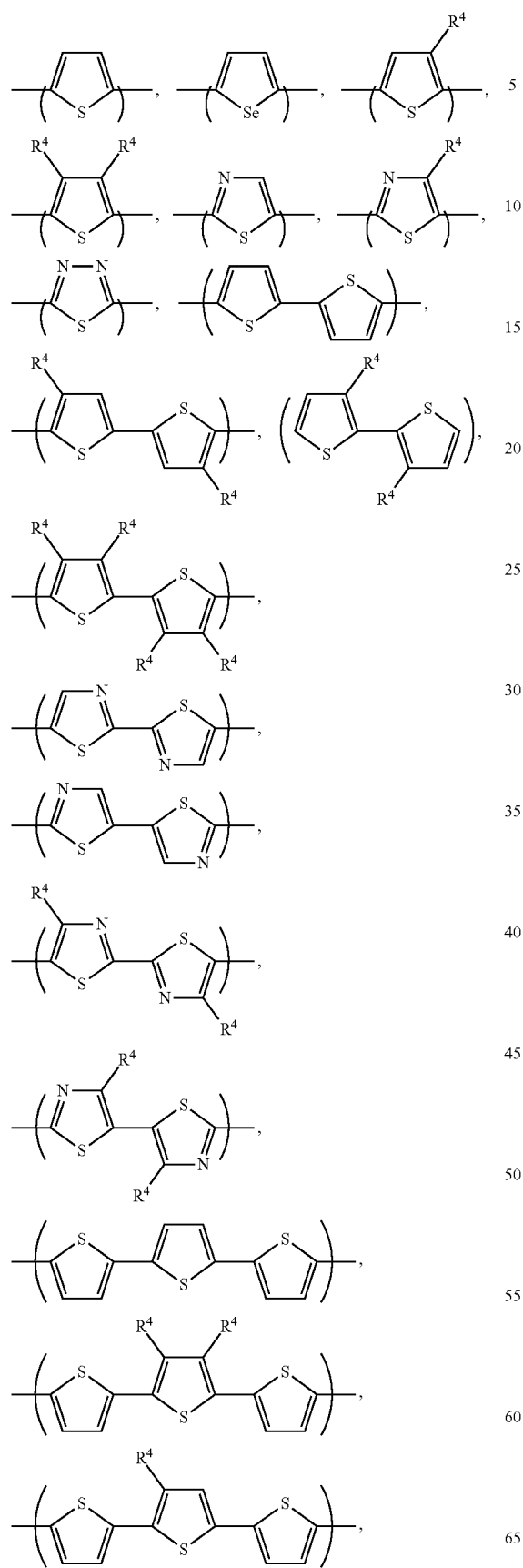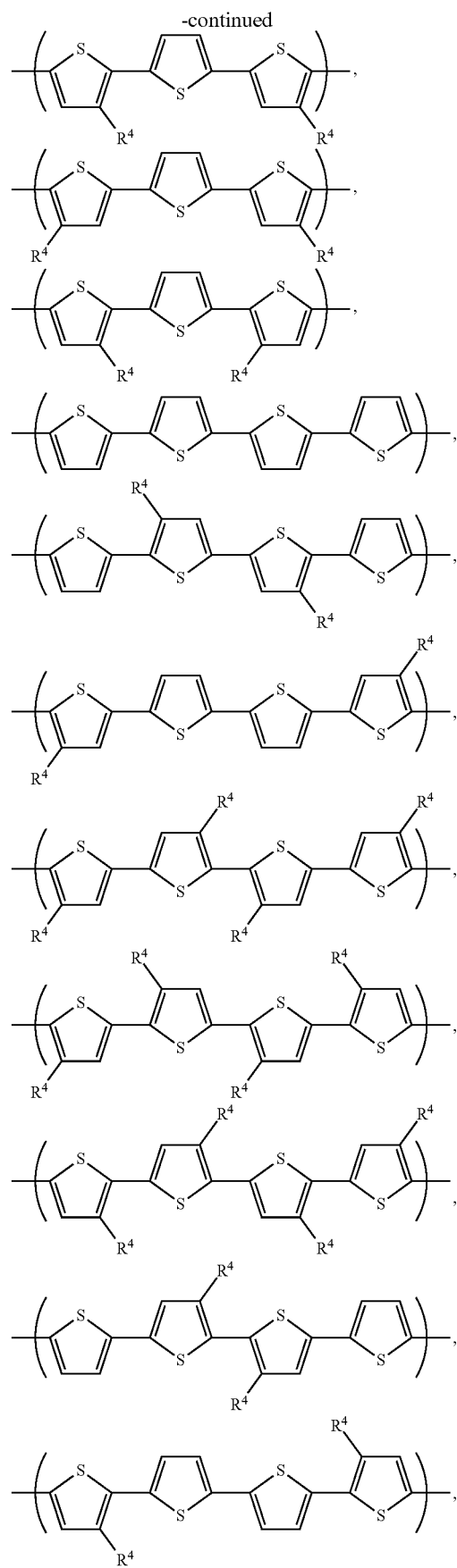

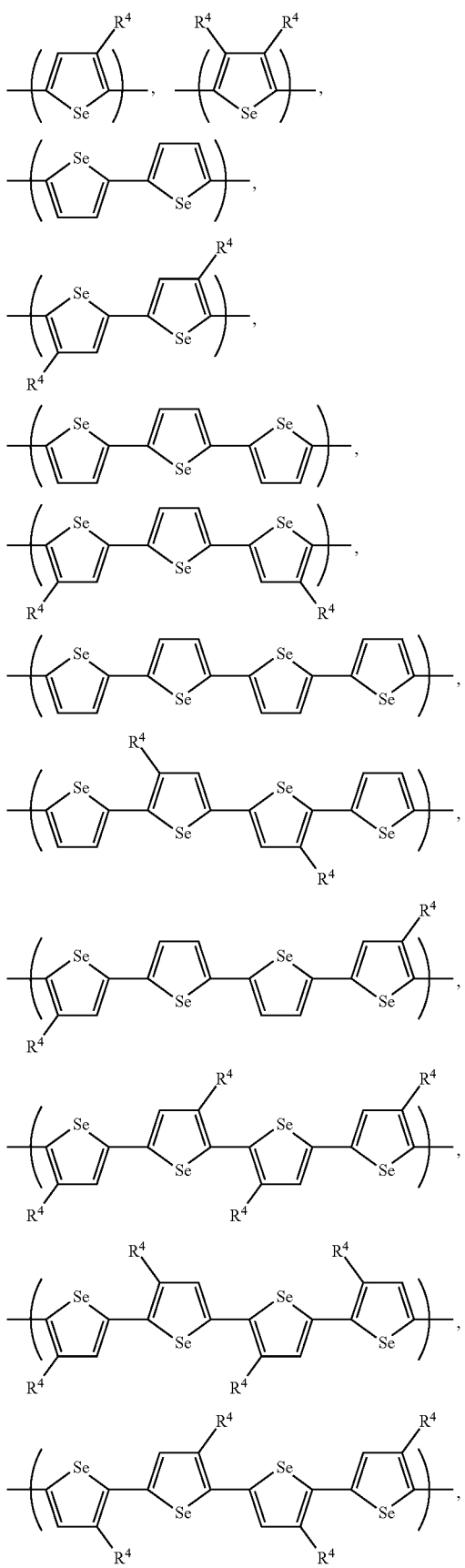
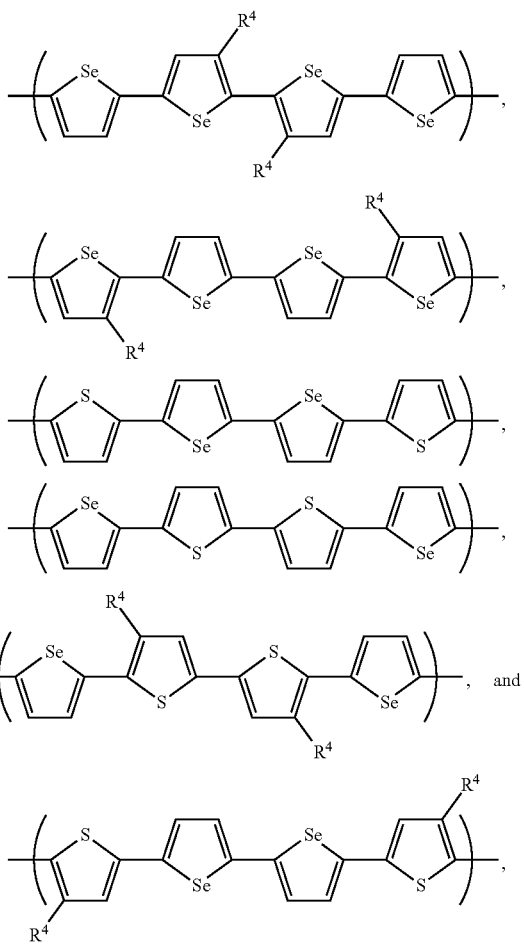
where, for example, each $R^4$ independently is selected from F, Cl, CN, $R^2$, $OR^2$, and $SR^2$, where $R^2$ is a linear or branched $C_{1-40}$ alkyl or haloalkyl group.
In other embodiments, $M_2$ can have the formula:
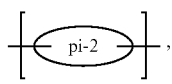
wherein pi-2 can be selected from:
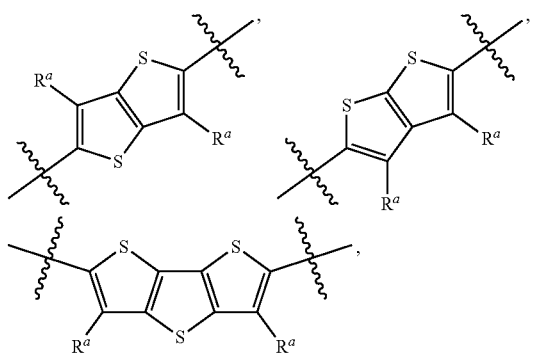

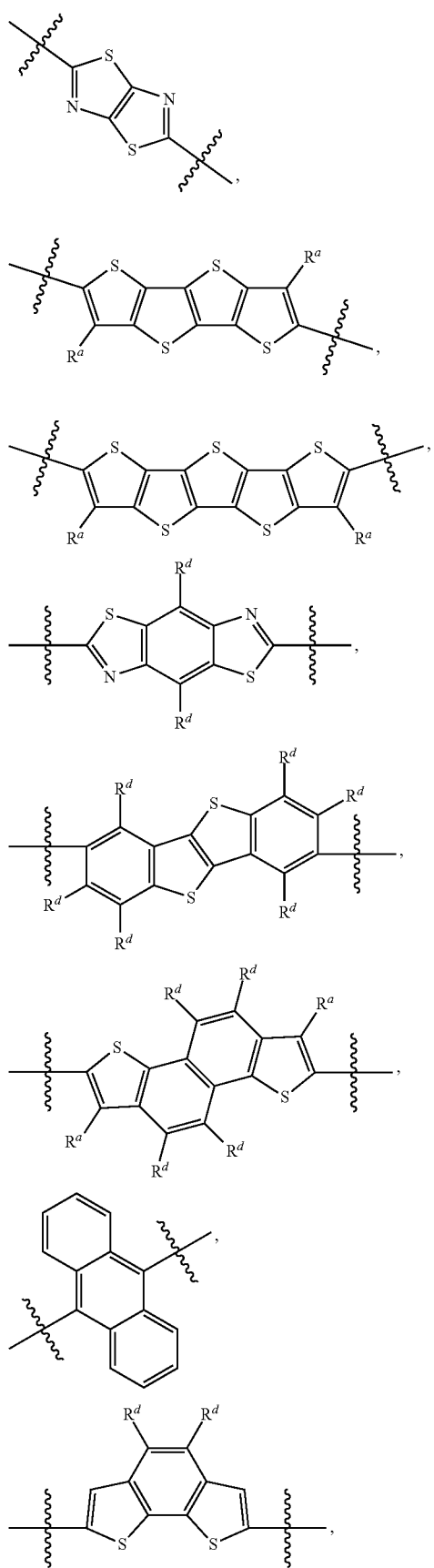
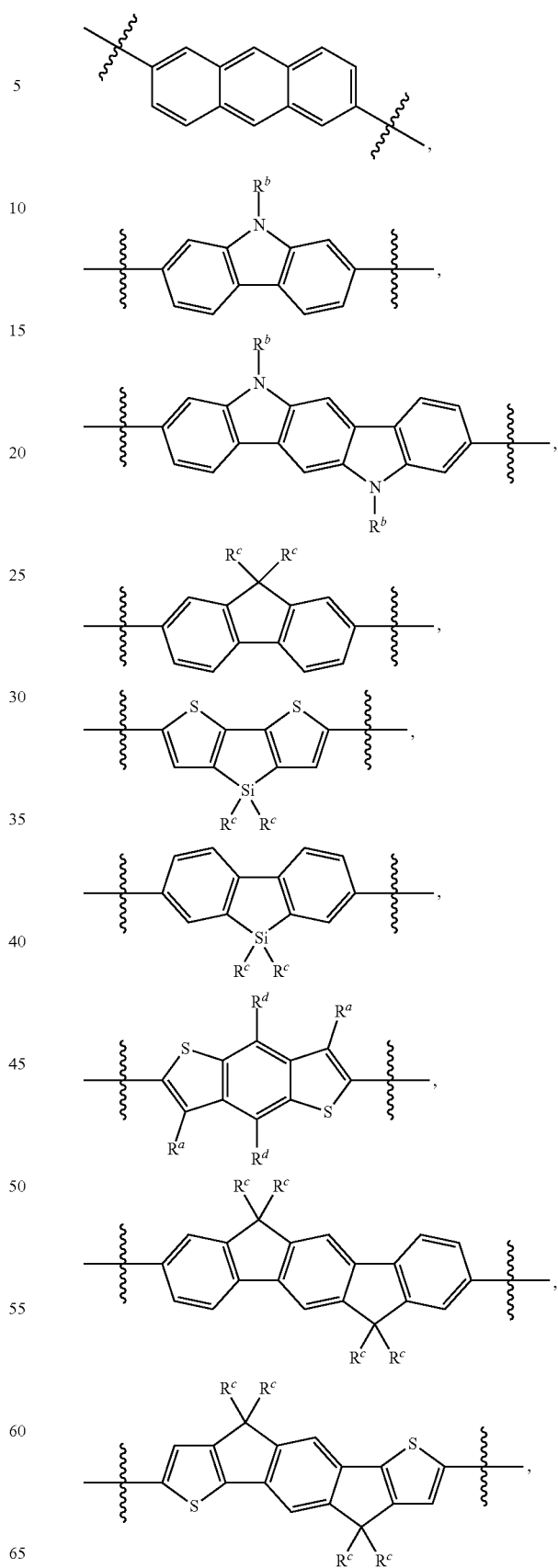

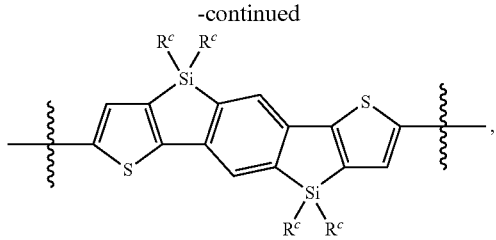
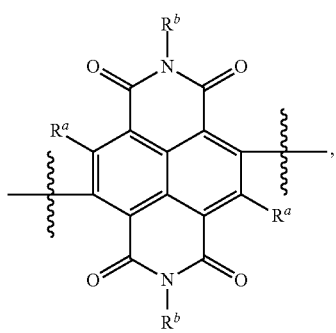
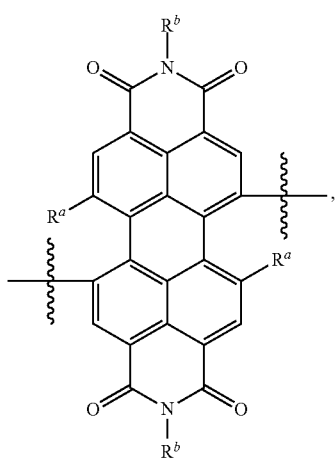
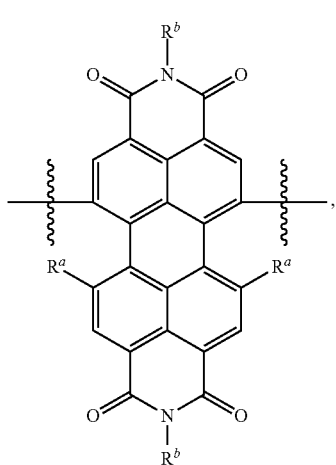
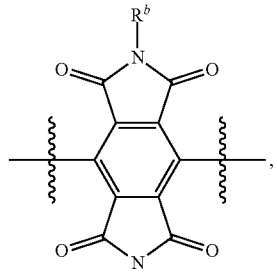
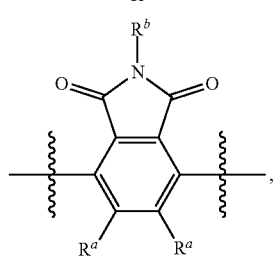
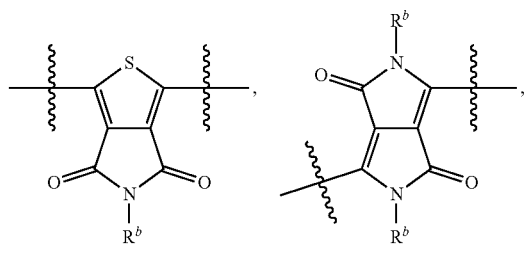
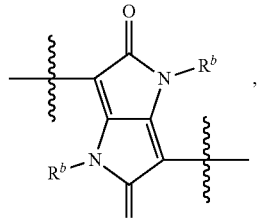
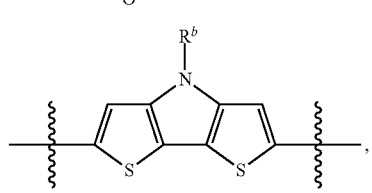
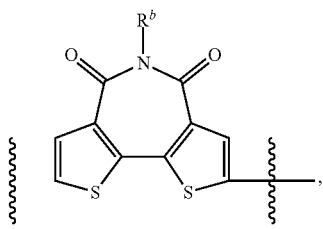
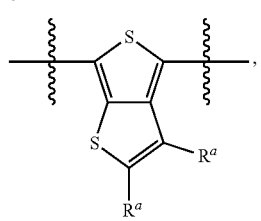

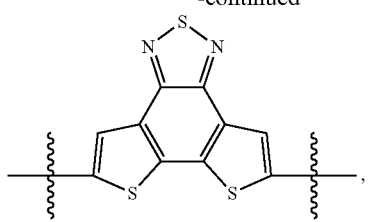
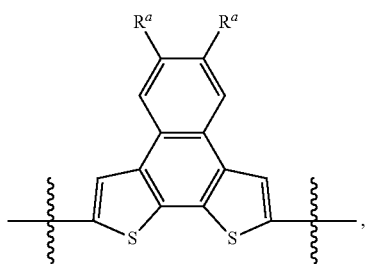
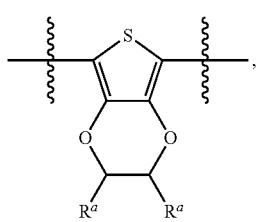
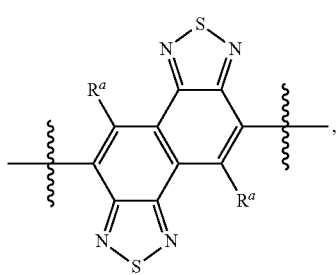
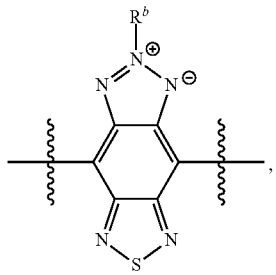
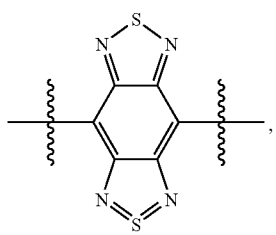
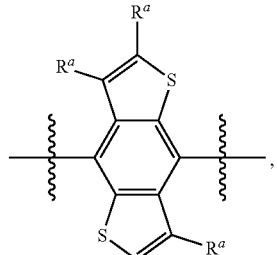
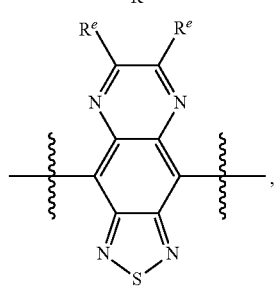
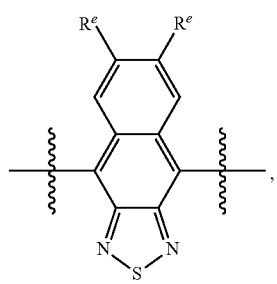
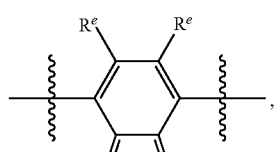
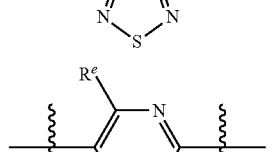
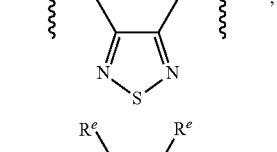
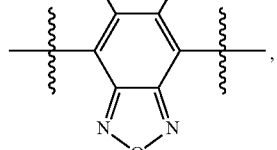
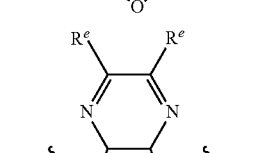
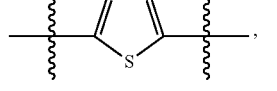, and -continued

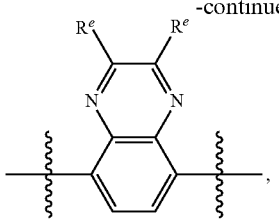

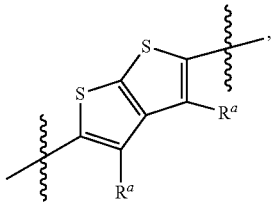

wherein:
$R^a$ is selected from the group consisting of H, F, Cl, —CN, R, —OR, —SR, —C(O)R, —OC(O)R, and —C(O)OR;
$R^b$ is selected from the group consisting of H, R, and -L-$R^f$;
$R^c$ is H or R;
$R^d$ is selected from the group consisting of H, F, Cl, —CN, R, —OR, —SR, —C(O)R, —OC(O)R, —C(O)OR, and -L-$R^f$;
$R^e$ is selected from the group consisting of H, F, Cl, —CN, R, —OR, —SR, —C(O)R, —OC(O)R, —C(O)OR, and $R^f$;
$R^f$ is a $C_{6-20}$ aryl group or a 5-20-membered heteroaryl group, each optionally substituted with 1-8 groups independently selected from the group consisting of F, Cl, —CN, R, —OR, and —SR;
L is selected from the group consisting of —O—, —S—, —C(O)—, —OC(O)—, —C(O)O—, and a covalent bond; and
R is selected from the group consisting of a $C_{1-40}$ alkyl group, a $C_{1-40}$ haloalkyl group, a $C_{2-40}$ alkenyl group, and a $C_{2-40}$ alkynyl group.

In yet other embodiments, $M_2$ can have the formula:

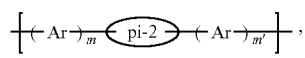

wherein Ar, pi-2, m and m' are as defined herein. Preferably, $(Ar)_m$ and $(Ar)_{m'}$ are selected from:

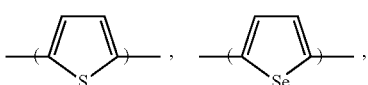

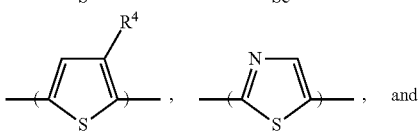

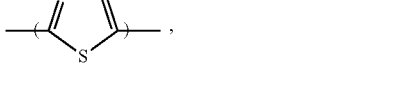

, and where $R^4$ is as defined herein, and pi-2 is selected from:

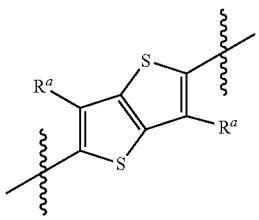

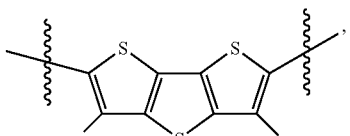

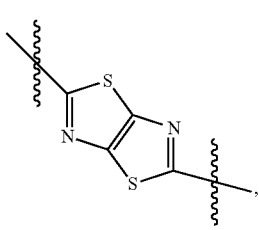

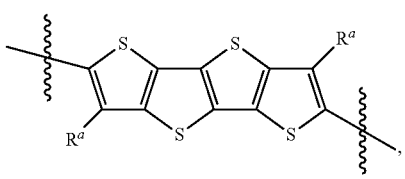

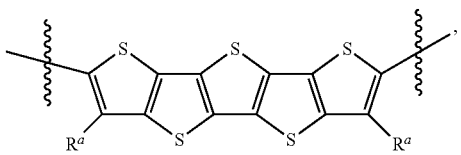

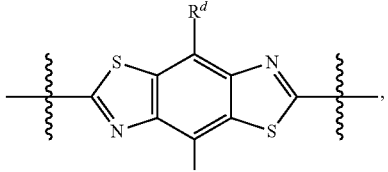

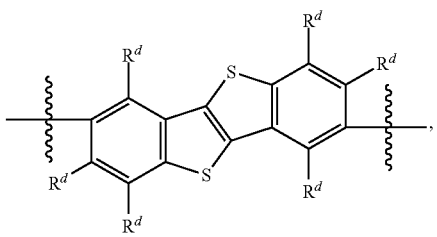

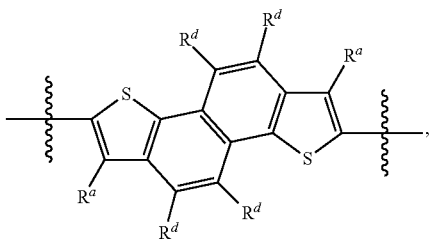

39
-continued
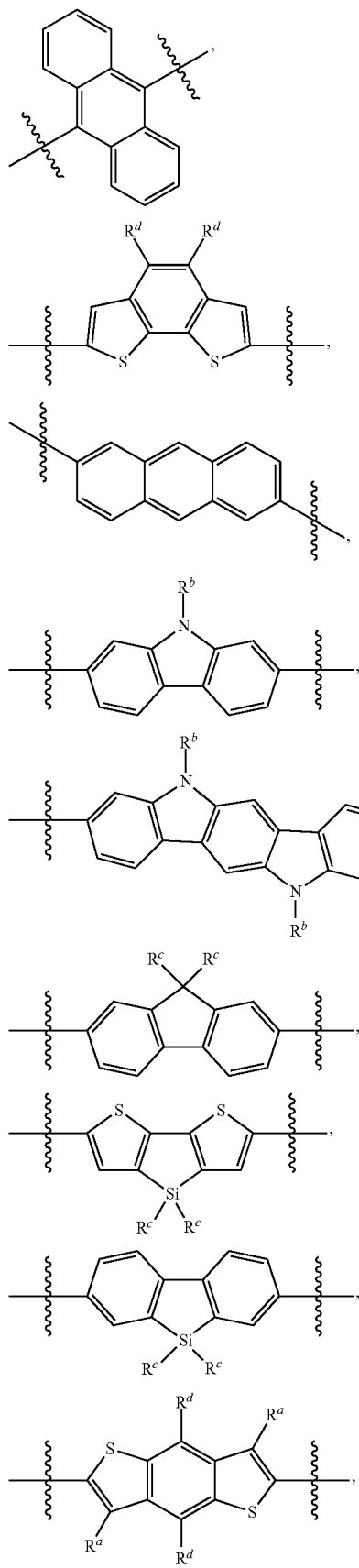
40
-continued
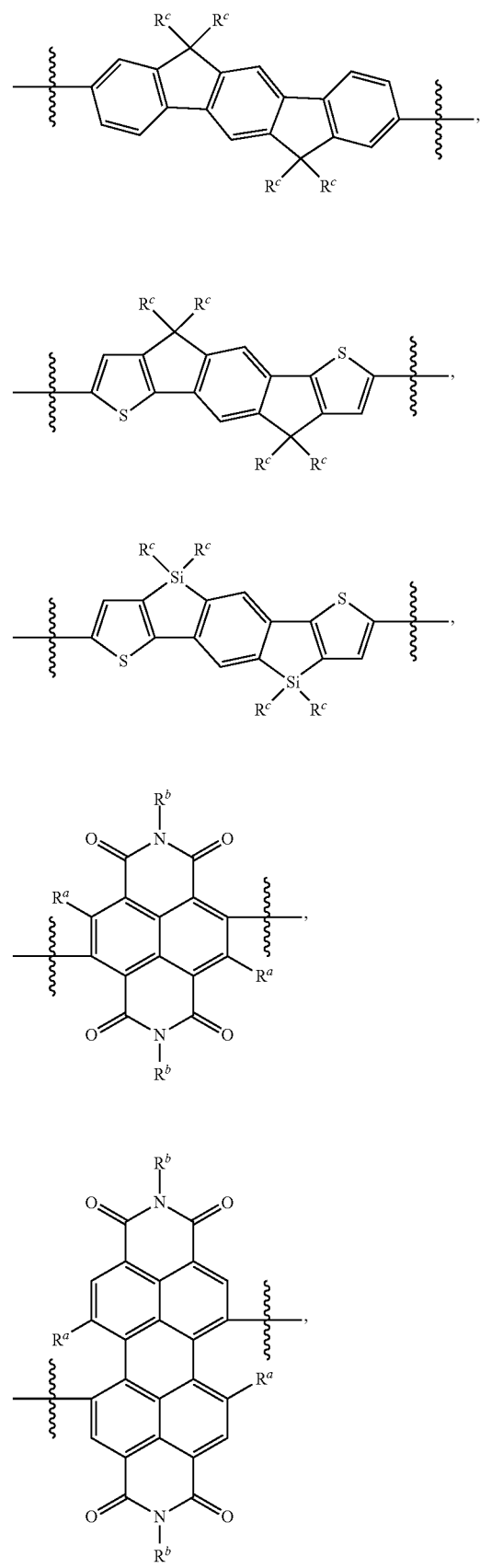

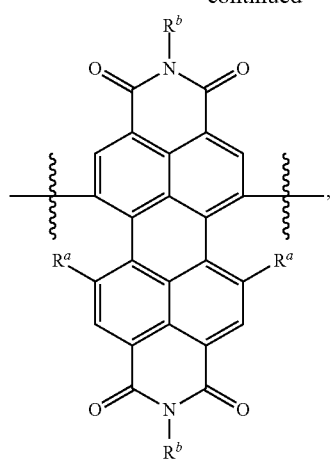
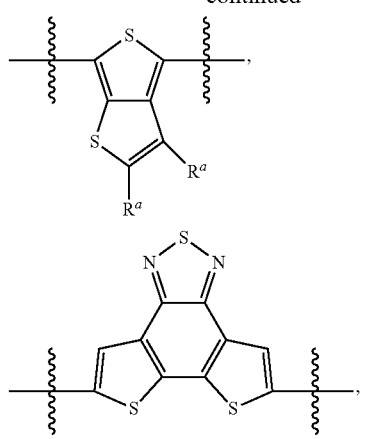
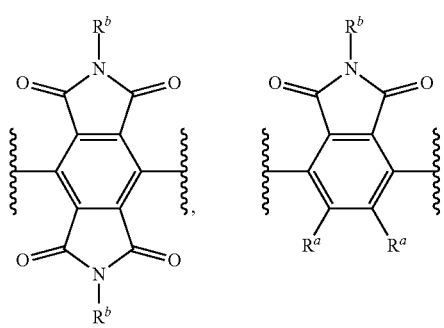
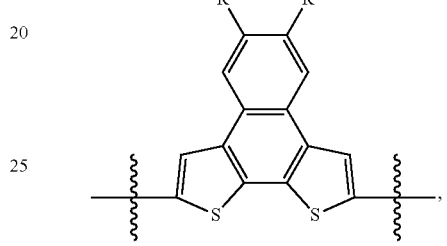
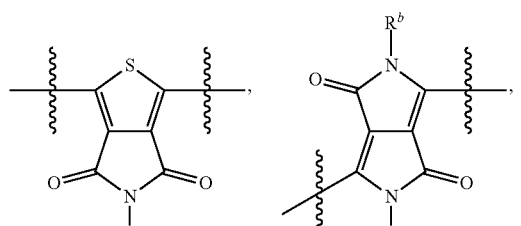
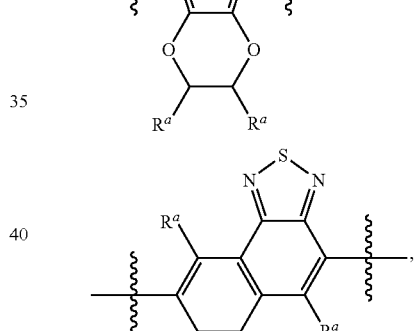
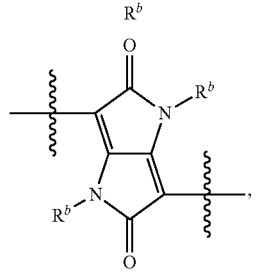
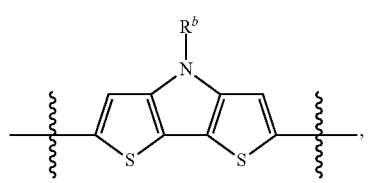
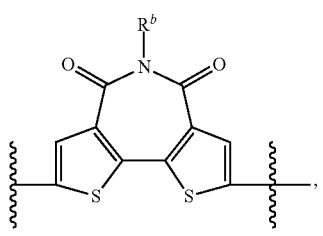
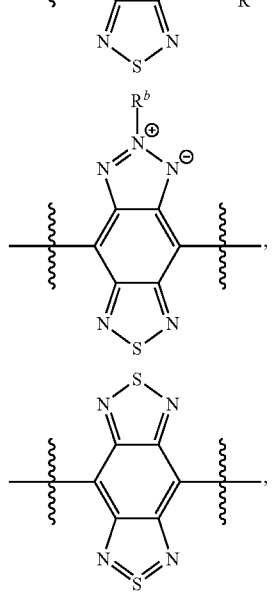

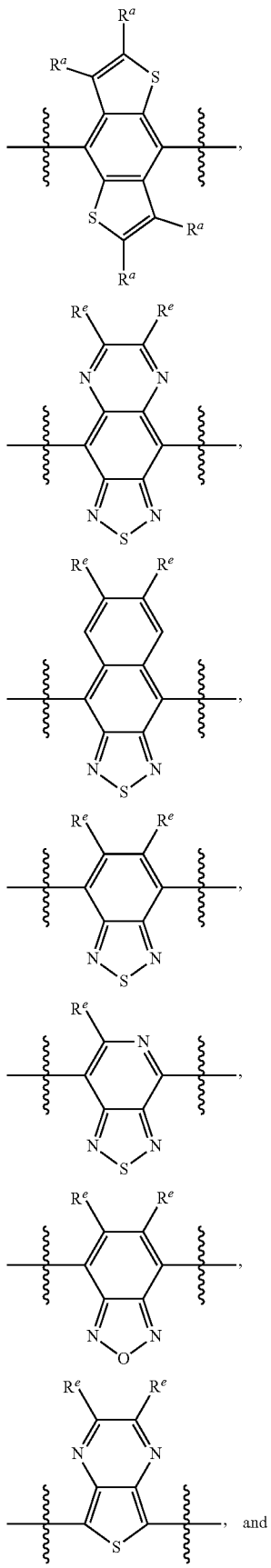

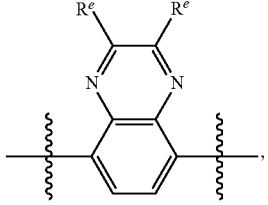

wherein:

$R^a$ is selected from the group consisting of H, F, Cl, —CN, R, —OR, —SR, —C(O)R, —OC(O)R, and —C(O)OR;

$R^b$ is selected from the group consisting of H, R, and -L-$R^f$;

$R^c$ is H or R;

$R^d$ is selected from the group consisting of H, F, Cl, —CN, R, —OR, —SR, —C(O)R, —OC(O)R, —C(O)OR, and -L-$R^f$;

$R^e$ is selected from the group consisting of H, F, Cl, —CN, R, —OR, —SR, —C(O)R, —OC(O)R, —C(O)OR, and $R^f$;

$R^f$ is a $C_{6-20}$ aryl group or a 5-20-membered heteroaryl group, each optionally substituted with 1-8 groups independently selected from the group consisting of F, Cl, —CN, R, —OR, and —SR;

L is selected from the group consisting of —O—, —S—, —C(O)—, —OC(O)—, —C(O)O—, and a covalent bond; and R is selected from the group consisting of a $C_{1-40}$ alkyl group, a $C_{1-40}$ haloalkyl group, a $C_{2-40}$ alkenyl group, and a $C_{2-40}$ alkynyl group.

In other embodiments, $M_2$ can have a formula selected from:

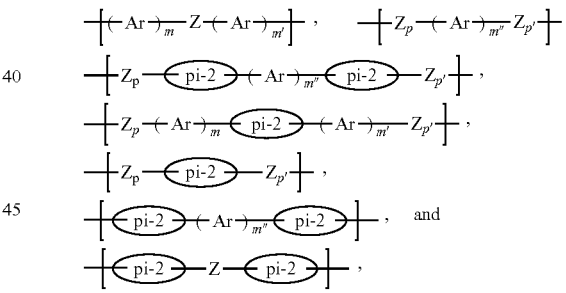

wherein m, m' and m" independently are 1, 2, 3 or 4; and Ar, pi-2 and Z are as defined herein. In such embodiments, $M_2$ can be selected from the group consisting of:

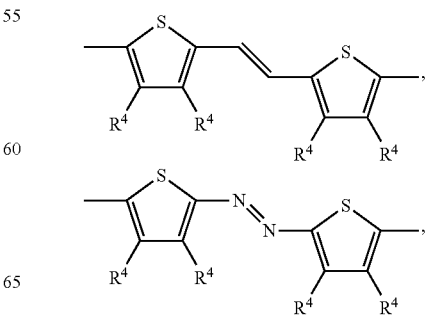

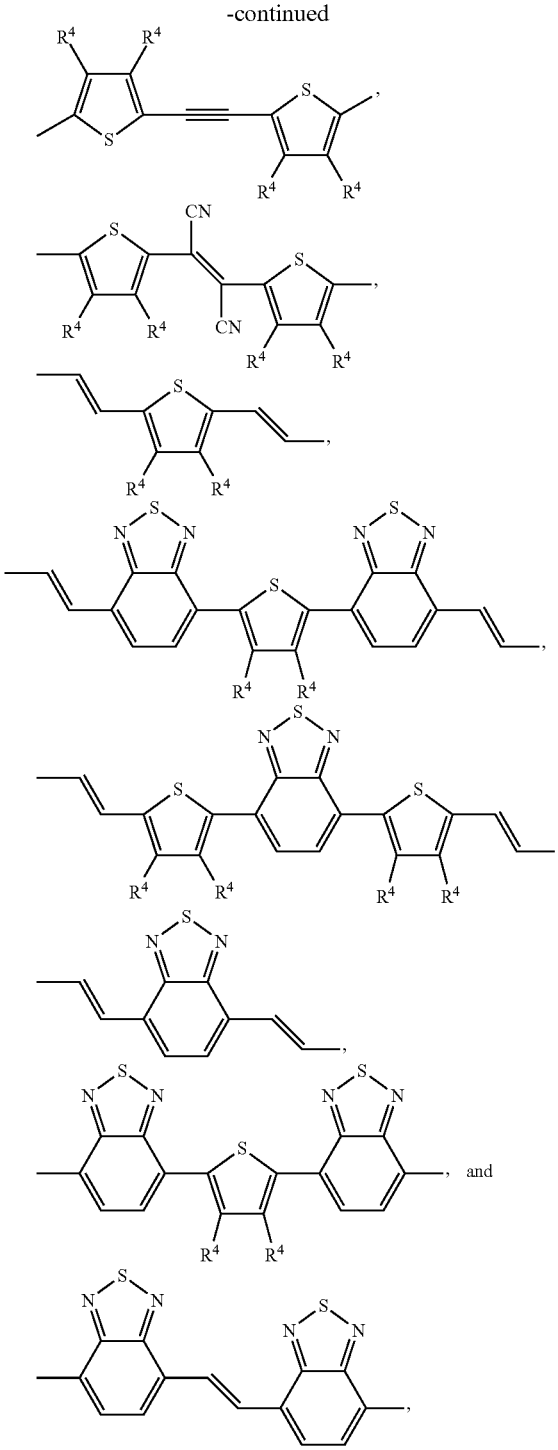

wherein R⁴ is as defined herein.

In preferred embodiments, the present polymers are copolymers of $M_1$ and at least one $M_2$, where $M_2$ is selected from:

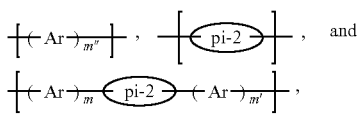

where pi-2, Ar, m, m', and m" are as defined herein.

Certain embodiments of the present copolymers can be represented by a formula selected from the group consisting of:

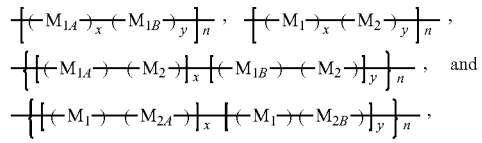

where $M_{1A}$ and $M_{1B}$ represent different repeating units $M_1$, and $M_{2A}$ and $M_{2B}$ represent different repeating units $M_2$, x and y are real numbers representing molar ratios, and n is the degree of polymerization. To illustrate, $M_{1A}$ and $M_{1B}$ can be different units selected from the group consisting of:

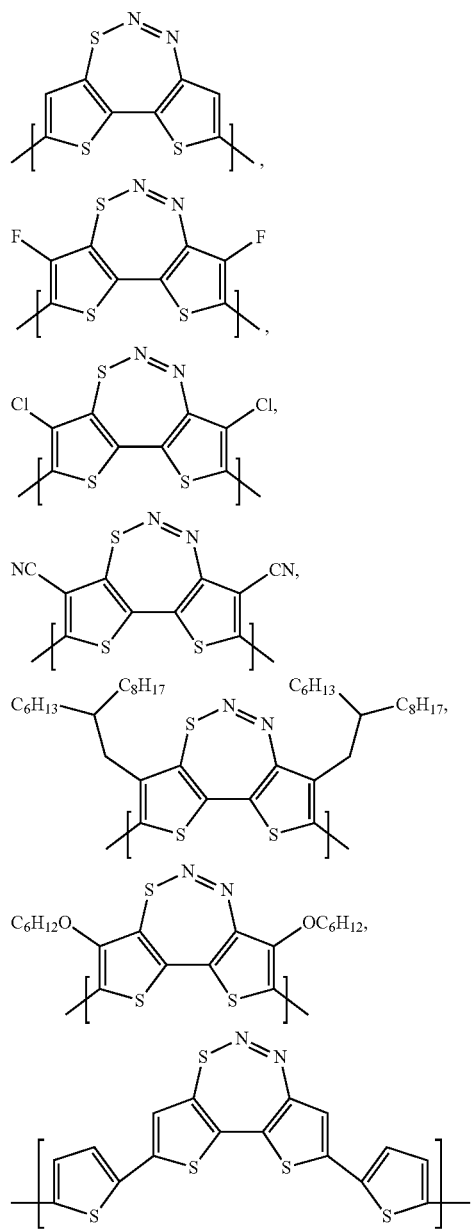

-continued

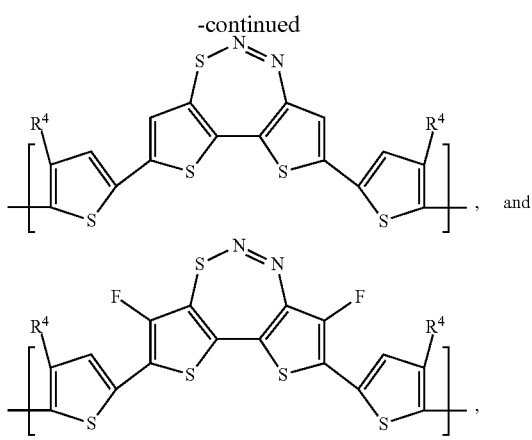
, and where R⁴ can be selected from R², OR², and SR², where R² is a linear or branched $C_{1-40}$ alkyl or haloalkyl group. To illustrate further, $M_{2A}$ and $M_{2B}$ can be:

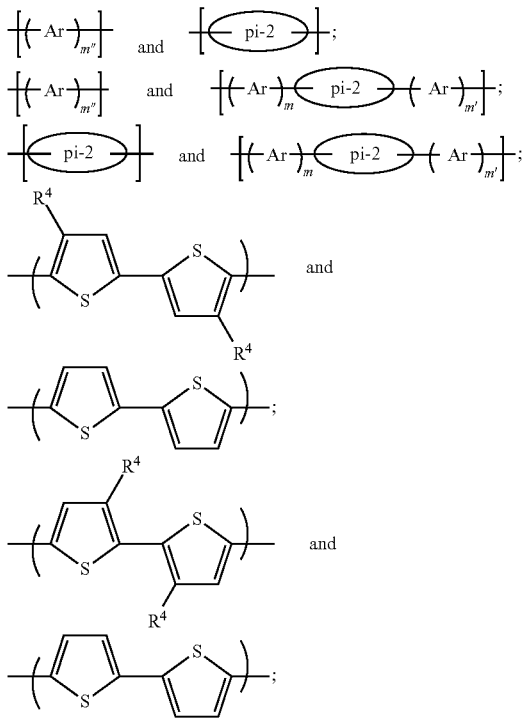

or two repeating units represented by:

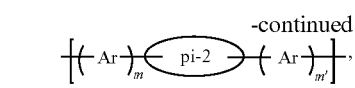

where in $M_{2A}$, Ar is

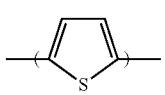

and in $M_{2B}$, Ar is

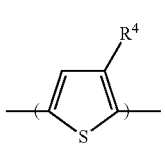

For the various polymers described above, the degree of polymerization (n) can be an integer between 3 and 1,000. In some embodiments, n can be 4-1,000, 5-1,000, 6-1,000, 7-1,000, 8-1,000, 9-1,000, or 10-1,000. For example, n can be 8-500, 8-400, 8-300, or 8-200. In certain embodiments, n can be 8-100. Embodiments of the present compounds including two or more different repeating units can have such repeating units repeating in a random or alternating manner, and the mole fraction of the two units can be between about 0.05 and about 0.95. For example, the respective mole fractions (x and y) of the two units can be between about 0.1 and about 0.9, between about 0.2 and about 0.8, between about 0.3 and about 0.7, between about 0.4 and about 0.6, or between about 0.45 and about 0.55. In certain embodiments, the present polymers can include the same mole fraction of the first unit as the second unit (i.e., x=y=0.5).

In some embodiments, the present compound can be a molecular compound including at least one moiety of formula (I) and a plurality of linear and/or cyclic conjugated moieties, such that the compound as a whole provides a pi-extended conjugated system.

To illustrate, exemplary small-molecule semiconducting compounds including at least one moiety of formula (I), and preferably, where the one or more moieties of formula (I) are represented by formula (II), and monomers for preparing the polymers described herein can be represented by the following formulae:

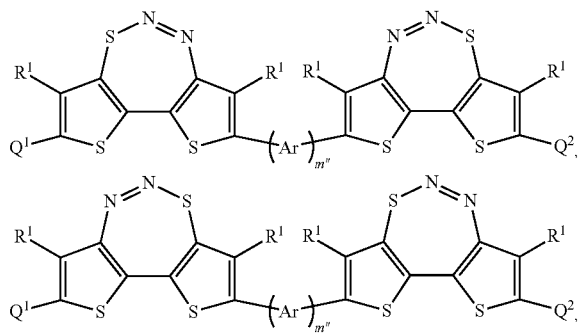

-continued
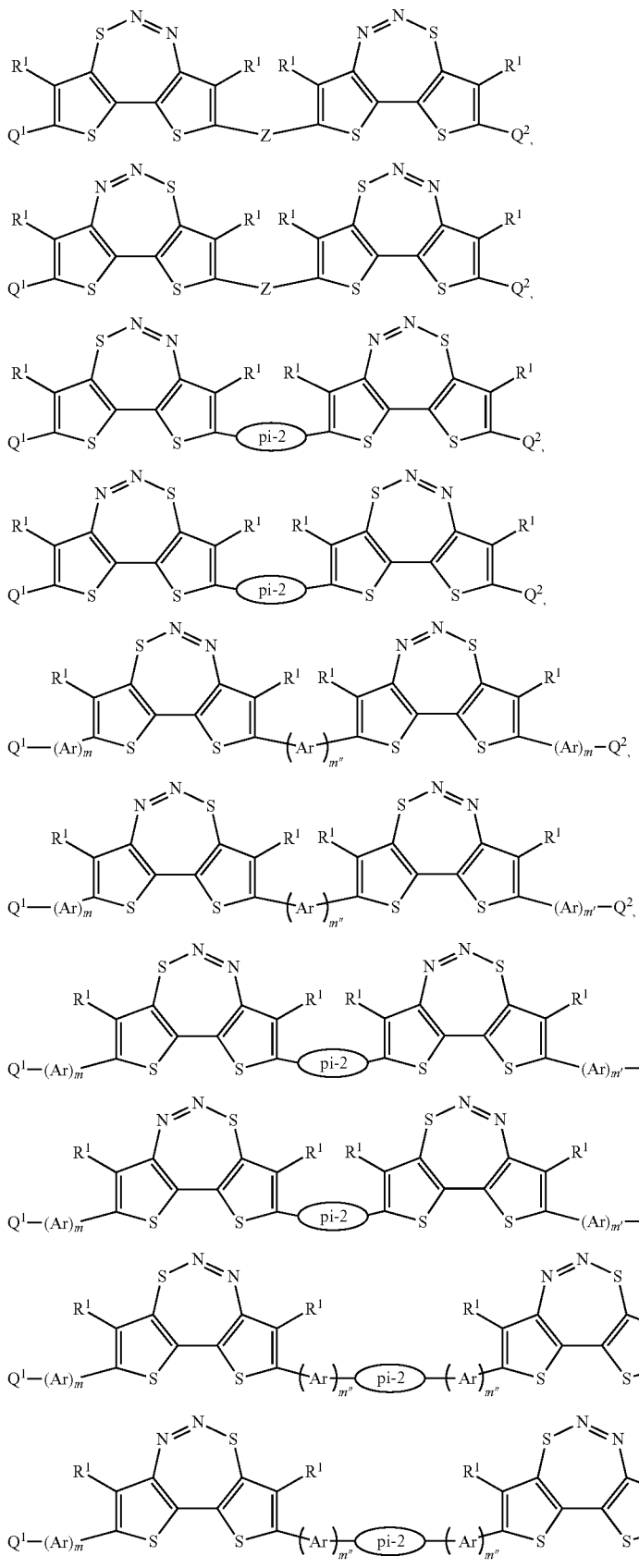

where $Q^1$ can be $X^1$ or $T^1$, $Q^2$ can be $X^2$ or $T^2$, where $X^1$ and $X^2$ can be identical or different reactive groups such as a halide, an organotin group, a boronate, or a polymerizable group, $T^1$ and $T^2$ can be identical or different terminal groups selected from H, $R^2$, and $C(O)R^2$, where $R^2$ is a $C_{1-40}$ alkyl or haloalkyl group, and pi-2, Ar, Z, m, m', m", p, and p' are as defined herein.

Certain embodiments of molecular semiconducting compounds according to the present teachings can be represented by a formula selected from the group consisting of:

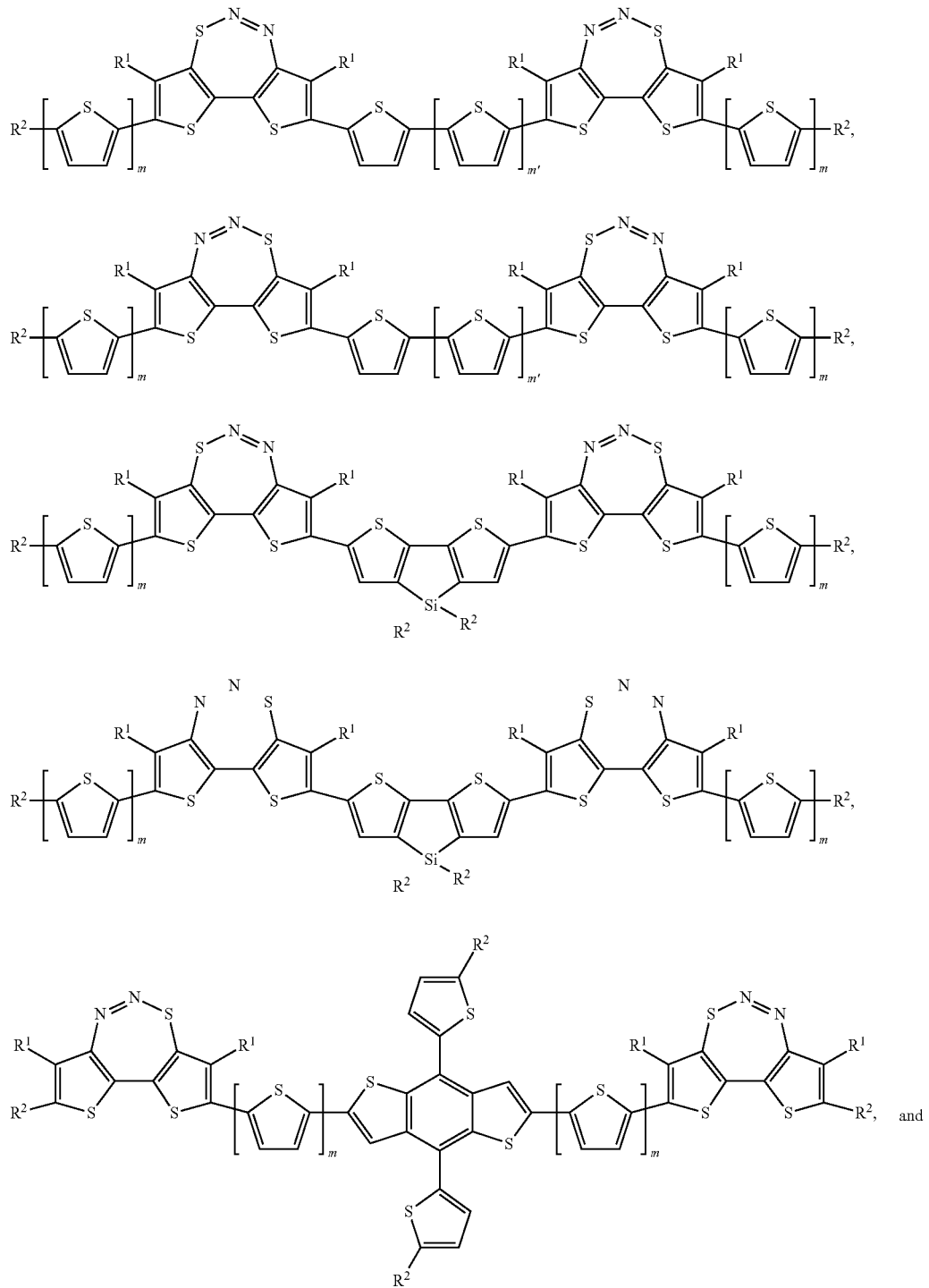

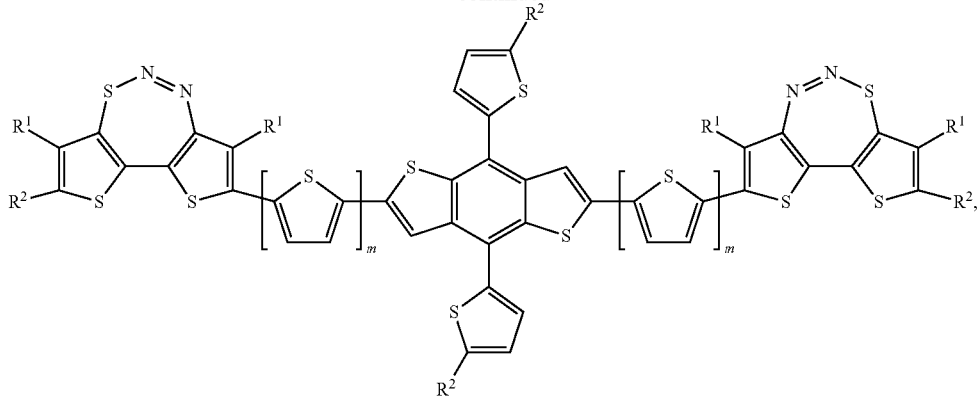

where R¹, R², m and m' are as defined herein.

Specific exemplary molecular semiconducting compounds according to the present teachings include:

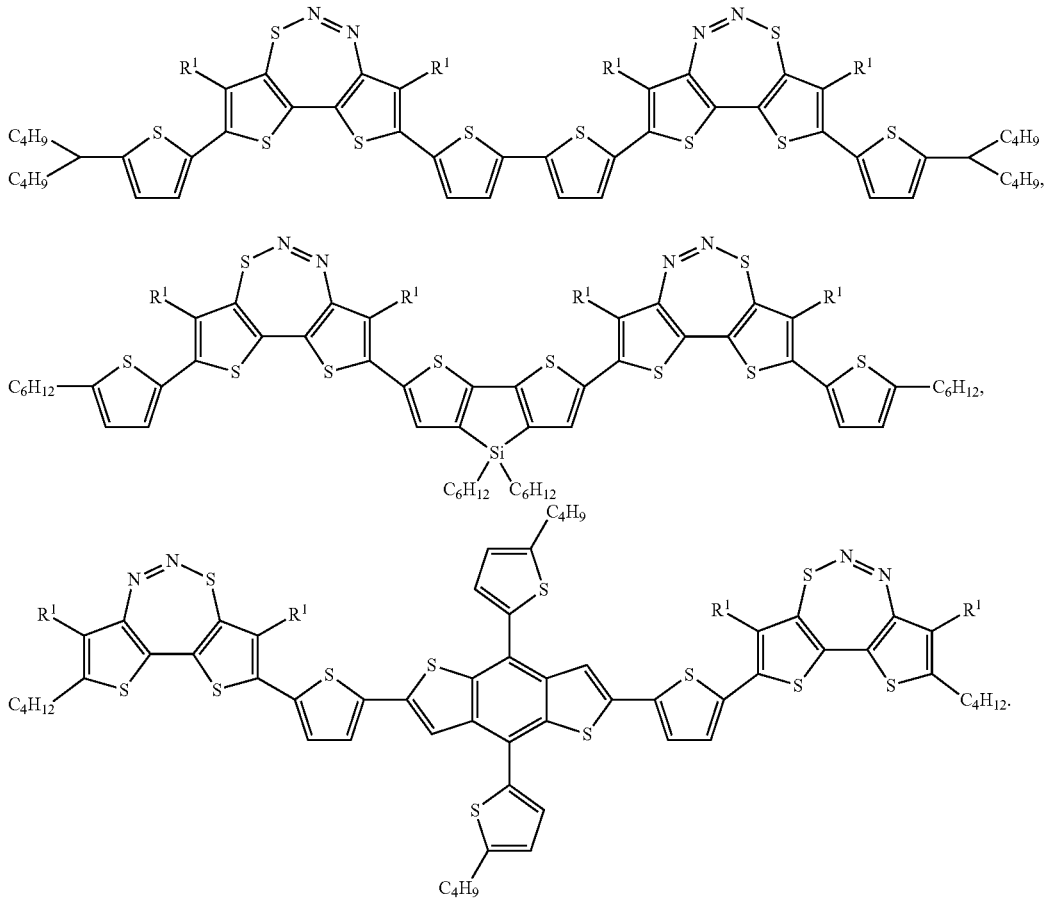

Specific exemplary molecular semiconducting compounds according to the present teachings and monomers including moieties of formula (I) can be prepared using the synthetic routes described hereinbelow. Other monomers according to the present teachings can be commercially available, known in the literature, or can be prepared from readily prepared intermediates by employing standard synthetic methods and procedures known to those skilled in the art. Standard synthetic methods and procedures for the preparation of organic molecules and functional group transformations and manipulations can be readily obtained from the relevant scientific literature or from standard textbooks in the field.

To illustrate, unsubstituted dithieno[1,2,3]thiadiazoles can be synthesized via diazotation (the formation of a diazonium compound) followed by ring closure, e.g.,

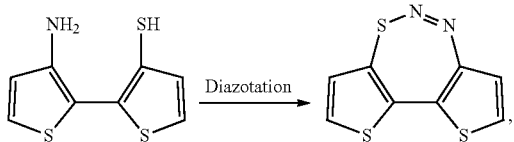 [SMILES: Nc1ccsc1-c1sccc1S ; c1cc2c(s1)-c1sccc1SN=N2]

according, but not limited, to the synthetic routes described in the literature for benzenoid[1,2,3]thiadiazoles. See e.g., Trusova, M. E. et al., *Synthesis*, 13: 2154-2158 (2011); Ward, E. R. et al., *J. Chem. Soc.*, 2374-2379 (1962); and Hünig, S. et al., *Justus Liebigs Annalen der Chemie*, 738: 192-194 (1970).

Other methodologies can be summarized below:

Alkyl-substituted dithieno[1,2,3]thiadiazoles can be synthesized according to the methodology below:

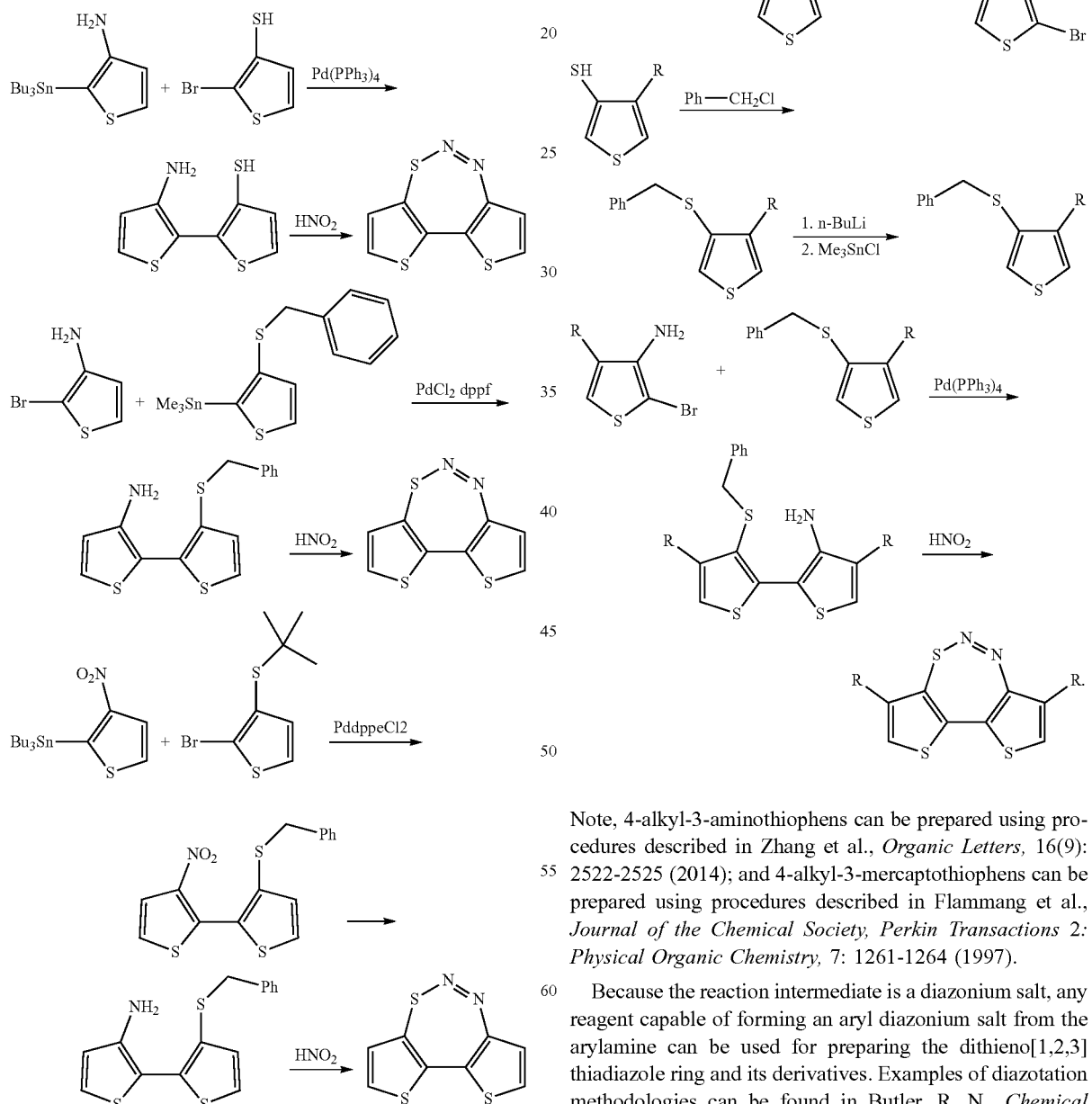

Note, 4-alkyl-3-aminothiophens can be prepared using procedures described in Zhang et al., *Organic Letters*, 16(9): 2522-2525 (2014); and 4-alkyl-3-mercaptothiophens can be prepared using procedures described in Flammang et al., *Journal of the Chemical Society, Perkin Transactions 2: Physical Organic Chemistry*, 7: 1261-1264 (1997).

Because the reaction intermediate is a diazonium salt, any reagent capable of forming an aryl diazonium salt from the arylamine can be used for preparing the dithieno[1,2,3]thiadiazole ring and its derivatives. Examples of diazotation methodologies can be found in Butler, R. N., *Chemical Reviews*, 75(2): 241-257 (1975); and in O'Leary, P., *Sci. Synth.*, 31b, 1361-1400 (2007).

The following compounds are known in the literature or can be synthesized as indicated below:

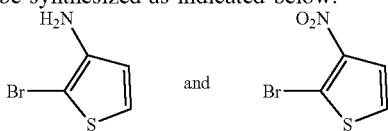

are commercially available;

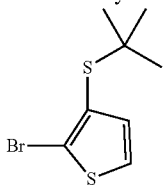

can be synthesized using the procedures described in Gol'dfarb et al., *Izvestiya Akademii Nauk SSSR, Seriya Khimicheskaya*, 10: 2290-5 (1973);

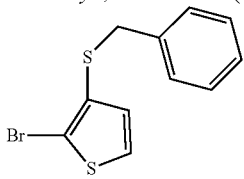

can be synthesized using the procedures described in Kellogg et al., *Journal of Organic Chemistry*, 33(7): 2902-9 (1968);

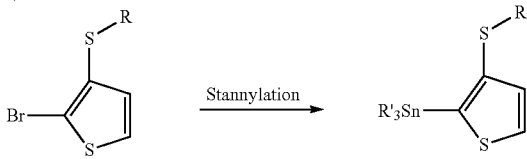

can be performed as described in Barbarella et al., *Tetrahedron* 53(27): 9401-9406 (1997);

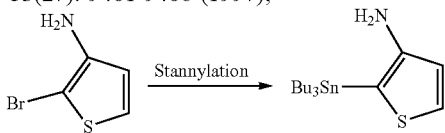

can be performed using analogous procedures as described in Sabbatini et al., *Journal of Medicinal Chemistry*, 53(17): 6506-6510 (2010);

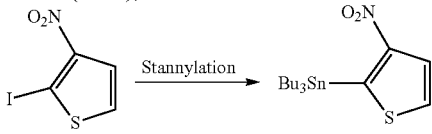

can be performed using analogous procedures as described in Qiu et al., *Angewandte Chemie, International Edition*, 52(44): 11581-11584, or Al-Allaf et al., *Journal of Organometallic Chemistry*, 373(1): 29-35 (1989);

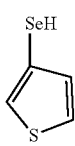

can be prepared using procedures described in Mahatsekake et al., *Sulfur Letters*, 7(6): 231-8 (1988);

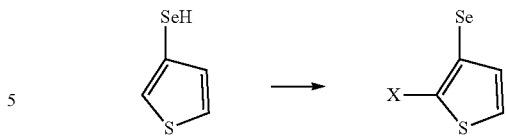

can be performed using procedures described in Ishii et al., *Heteroatom Chemistry*, 25(6): 658-673 (2014);

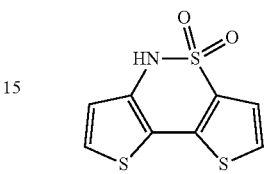

can be prepared using procedures described in U.S. patent application Ser. No. 14/951,628.

The unsubstituted dithieno[1,2,3]thiadiazoles then can be halogenated or otherwise provided with reactive groups (Q) to enable coupling with the various Sp groups (Ar, Z, and/or pi-2) described herein. For example, monohalogenated dithieno[1,2,3]thiadiazole derivatives can be useful synthones for the synthesis of dithieno[1,2,3]thiadiazole-based small-molecule semiconductors or regioregular polymers.

To illustrate, dithieno[1,2,3]thiadiazoles can be brominated to provide monobrominated or dibrominated derivatives, which in turn can be used to couple with other dithieno[1,2,3]thiadiazoles and/or different conjugated moieties having complementary reactive groups to provide various molecular and polymeric semiconductors according to the present teachings.

For example, monobrominated dithieno[1,2,3]thiadiazoles can be synthesized from the corresponding precursors using conventional bromination protocols where a stoichiometric amount of halogen is employed to optimize monobromination:

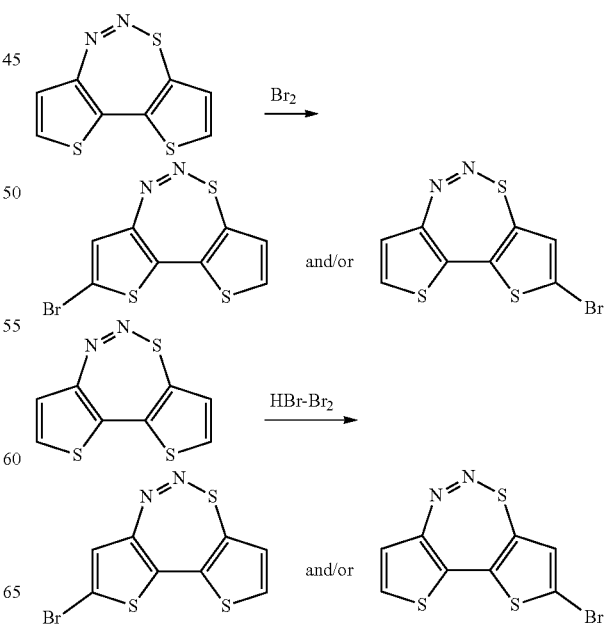

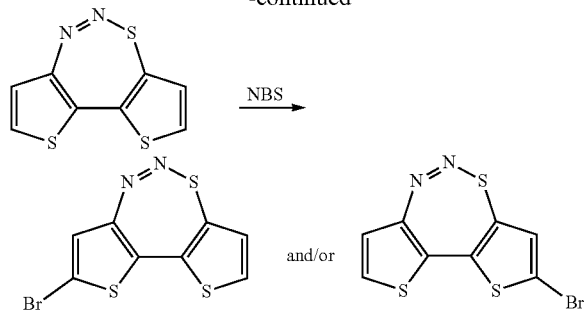

Additionally, because two isomers can form, the ratio of the two compounds can be controlled by changing the experimental conditions such as temperature, time, concentration, solvent, and brominating reagent.

An alternative route to monobrominated dithieno[1,2,3]thiadiazoles is to start with monobrominated derivatives and build the thiadiazole ring via diazotation:

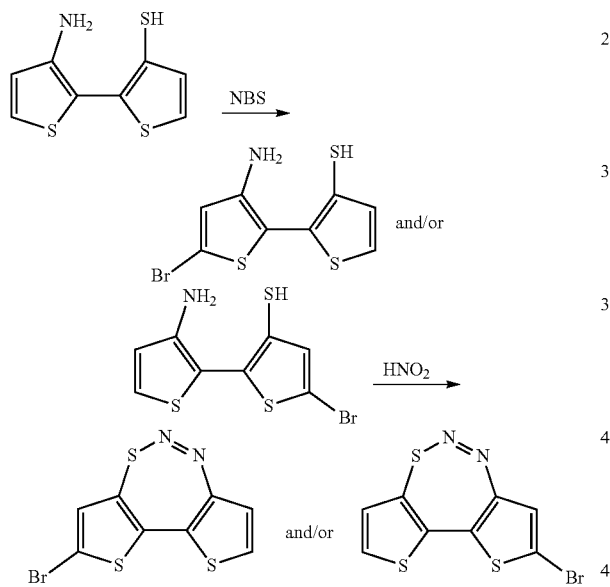

From these monobrominated dithieno[1,2,3]thiadiazole derivatives, dimeric compounds including two moieties of formula (I) and one or more linear and/or cyclic conjugated moieties (represented by $M_2$ below) can be synthesized as follows:

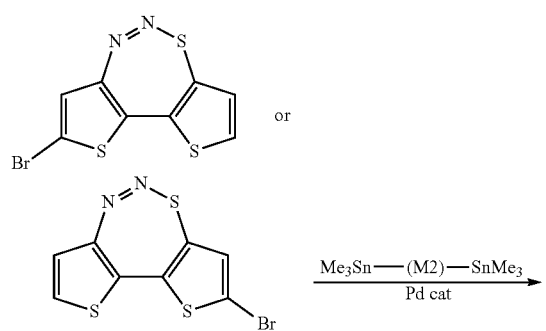

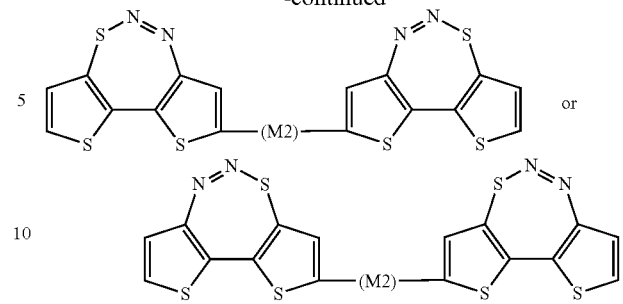

Dibromodithieno[1,2,3]thiadiazoles can be synthesized from the corresponding precursors using conventional bromination protocols where two times the stoichiometric amount of halogen is employed to optimize dibromination, e.g.,

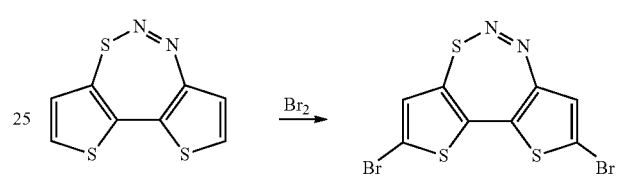

Similar to the monobrominated version, it is also possible to start with dibrominated dithiophene aminothiols and build the thiadiazole ring via diazotation:

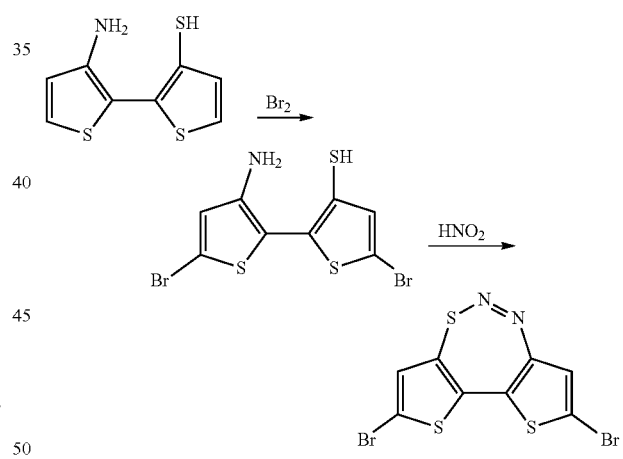

For embodiments where the present compound is a polymer having the $M_1$ unit:

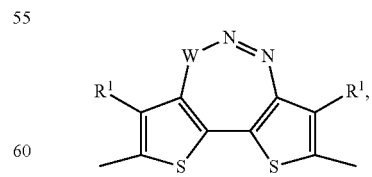

dithieno[1,2,3]thiadiazoles that are brominated or otherwise derivatized with reactive groups can serve as a key building block.

Other polymerizable derivatives of dithieno[1,2,3]thiadiazole include distannylated dithieno[1,2,3]thiadiazoles and diborylated dithieno[1,2,3]thiadiazoles. Distannylated dithieno[1,2,3]thiadiazole derivatives can be synthesized according to the scheme below:

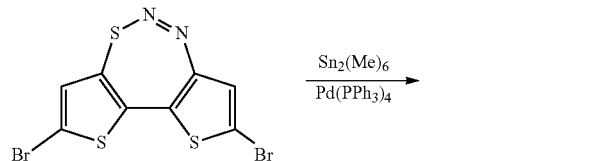

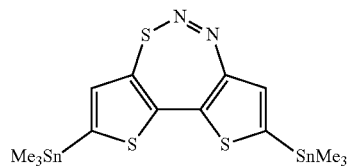

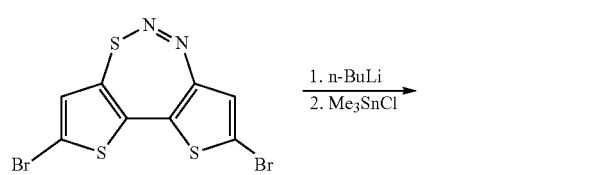

Conditions for catalytic stannylation are known by those skilled in the art. See e.g., Woo, C. H. et al., *JACS*, 130(48): 16324-16329 (2008). Diborylated dithieno[1,2,3]thiadiazole derivatives can be synthesized according to the scheme below:

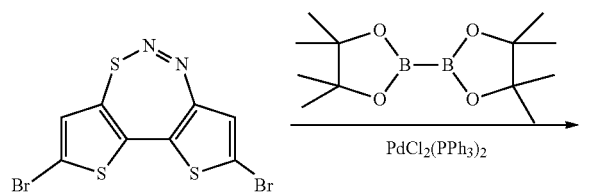

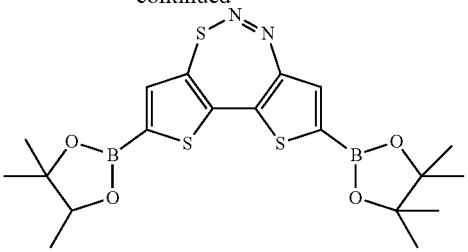

Conditions for catalytic borylation are known by those skilled in the art. See e.g., Zhao, Y. et al., *Tetrahedron*, 68(44): 9113-9118 (2012).

The brominated or metallated dithieno[1,2,3]thiadiazole derivatives then can be used as an $M_1$ unit for copolymerization with an $M_2$ unit having complementary reactive groups. Or, the brominated or metallated dithieno[1,2,3]thiadiazole can be reacted with one or more Sp groups having complementary reactive groups to provide a pi-extended semiconducting compound. Suitable complementary reactive groups used in various coupling or polymerization reactions are well known in the art. In particular, Stille coupling or Suzuki coupling reactions can be used as described in Yamamoto, *J. Organomet. Chem.*, 653: 195-199 (2002); Walton et al., *Polymer Chemistry* (Fred J. Davis ed. 2004), p. 158-187; and Galbrecht et al., *Macromolecular Rapid Communications*, 28(4): 387-394 (2007).

The homopolymerization of $M_1$ and the copolymerization of $M_1$ and $M_2$ can be achieved via various reactions known to those skilled in the art, including procedures analogous to those described in Yamamoto, *J. Organomet. Chem.*, 653: 195-199 (2002); Walton et al., *Polymer Chemistry* (Fred J. Davis ed. 2004), p. 158-187; and Galbrecht et al., *Macromolecular Rapid Communications*, 28(4): 387-394 (200), the entire disclosure of each of which is incorporated by reference herein for all purposes. In particular, Stille coupling or Suzuki coupling reactions can be used to prepare polymeric compounds according to the present teachings with high molecular weights and in high yields (≥75%) and purity, as confirmed by $^1$H NMR spectra, elemental analysis, and/or GPC measurements. The scheme below outlines several exemplary reactions that can be used to polymerize $M_1$ by itself or copolymerize $M_1$ with $M_2$. It should be understood that the polymerizable groups (e.g., $SnR_3$, $BR_2$, MgX, ZnX, and Br, where X is a halogen and R is an alkyl group) can be reversed between $M_1$ and $M_2$. Analogous reactions can be used to couple a moiety of formula (I) with Ar, pi-2, and/or Z moieties to provide a repeating unit $M_1$ including such Ar, pi-2, and/or Z moieties in addition to the moiety of formula (I).

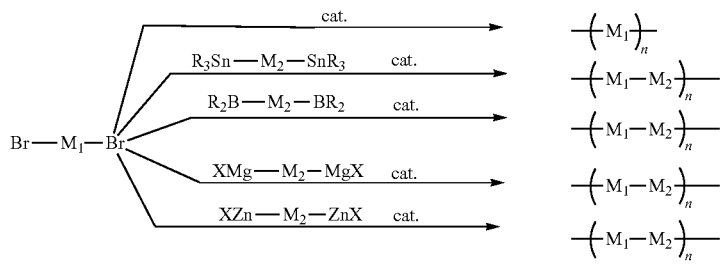

The schemes immediately below illustrate the coupling of a dibrominated dithieno[1,2,3]thiadiazole derivative with a dimetallated derivative of a pi-2 moiety:

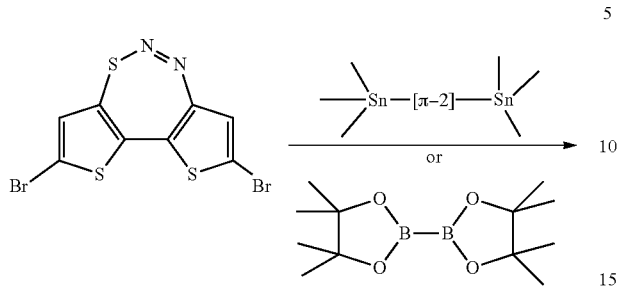

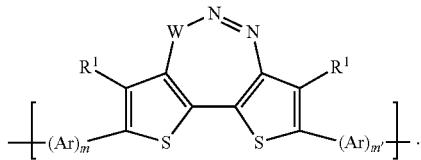

The reactions described above can be used analogously to couple a dibrominated dithieno[1,2,3]thiadiazole derivative to an Sp group having complementary reactive groups to provide a more extended $M_1$ unit such as:

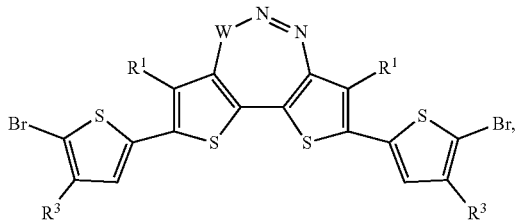

For example, a dibrominated dithieno[1,2,3]thiadiazole derivative can be coupled to two $R^3$-substituted thienyl groups to provide the monomer:

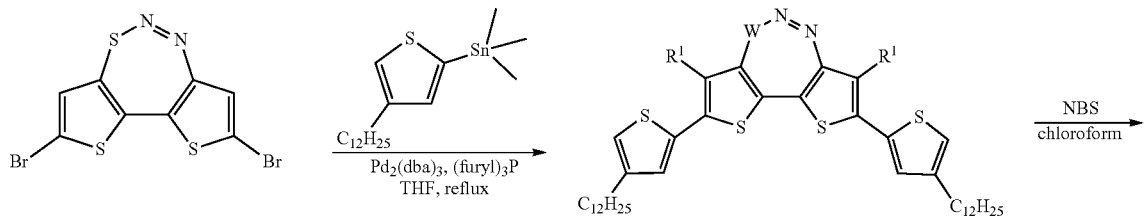

which then can be used to copolymerize with a repeating unit pi-2 as shown below, where $R^3$ is a $C_{12}$ alkyl group:

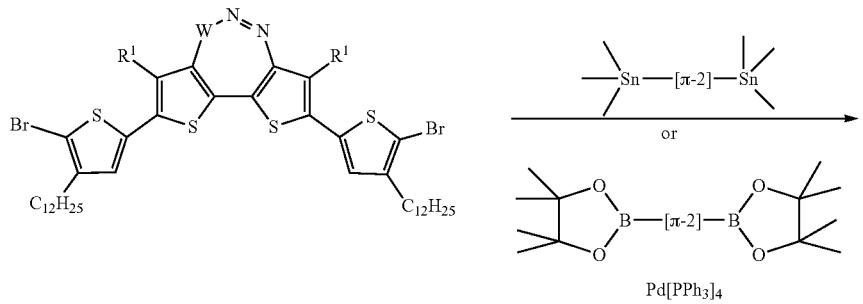

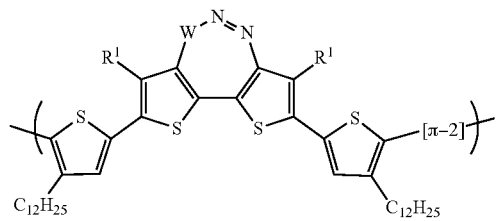

The schemes below illustrate yet further possible syntheses for additional polymers according to the present teachings:

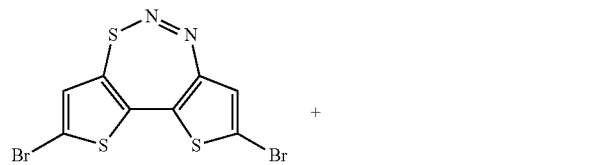

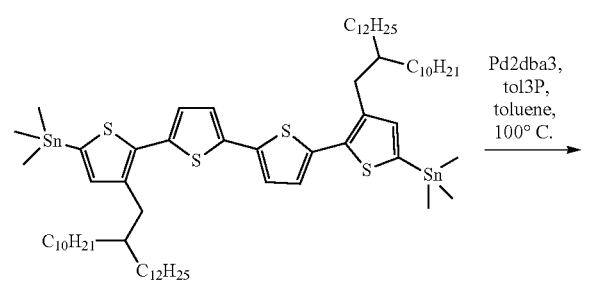

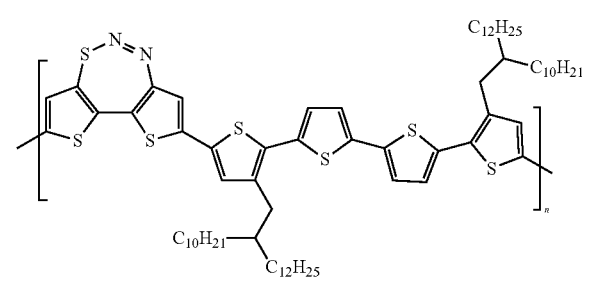

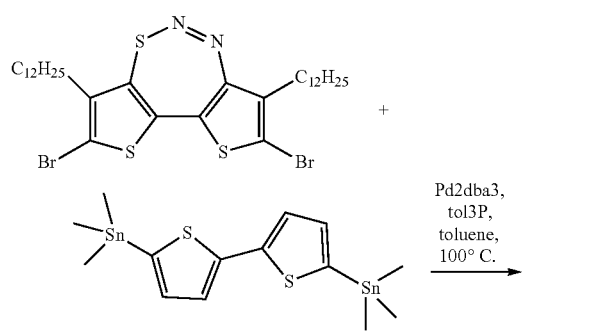

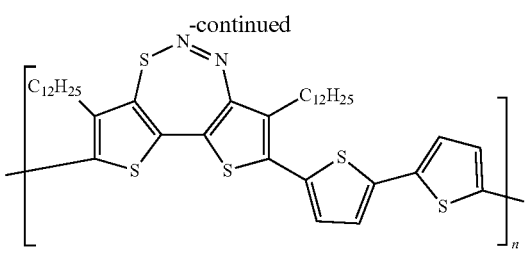

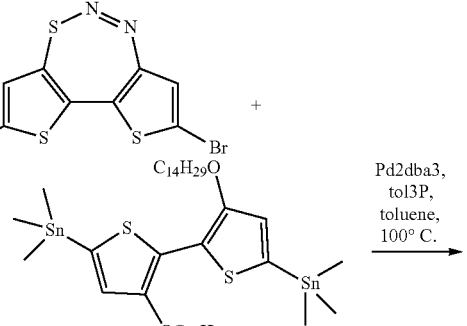

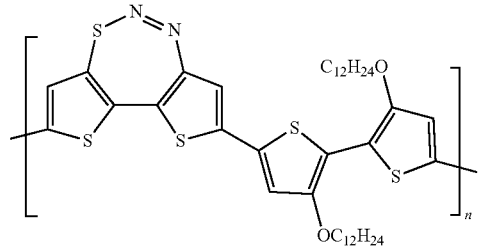

Without wishing to be bound by any particular theory, it is believed that polymers of the present teachings that have a regioregular polymeric backbone can lead to higher molecular weights, a more π-conjugated structure and, consequently better charge transport efficiencies. Accordingly, in preparing the present polymers, the present teachings can include isolating a particular average molecular weight fractions, and/or enriching and/or isolating a particular stereoisomer of $M_1$ and/or $M_2$ that has two or more stereoisomers.

Using coupling reactions analogous to those described above in connection with the preparation of the present polymers, various molecular semiconducting compounds according to the present teachings can be prepared by reacting different mono- or di-halogenated/metallated derivatives of dithieno[1,2,3]thiadiazoles and spacer groups as illustrated below:

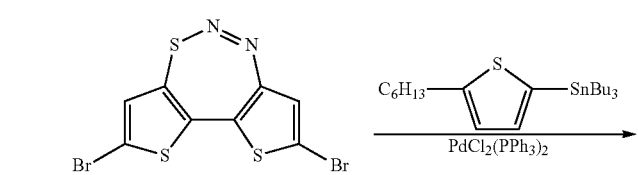

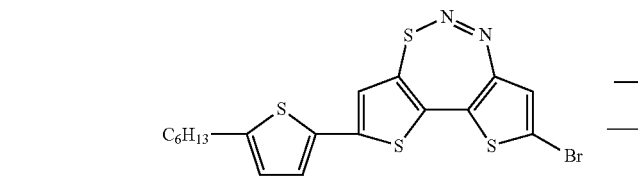

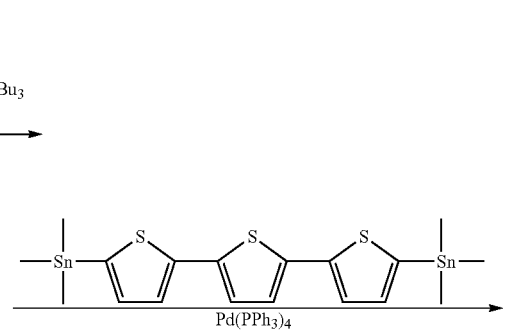

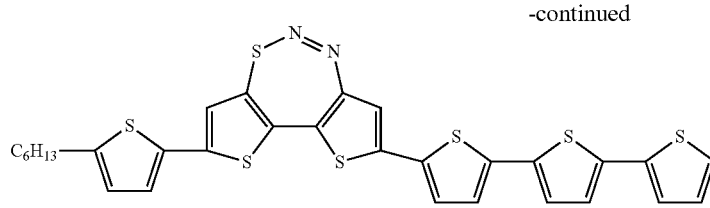
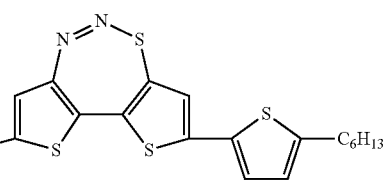

The semiconducting compounds disclosed herein can be stable in ambient conditions ("ambient stable") and soluble in common solvents. As used herein, a compound can be considered electrically "ambient stable" or "stable at ambient conditions" when the carrier mobility or the reduction-potential of the compound is maintained at about its initial measurement when the compound is exposed to ambient conditions, for example, air, ambient temperature, and humidity, over a period of time. For example, a compound according to the present teachings can be described as ambient stable if its carrier mobility or redox potential does not vary more than 20% or more than 10% from its initial value after exposure to ambient conditions, including, air, humidity and temperature, over a 3 day, 5 day, or 10 day period. In addition, a compound can be considered ambient stable if the optical absorption of the corresponding film does not vary more than 20% (preferably, does not vary more than 10%) from its initial value after exposure to ambient conditions, including air, humidity and temperature, over a 3 day, 5 day, or 10 day period.

OTFTs based on the present compounds can have long-term operability and continued high-performance in ambient conditions. For example, OTFTs based on certain embodiments of the present compounds can maintain satisfactory device performance in highly humid environment. Certain embodiments of the present compounds also can exhibit excellent thermal stability over a wide range of annealing temperatures. Photovoltaic devices can maintain satisfactory power conversion efficiencies over an extended period of time.

As used herein, a compound can be considered soluble in a solvent when at least 0.1 mg of the compound can be dissolved in 1 mL of the solvent. Examples of common organic solvents include petroleum ethers; acetonitrile; aromatic hydrocarbons such as benzene, toluene, xylene, and mesitylene; ketones such as acetone, and methyl ethyl ketone; ethers such as tetrahydrofuran, dioxane, bis(2-methoxyethyl) ether, diethyl ether, di-isopropyl ether, and t-butyl methyl ether; alcohols such as methanol, ethanol, butanol, and isopropyl alcohol; aliphatic hydrocarbons such as hexanes; esters such as methyl acetate, ethyl acetate, methyl formate, ethyl formate, isopropyl acetate, and butyl acetate; amides such as dimethylformamide and dimethylacetamide; sulfoxides such as dimethylsulfoxide; halogenated aliphatic and aromatic hydrocarbons such as dichloromethane, chloroform, ethylene chloride, chlorobenzene, dichlorobenzene, and trichlorobenzene; and cyclic solvents such as cyclopentanone, cyclohexanone, and 2-methypyrrolidone. The present compounds can have room temperature solubilities in conventional organic solvents such as xylene, dichlorobenzene (DCB), and other chlorinated hydrocarbons (CHCs) as high as 60 g/L.

The present compounds can be fabricated into various articles of manufacture using solution processing techniques in addition to other more expensive processes such as vapor deposition. Various solution processing techniques have been used with organic electronics. Common solution processing techniques include, for example, spin coating, drop-casting, zone casting, dip coating, blade coating, or spraying. Another example of solution processing technique is printing. As used herein, "printing" includes a noncontact process such as inkjet printing, microdispensing and the like, and a contact process such as screen-printing, gravure printing, offset printing, flexographic printing, lithographic printing, pad printing, microcontact printing and the like.

Compounds of the present teachings can be used to prepare semiconductor materials (e.g., compositions and composites), which in turn can be used to fabricate various articles of manufacture, structures, and devices. In some embodiments, semiconductor materials incorporating one or more compounds of the present teachings can exhibit n-type semiconductor activity, ambipolar activity, light absorption, and light emission.

The present teachings, therefore, further provide methods of preparing a semiconductor material. The methods can include preparing a composition that includes one or more compounds disclosed herein dissolved or dispersed in a liquid medium such as a solvent or a mixture of solvents, depositing the composition on a substrate to provide a semiconductor material precursor, and processing (e.g., heating) the semiconductor precursor to provide a semiconductor material (e.g., a thin film semiconductor) that includes a compound disclosed herein. In various embodiments, the liquid medium can be an organic solvent, an inorganic solvent such as water, or combinations thereof. In some embodiments, the composition can further include one or more additives independently selected from viscosity modulators, detergents, dispersants, binding agents, compatibilizing agents, curing agents, initiators, humectants, antifoaming agents, wetting agents, pH modifiers, biocides, and bacteriostats. For example, surfactants and/or polymers (e.g., polystyrene, polyethylene, poly-alpha-methylstyrene, polyisobutene, polypropylene, polymethylmethacrylate, and the like) can be included as a dispersant, a binding agent, a compatibilizing agent, and/or an antifoaming agent. In some embodiments, the depositing step can be carried out by printing, including inkjet printing and various contact printing techniques (e.g., screen-printing, gravure printing, offset printing, pad printing, lithographic printing, flexographic printing, and microcontact printing). In other embodiments, the depositing step can be carried out by spin coating, drop-casting, zone casting, dip coating, blade coating, or spraying.

Various articles of manufacture including electronic devices, optical devices, and optoelectronic devices, such as thin film semiconductors, field effect transistors (e.g., thin film transistors), photovoltaics, photodetectors, organic light emitting devices such as organic light emitting diodes (OLEDs) and organic light emitting transistors (OLETs), complementary metal oxide semiconductors (CMOSs), complementary inverters, diodes, capacitors, sensors, D flip-flops, rectifiers, and ring oscillators, that make use of the compounds disclosed herein are within the scope of the present teachings as are methods of making the same. The present compounds can offer processing and operation advantages in the fabrication and/or the use of these devices. For example, articles of manufacture such as the various devices described herein can include a composite having a semiconductor material of the present teachings and a substrate component and/or a dielectric component. The substrate component can be selected from doped silicon, an indium tin oxide (ITO), ITO-coated glass, ITO-coated polyimide or other plastics, aluminum or other metals alone or coated on a polymer or other substrate, a doped polythiophene, and the like. The dielectric component can be prepared from inorganic dielectric materials such as various oxides (e.g., $SiO_2$, $Al_2O_3$, $HfO_2$), organic dielectric materials such as various polymeric materials (e.g., polycarbonate, polyester, polystyrene, polyhaloethylene, polyacrylate), and self-assembled superlattice/self-assembled nanodielectric (SAS/SAND) materials (e.g., described in Yoon, M-H. et al., PNAS, 102 (13): 4678-4682 (2005), the entire disclosure of which is incorporated by reference herein), as well as hybrid organic/inorganic dielectric materials (e.g., described in U.S. patent application Ser. No. 11/642,504, the entire disclosure of which is incorporated by reference herein). In some embodiments, the dielectric component can include the crosslinked polymer blends described in U.S. patent application Ser. Nos. 11/315,076, 60/816,952, and 60/861,308, the entire disclosure of each of which is incorporated by reference herein. The composite also can include one or more electrical contacts. Suitable materials for the source, drain, and gate electrodes include metals (e.g., Au, Al, Ni, Cu), transparent conducting oxides (e.g., ITO, IZO, ZITO, GZO, GIO, GITO), and conducting polymers (e.g., poly(3,4-ethylenedioxythiophene) poly(styrenesulfonate) (PEDOT:PSS), polyaniline (PANI), polypyrrole (PPy)). One or more of the composites described herein can be embodied within various organic electronic, optical, and optoelectronic devices such as organic thin film transistors (OTFTs), specifically, organic field effect transistors (OFETs), as well as sensors, capacitors, unipolar circuits, complementary circuits (e.g., inverter circuits), and the like.

Other articles of manufacture in which compounds of the present teachings are useful are photovoltaics or solar cells. Particularly, polymers of the present teachings can exhibit broad optical absorption and/or a tuned redox properties and bulk carrier mobilities, making them desirable for such applications. For example, the polymers described herein can be used as a donor (p-type) semiconductor in a photovoltaic design, which includes an adjacent n-type semiconductor material that forms a p-n junction. The polymers can be in the form of a thin film semiconductor, which can be deposited on a substrate to form a composite. Exploitation of polymers of the present teachings in such devices is within the knowledge of a skilled artisan.

Accordingly, another aspect of the present teachings relates to methods of fabricating an organic field effect transistor that incorporates a semiconductor material of the present teachings. The semiconductor materials of the present teachings can be used to fabricate various types of organic field effect transistors including top-gate top-contact capacitor structures, top-gate bottom-contact capacitor structures, bottom-gate top-contact capacitor structures, and bottom-gate bottom-contact capacitor structures. FIGS. 1a, 1b, 1c and 1d illustrate the four common types of OFET structures: FIG. 1a shows bottom-gate top-contact structure, FIG. 1b shows bottom-gate bottom-contact structure, FIG. 1c shows top-gate bottom-contact structure, and FIG. 1d shows top-gate top-contact structure. As shown in FIGS. 1a, 1b, 1c and 1d, an OFET can include a dielectric layer (e.g., shown as 8, 8', 8", and 8''' in FIGS. 1a, 1b, 1c, and 1d, respectively), a semiconductor/channel layer (e.g., shown as 6, 6', 6", and 6''' in FIGS. 1a, 1b, 1c, and 1d, respectively), a gate contact (e.g., shown as 10, 10', 10", and 10''' in FIGS. 1a, 1b, 1c, and 1d, respectively), a substrate (e.g., shown as 12, 12', 12", and 12''' in FIGS. 1a, 1b, 1c, and 1d, respectively), and source and drain contacts (e.g., shown as 2, 2', 2", 2''', 4, 4', 4", and 4''' in FIGS. 1a, 1b, 1c, and 1d, respectively).

In certain embodiments, OTFT devices can be fabricated with the present semiconducting compounds on doped silicon substrates, using $SiO_2$ as the dielectric, in top-contact geometries. In particular embodiments, the active semiconductor layer which incorporates at least a semiconducting compound of the present teachings can be deposited at room temperature or at an elevated temperature. In other embodiments, the active semiconductor layer which incorporates at least one semiconducting compound of the present teachings can be applied by spin-coating or printing as described herein. For top-contact devices, metallic contacts can be patterned on top of the films using shadow masks.

In certain embodiments, OTFT devices can be fabricated with the present compounds on plastic foils, using polymers as the dielectric, in top-gate bottom-contact geometries. In particular embodiments, the active semiconducting layer which incorporates at least a semiconducting compound of the present teachings can be deposited at room temperature or at an elevated temperature. In other embodiments, the active semiconducting layer which incorporates at least a semiconducting compound of the present teachings can be applied by spin-coating or printing as described herein. Gate and source/drain contacts can be made of Au, other metals, or conducting polymers and deposited by vapor-deposition and/or printing.

Figure 3:
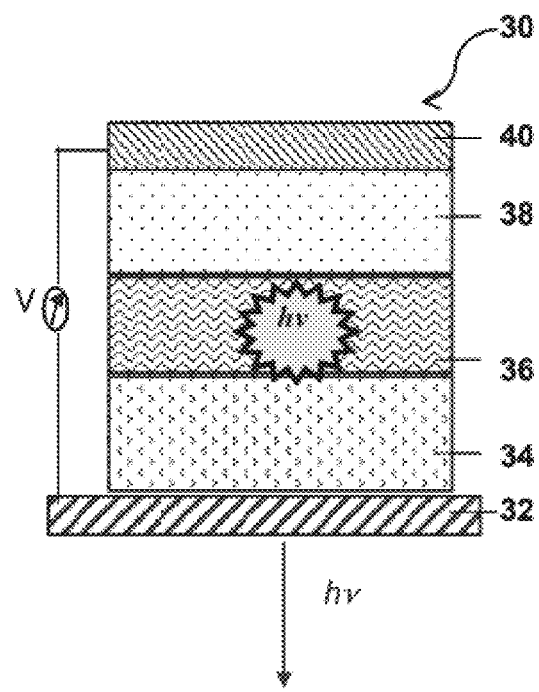
FIG. 3 illustrates a representative structure of an organic light-emitting device which can incorporate one or more compounds of the present teachings as electron-transporting and/or emissive and/or hole-transporting materials.

Similarly, another aspect of the present teachings relates to methods of fabricating an organic light-emitting transistor, an organic light-emitting diode (OLED), or an organic photovoltaic device that incorporates one or more semiconductor materials of the present teachings. FIG. 2 illustrates a representative structure of a bulk-heterojunction organic photovoltaic device (also known as solar cell) which can incorporate one or more semiconducting compounds of the present teachings as the donor material. As shown, a representative solar cell generally includes a substrate 20 (e.g., glass), an anode 22 (e.g., ITO), a cathode 26 (e.g., aluminium or calcium), and an active layer 24 between the anode and the cathode which can incorporate one or more semiconducting compounds of the present teachings as the electron donor (p-channel) materials. FIG. 3 illustrates a representative structure of an OLED which can incorporate one or more semiconducting compounds of the present teachings as electron-transporting and/or emissive and/or hole-transporting materials. As shown, an OLED generally includes a substrate 30 (not shown), a transparent anode 32 (e.g., ITO), a cathode 40 (e.g., metal), and one or more organic layers which can incorporate one or more semiconducting compounds of the present teachings as hole-transporting (n-channel) (layer 34 as shown) and/or emissive (layer 36 as shown) and/or electron-transporting (p-channel) materials (layer 38 as shown).

Molecular orbital (MO) calculations (B3LYP/6-31G*) (Spartan'08 Wavefunction, Inc. Irvine, Calif.) were carried out to study the frontier molecular orbital energy and the molecular orbital topology of the dithiophenethiadiazole units disclosed herein. The results are summarized in Table 1 below.

TABLE 1

Chemical Structure, Frontier Molecular Orbital Energy, and Molecular Orbital Topology for the Indicated Thiadiazole Units.

| Structure | $E_{HOMO}$ (eV) | $E_{LUMO}$ (eV) |
|---|---|---|
| (structure 1) | −5.64 | −2.64 |
| (structure 2) | −5.22 | −2.63 |

All publications, including but not limited to patents and patent applications, cited in this specification are herein incorporated by reference as if each individual publication were specifically and individually indicated to be incorporated by reference herein as though fully set forth.

The present teachings encompass embodiments in other specific forms without departing from the spirit or essential characteristics thereof. The foregoing embodiments are therefore to be considered in all respects illustrative rather than limiting on the present teachings described herein. Scope of the present invention is thus indicated by the appended claims rather than by the foregoing description, and all changes that come within the meaning and range of equivalency of the claims are intended to be embraced therein.

What is claimed is:

1. A semiconducting compound comprising one or more moieties represented by formula (I):

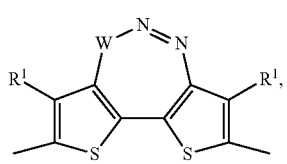

(I)

wherein:

W is selected from the group consisting of S, Se, and Te; and each $R^1$ independently is selected from the group consisting of H, halogen, —CN, $NO_2$, $R^2$, -L-$R^3$, OH, $OR^2$, $OR^3$, $NH_2$, $NHR^2$, $N(R^2)_2$, $NR^2R^3$, $N(R^3)_2$, SH, $SR^2$, $SR^3$, $S(O)_2OH$, —$S(O)_2OR^2$, —$S(O)_2OR^3$, C(O)H, C(O)$R^2$, C(O)$R^3$, C(O)OH, C(O)O$R^2$, C(O)O$R^3$, C(O)$NH_2$, C(O)$NHR^2$, C(O)N$(R^2)_2$, C(O)N$R^2R^3$, C(O)N$(R^3)_2$, $SiH_3$, $SiH(R^2)_2$, $SiH_2(R^2)$, and $Si(R^2)_3$, wherein L is selected from the group consisting of a divalent $C_{1-40}$ alkyl group, a divalent $C_{2-40}$ alkenyl group, a divalent $C_{1-40}$ haloalkyl group, and a covalent bond; each $R^2$ independently is selected from the group consisting of a $C_{1-40}$ alkyl group, a $C_{2-40}$ alkenyl group, a $C_{2-40}$ alkynyl group, and a $C_{1-40}$ haloalkyl group; and each $R^3$ independently is selected from the group consisting of a $C_{3-10}$ cycloalkyl group, a $C_{6-14}$ aryl group, a $C_{6-14}$ haloaryl group, a 3-12 membered cycloheteroalkyl group, and a 5-14 membered heteroaryl group, each of which optionally is substituted with 1-5 substituents independently selected from the group consisting of halogen, —CN, $NO_2$, $R^2$, $OR^2$, and $SR^2$.

2. The compound of claim 1, wherein the one or more moieties represented by formula (I) are optionally substituted dithieno[1,2,3]thiadiazole moieties represented by formula (II):

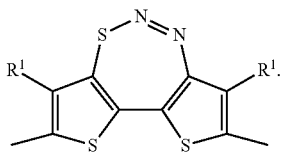

(II)

3. The compound of claim 2, wherein $R^1$ is selected from the group consisting of F, Cl, —CN, —NO$_2$, $R^2$, $OR^2$, and $SR^2$, wherein $R^2$ is selected from the group consisting of a linear or branched $C_{1-40}$ alkyl group, a linear or branched $C_{2-40}$ alkenyl group, and a linear or branched $C_{1-40}$ haloalkyl group.

4. The compound of claim 2, wherein $R^1$ is H and the one or more moieties represented by formula (I) are unsubstituted dithieno[1,2,3]thiadiazole moieties represented by formula (III):

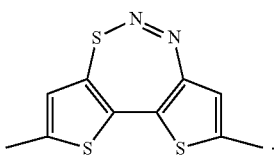

(III)

5. The compound of claim 1, wherein the compound is a polymer having a first repeating unit $M_1$ comprising one or more divalent units represented by formula (I) and wherein said polymer has a degree of polymerization (n) ranging from 3 to 1,000.

6. The compound of claim 5, wherein $M_1$ is selected from the group consisting of:

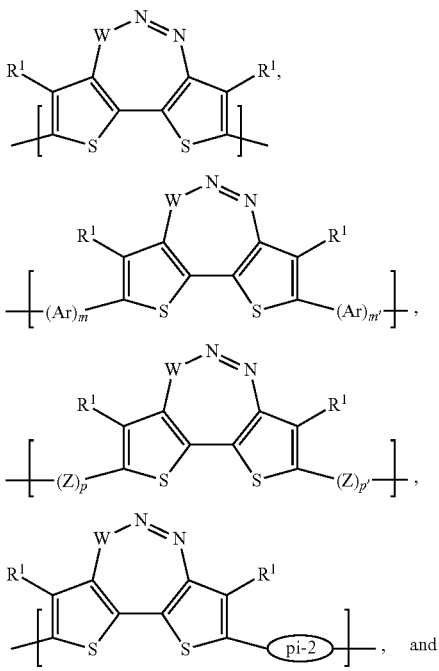

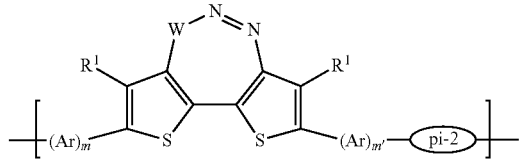

wherein:

pi-2 is an optionally substituted conjugated polycyclic moiety;

Ar, at each occurrence, is independently an optionally substituted 5- or 6-membered aryl or heteroaryl group;

Z is a conjugated noncyclic linker;

m and m' independently are 0, 1, 2, 3, 4, 5 or 6, provided that at least one of m and m' is not 0; and p and p' independently are 0 and 1, provided that at least one of p and p' is 1.

7. The compound of claim 6, wherein W is S.

8. The compound of claim 6, wherein pi-2 is an optionally substituted $C_{8-26}$ aryl group or 8-26 membered heteroaryl group.

9. The compound of claim 8, wherein pi-2 is selected from the group consisting of:

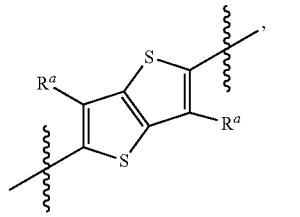

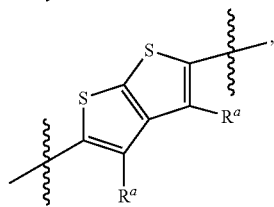

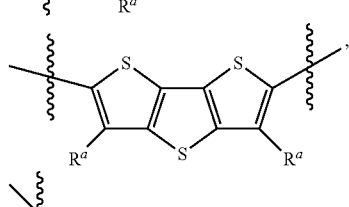

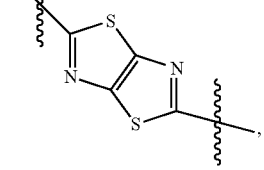

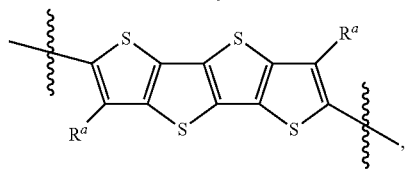

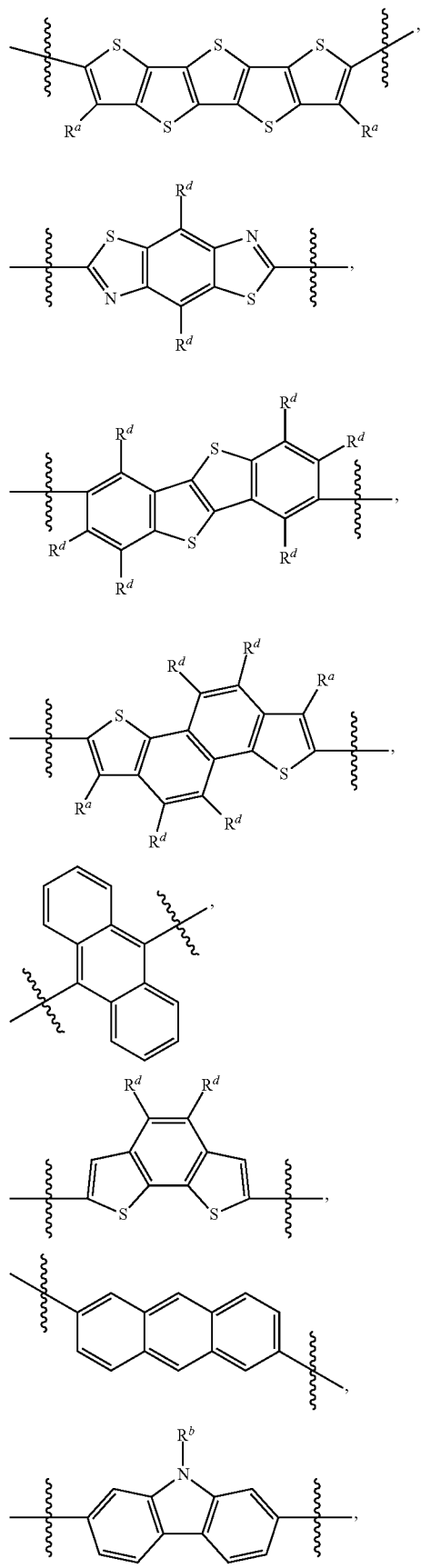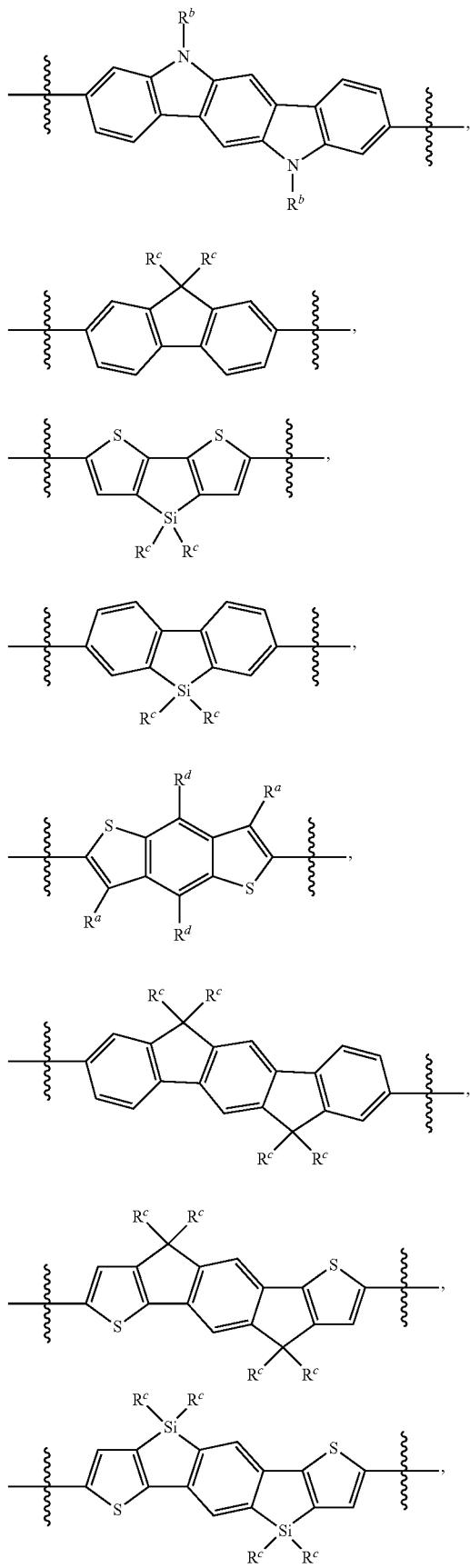

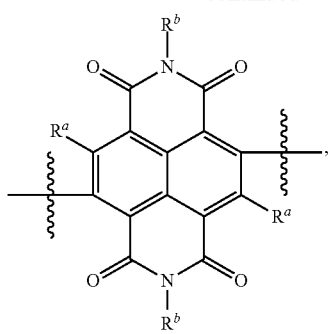
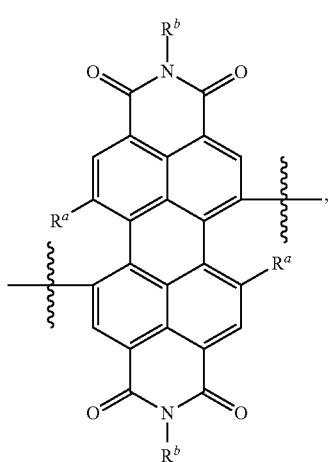
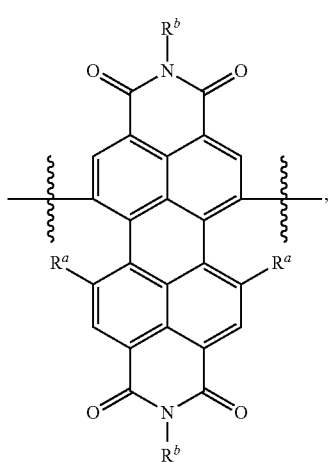
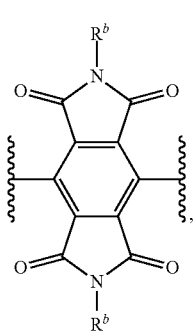
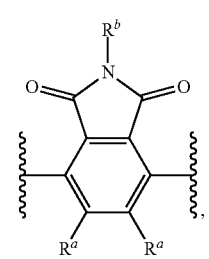
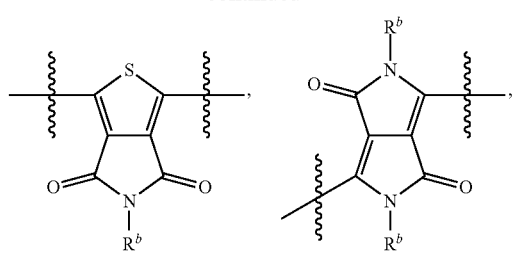
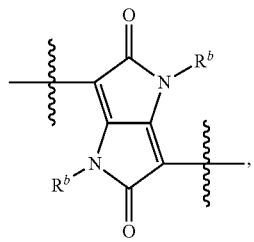
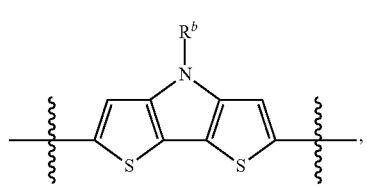
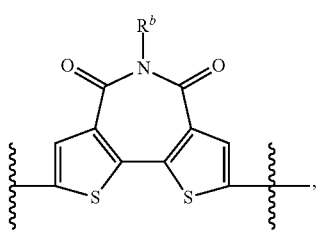
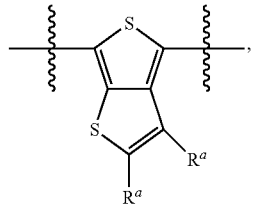
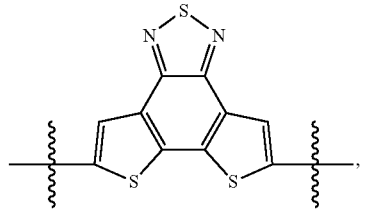
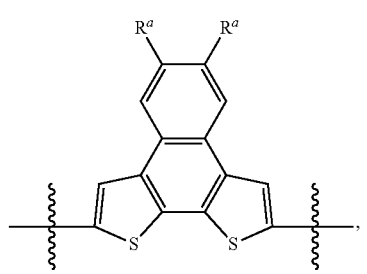

-continued

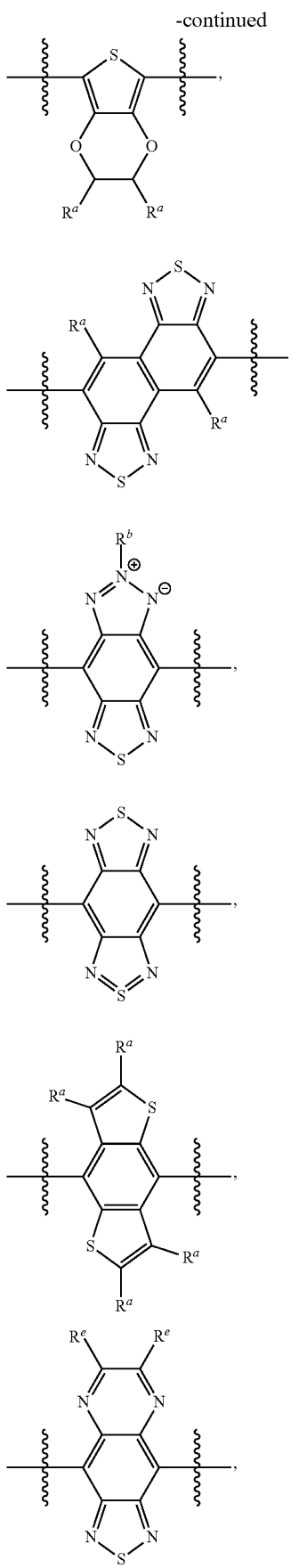

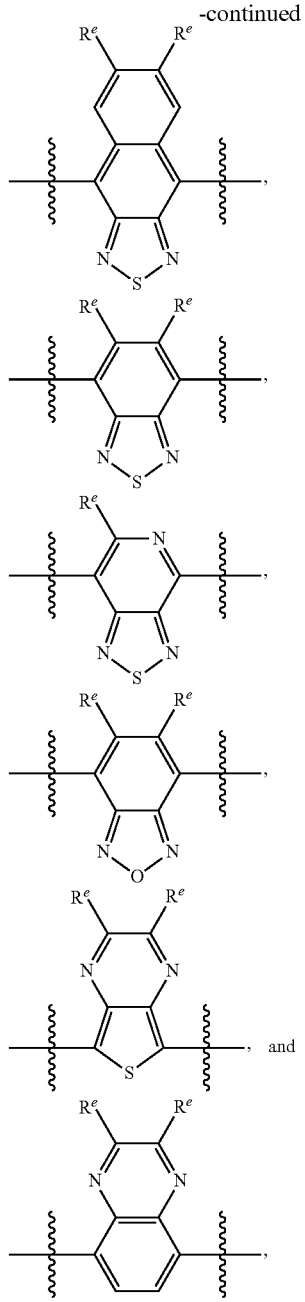

wherein:
$R^a$ is selected from the group consisting of H, F, Cl, —CN, R, —OR, —SR, —C(O)R, —OC(O)R, and —C(O)OR;
$R^b$ is selected from the group consisting of H, R, and -L-$R^f$;
$R^c$ is H or R;
$R^d$ is selected from the group consisting of H, F, Cl, —CN, R, —OR, —SR, —C(O)R, —OC(O)R, —C(O)OR, and -L-$R^f$;
$R^e$ is selected from the group consisting of H, F, Cl, —CN, R, —OR, —SR, —C(O)R, —OC(O)R, —C(O)OR, and $R^f$;
$R^f$ is a $C_{6-20}$ aryl group or a 5-20-membered heteroaryl group, each optionally substituted with 1-8 groups independently selected from the group consisting of F, Cl, —CN, R, —OR, and —SR;

L is selected from the group consisting of —O—, —S—, —C(O)—, —OC(O)—, —C(O)O—, and a covalent bond; and R is selected from the group consisting of a $C_{1-40}$ alkyl group, a $C_{1-40}$ haloalkyl group, a $C_{2-40}$ alkenyl group, and a $C_{2-40}$ alkynyl group.

10. The compound of claim 6, wherein Ar in $(Ar)_m$ and $(Ar)^{m'}$ is represented by:

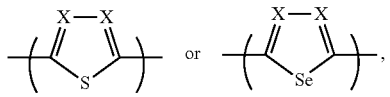

wherein each X independently is selected from the group consisting of N, CH, and $CR^4$, wherein $R^4$ is selected from the group consisting of F, Cl, —CN, $R^2$, $OR^2$, $SR^2$, $C(O)R^2$, $OC(O)R^2$, and $C(O)OR^2$, and wherein $R^2$ is selected from the group consisting of a $C_{1-40}$ alkyl group, a $C_{2-40}$ alkenyl group, a $C_{2-40}$ alkynyl group, and a $C_{1-40}$ haloalkyl group.

11. The compound of claim 10, wherein $(Ar)_m$ and $(Ar)^{m'}$ independently are selected from the group consisting of:

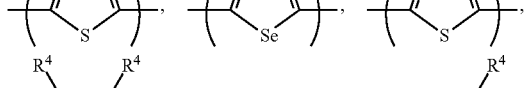
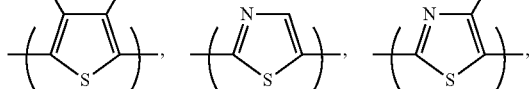
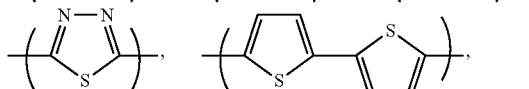
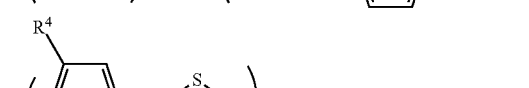
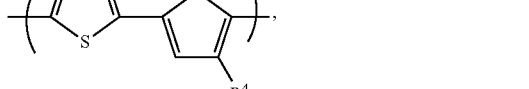
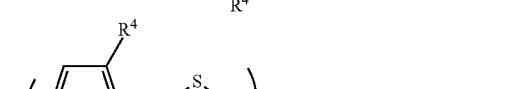

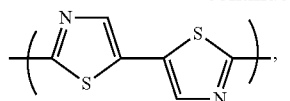
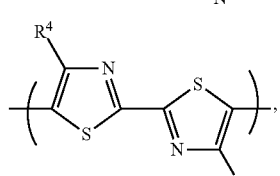
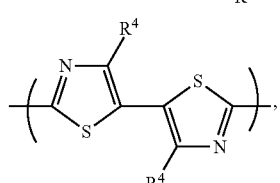
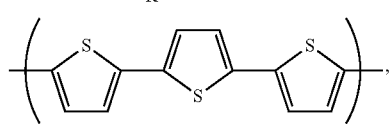
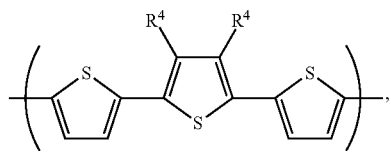
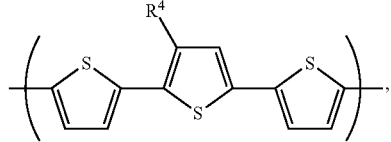
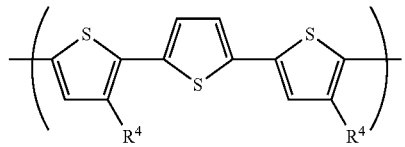
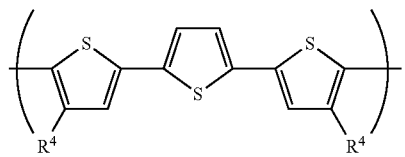
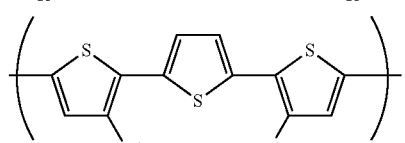
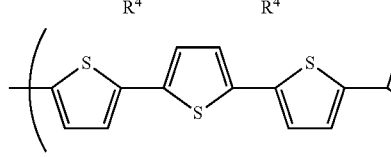
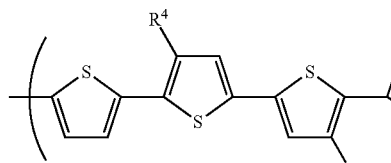

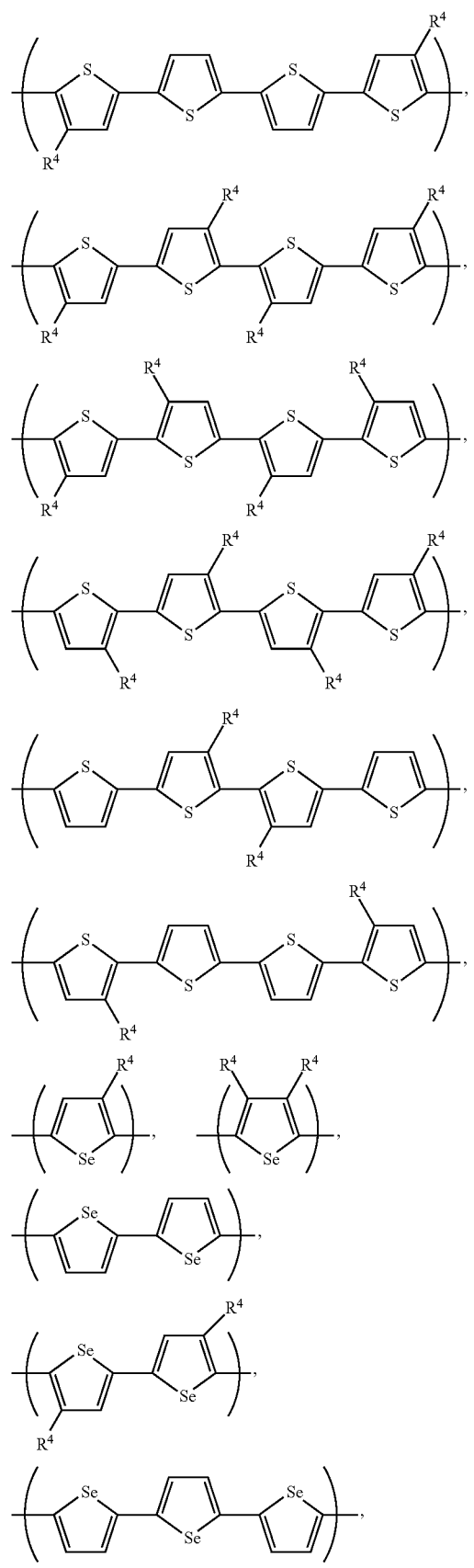
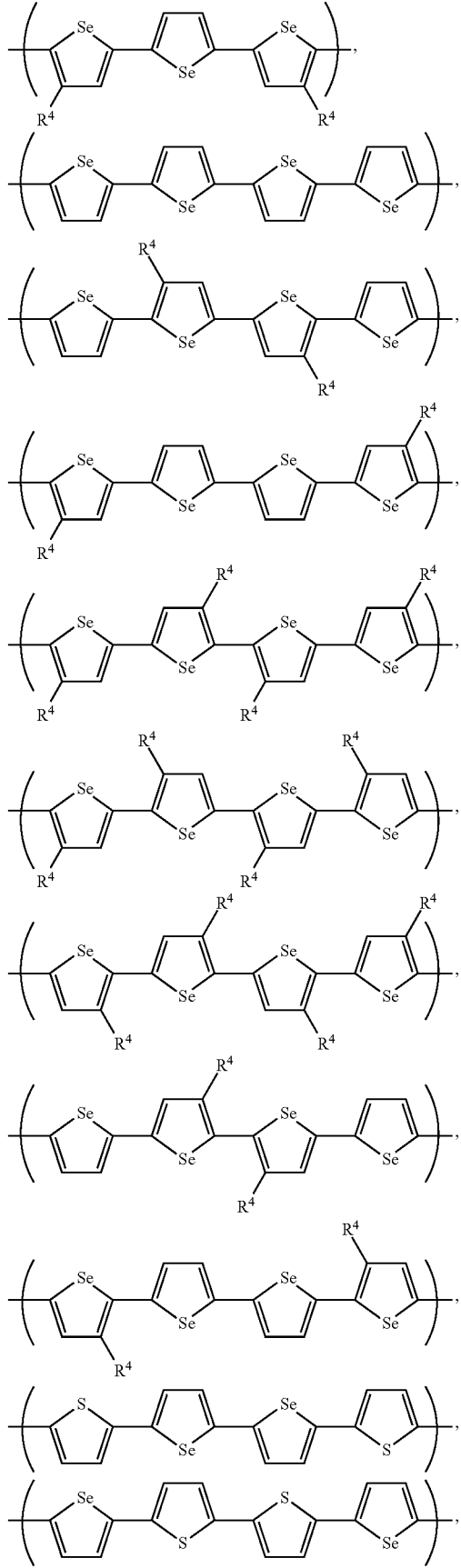

-continued

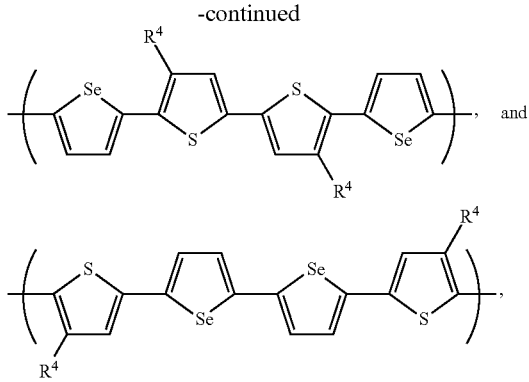
and

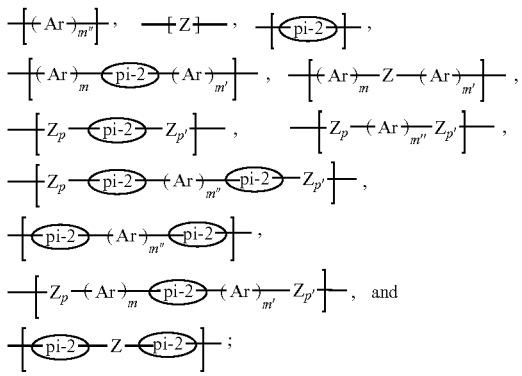

wherein R⁴, at each occurrence, independently is selected from the group consisting of F, Cl, CN, R², OR², and SR², where R² is a linear or branched $C_{1-40}$ alkyl or haloalkyl group.

12. The compound of claim 6, wherein Z is selected from the group consisting of:

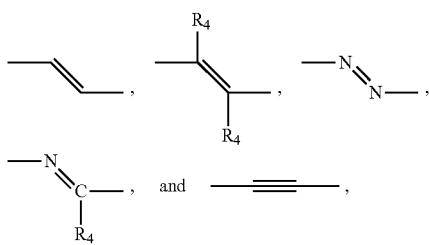

wherein R⁴ is selected from the group consisting of F, Cl, —CN, R², OR², SR², C(O)R², OC(O)R², and C(O)OR², and wherein R² is selected from the group consisting of a $C_{1-40}$ alkyl group, a $C_{2-40}$ alkenyl group, a $C_{2-40}$ alkynyl group, and a $C_{1-40}$ haloalkyl group.

13. The compound of any one of claim 6, further comprising one or more repeating units other than $M_1$, the one or more other repeating units ($M_2$) being selected from the group consisting of:

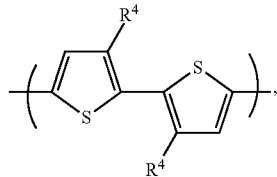
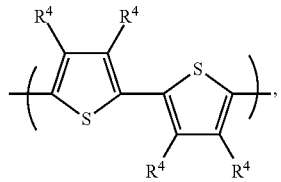
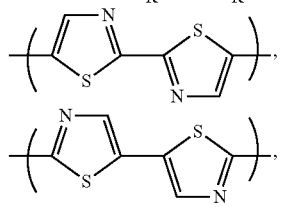

wherein:
pi-2 is an optionally substituted conjugated polycyclic moiety;
Ar, at each occurrence, is independently an optionally substituted 5- or 6-membered aryl or heteroaryl group;
Z is a conjugated noncyclic linker;

m and m' independently are 0, 1, 2, 3, 4, 5 or 6, provided that at least one of m and m' is not 0;
m" is 1, 2, 3, 4, 5 or 6; and
p and p' independently are 0 and 1, provided that at least one of p and p' is 1.

14. The compound of claim 13, wherein in the one or more $M_2$ repeating units, Z is selected from the group consisting of:

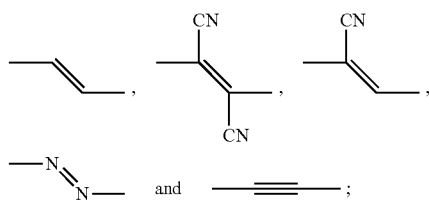

$(Ar)_m$, $(Ar)_{m'}$, and $(Ar)_{m''}$ independently are selected from the group consisting of:

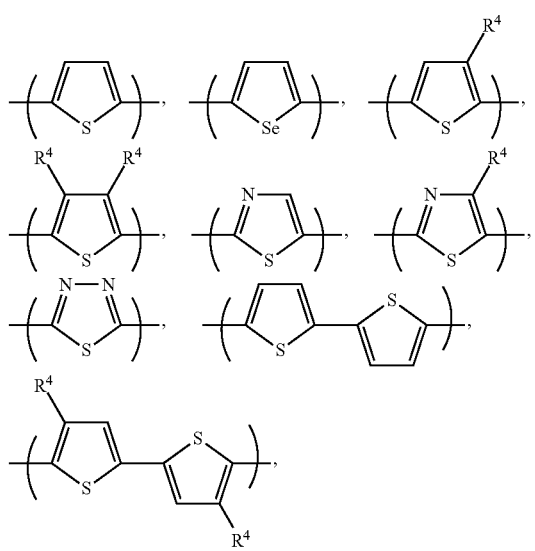

-continued
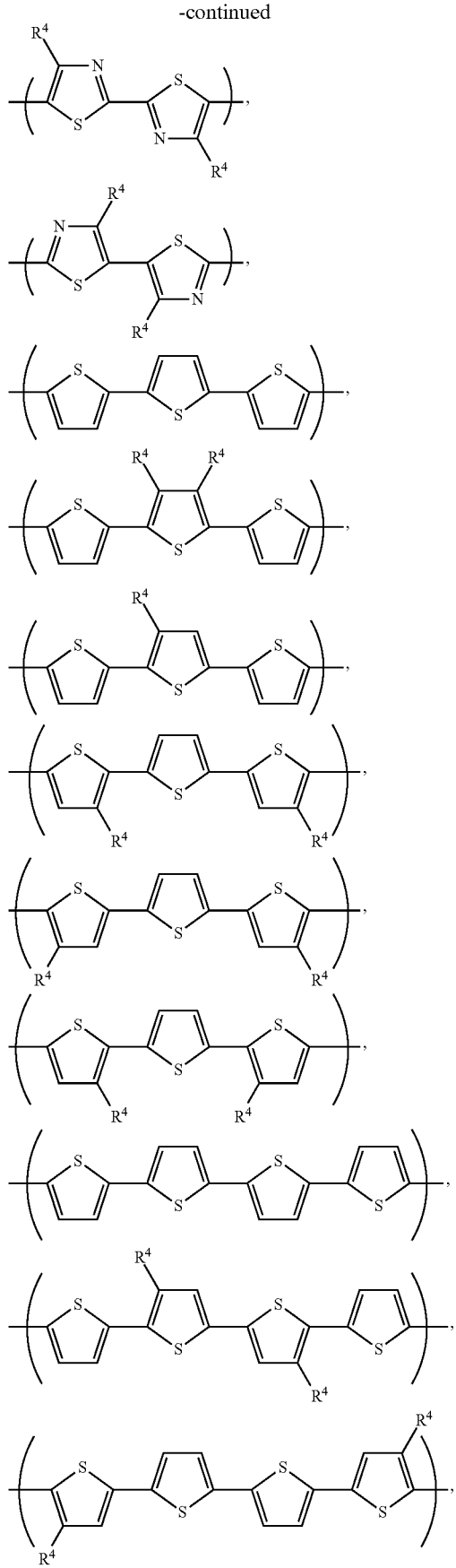
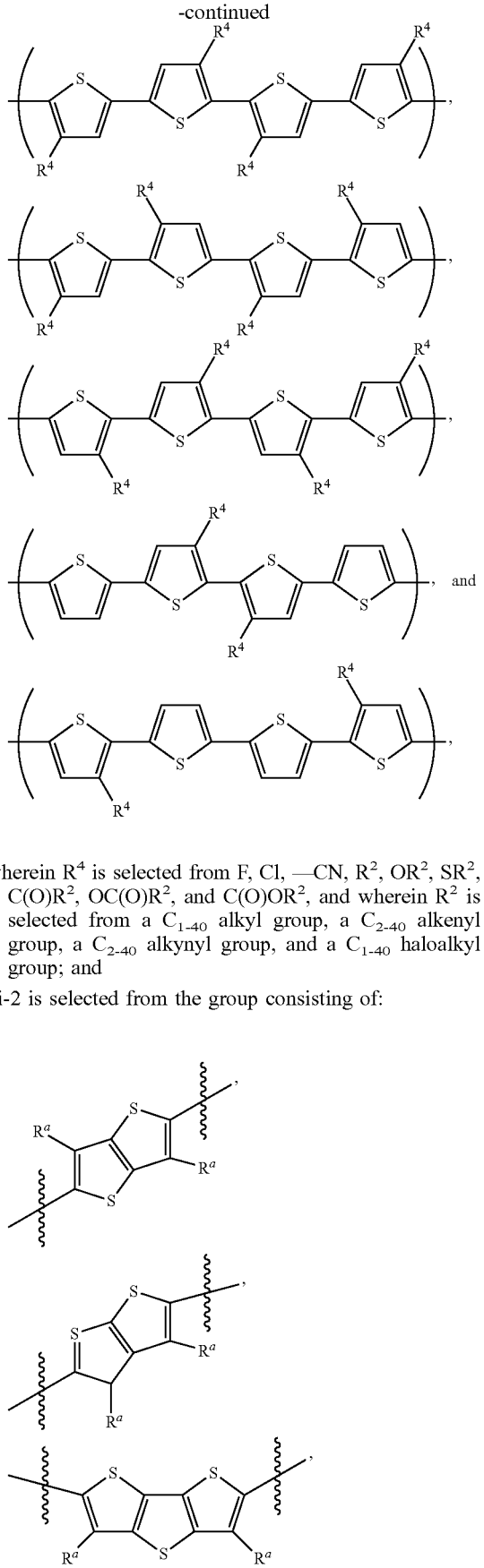
wherein $R^4$ is selected from F, Cl, —CN, $R^2$, $OR^2$, $SR^2$, $C(O)R^2$, $OC(O)R^2$, and $C(O)OR^2$, and wherein $R^2$ is selected from a $C_{1-40}$ alkyl group, a $C_{2-40}$ alkenyl group, a $C_{2-40}$ alkynyl group, and a $C_{1-40}$ haloalkyl group; and
pi-2 is selected from the group consisting of:
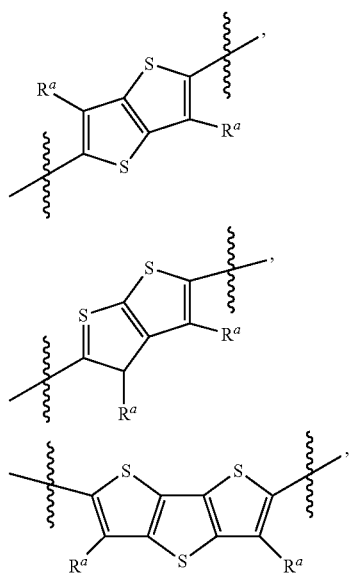

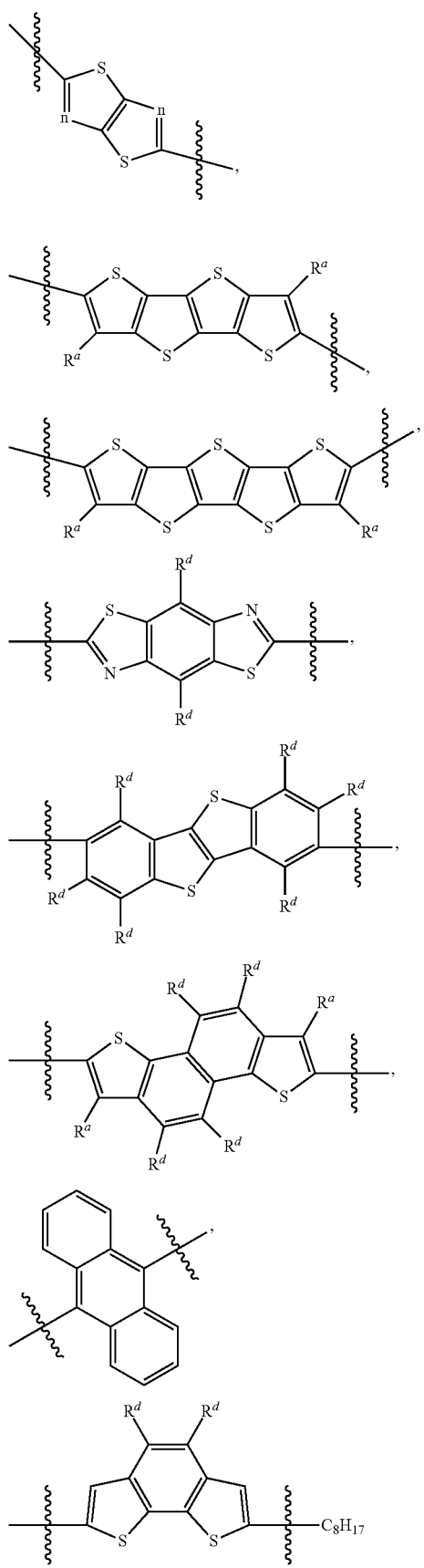
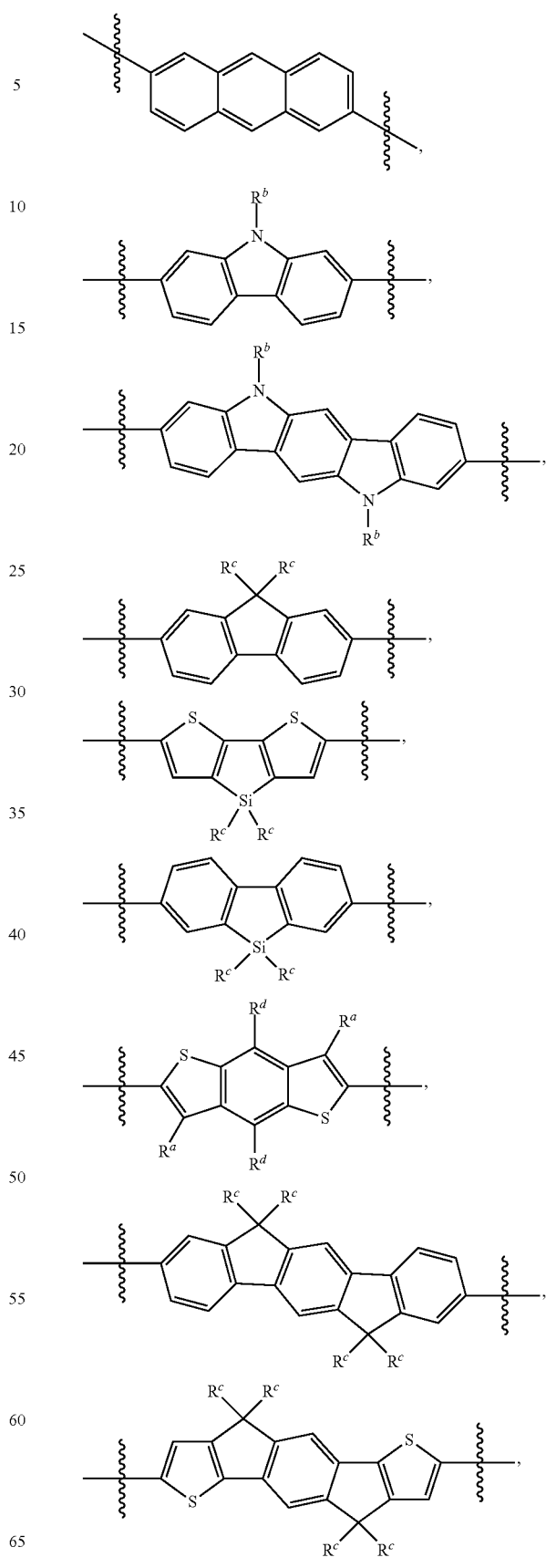

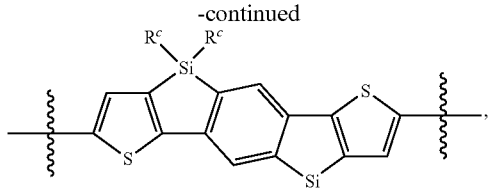
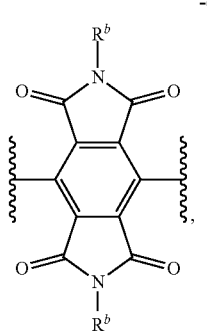
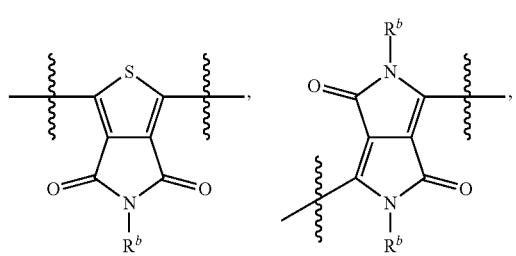
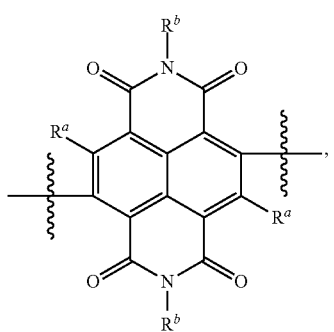
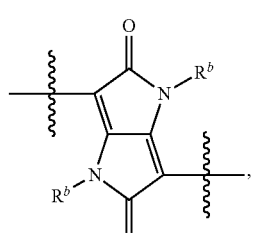
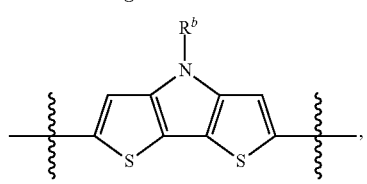
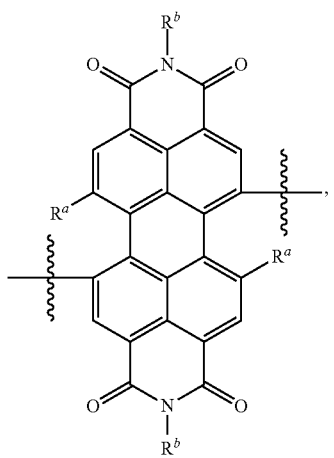
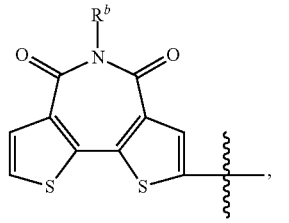
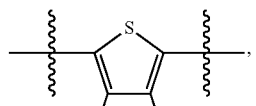
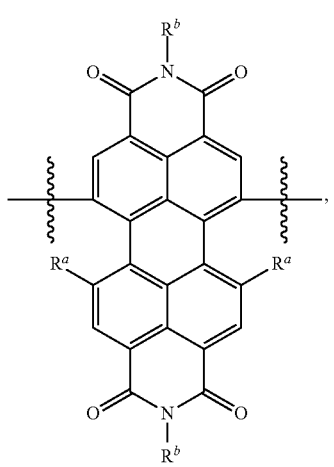
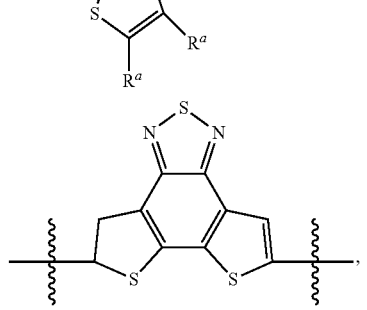

-continued
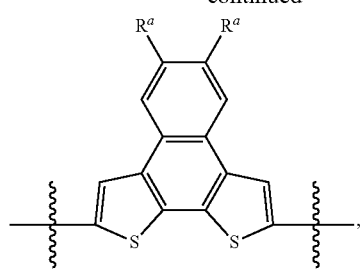
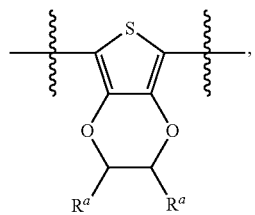
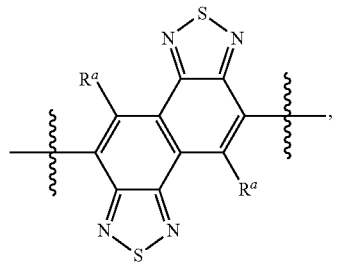
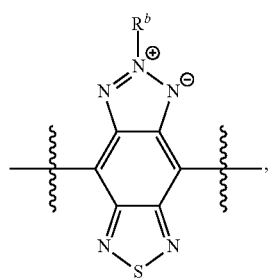
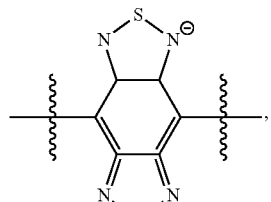
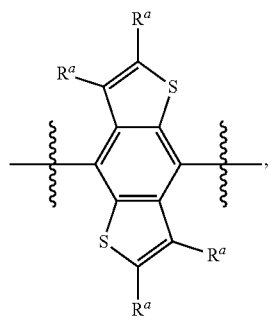
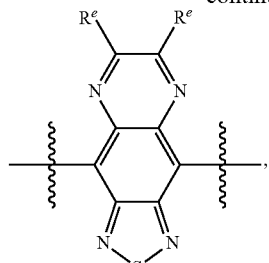
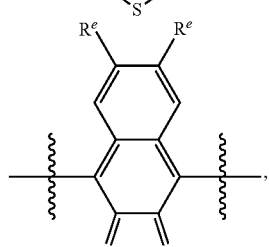
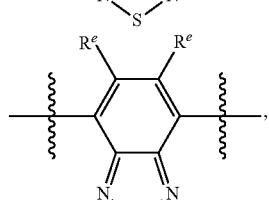
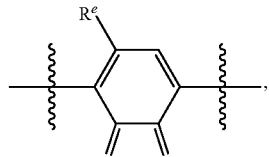
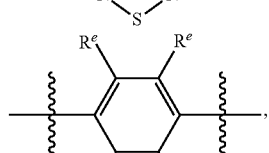
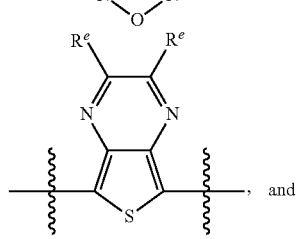
, and
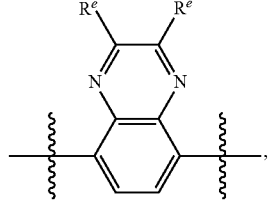
;
wherein:
$R^a$ is selected from the group consisting of H, F, Cl, —CN, R, —OR, —SR, —C(O)R, —OC(O)R, and —C(O)OR;
$R^b$ is selected from the group consisting of H, R, and -L-$R^f$;

$R^c$ is H or R;

$R^d$ is selected from the group consisting of H, F, Cl, —CN, R, —OR, —SR, —C(O)R, —OC(O)R, —C(O)OR, and -L-$R^f$; and $R^e$ is selected from the group consisting of H, F, Cl, —CN, R, —OR, —SR, —C(O)R, —OC(O)R, —C(O)OR, and $R^f$; wherein $R^f$ is a $C_{6-20}$ aryl group or a 5-20-membered heteroaryl group, each optionally substituted with 1-8 groups independently selected from the group consisting of F, Cl, —CN, R, —OR, and —SR;

L is selected from the group consisting of —O—, —S—, —C(O)—, —OC(O)—, —C(O)O—, and a covalent bond; and R is selected from the group consisting of a $C_{1-40}$ alkyl group, a $C_{1-40}$ haloalkyl group, a $C_{2-40}$ alkenyl group, and a $C_{2-40}$ alkynyl group; and R is selected from the group consisting of a $C_{1-40}$ alkyl group, a $C_{1-40}$ haloalkyl group, a $C_{2-40}$ alkenyl group, and a $C_{2-40}$ alkynyl group.

15. The compound of claim 14, wherein $M_1$ is selected from the group consisting of:

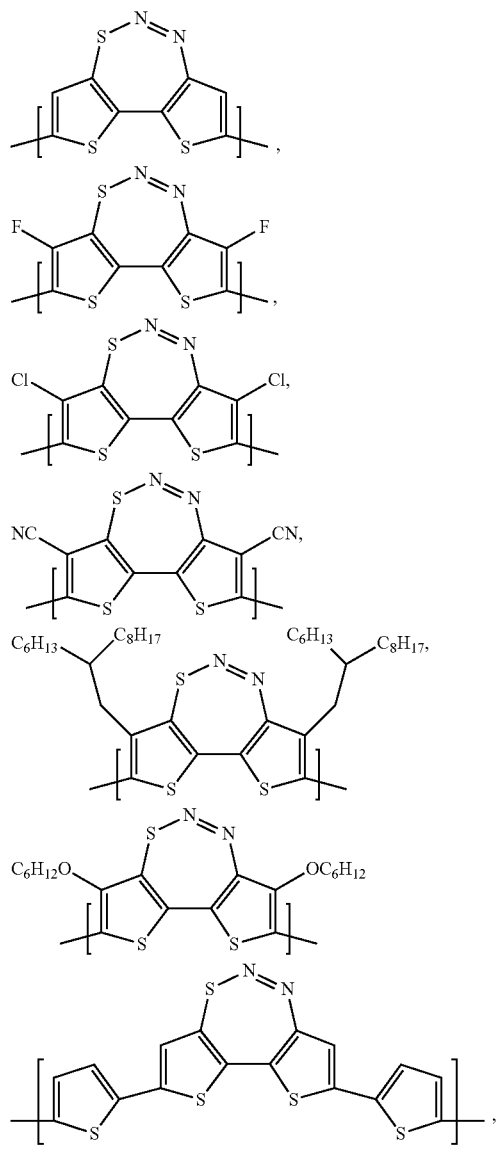

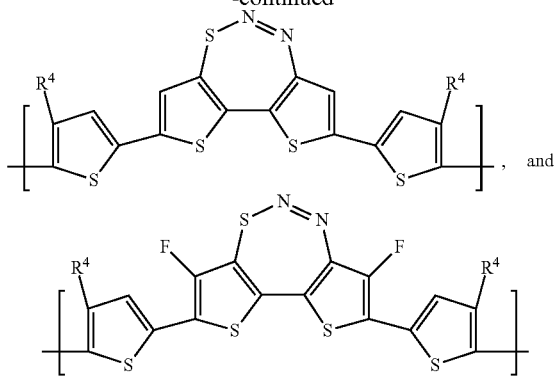

wherein $R^4$ is selected from the group consisting of $R^2$, $OR^2$, and $SR^2$, where $R^2$ is a linear or branched $C_{1-40}$ alkyl or haloalkyl group; and $M_2$ is selected from the group consisting of:

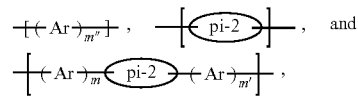

wherein $(Ar)_m$, $(Ar)_{m'}$, and $(Ar)_{m''}$ independently are selected from the group consisting of:

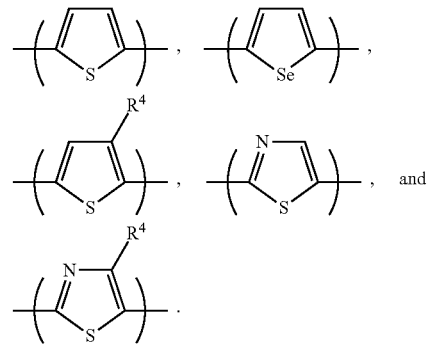

16. The compound of claim 13, wherein the compound is a copolymer having a formula selected from the group consisting of:

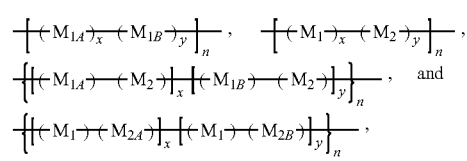

wherein $M_{1A}$ and $M_{1B}$ represent different repeating units $M_1$, and $M_{2A}$ and $M_{2B}$ represent different repeating units $M_2$, x and y are real numbers representing molar ratios, and n is the degree of polymerization.

17. The compound of claim 16, wherein the compound is a random copolymer.

18. The compound of any one of claim 1, wherein the compound is a small molecule represented by a formula selected from the group consisting of:

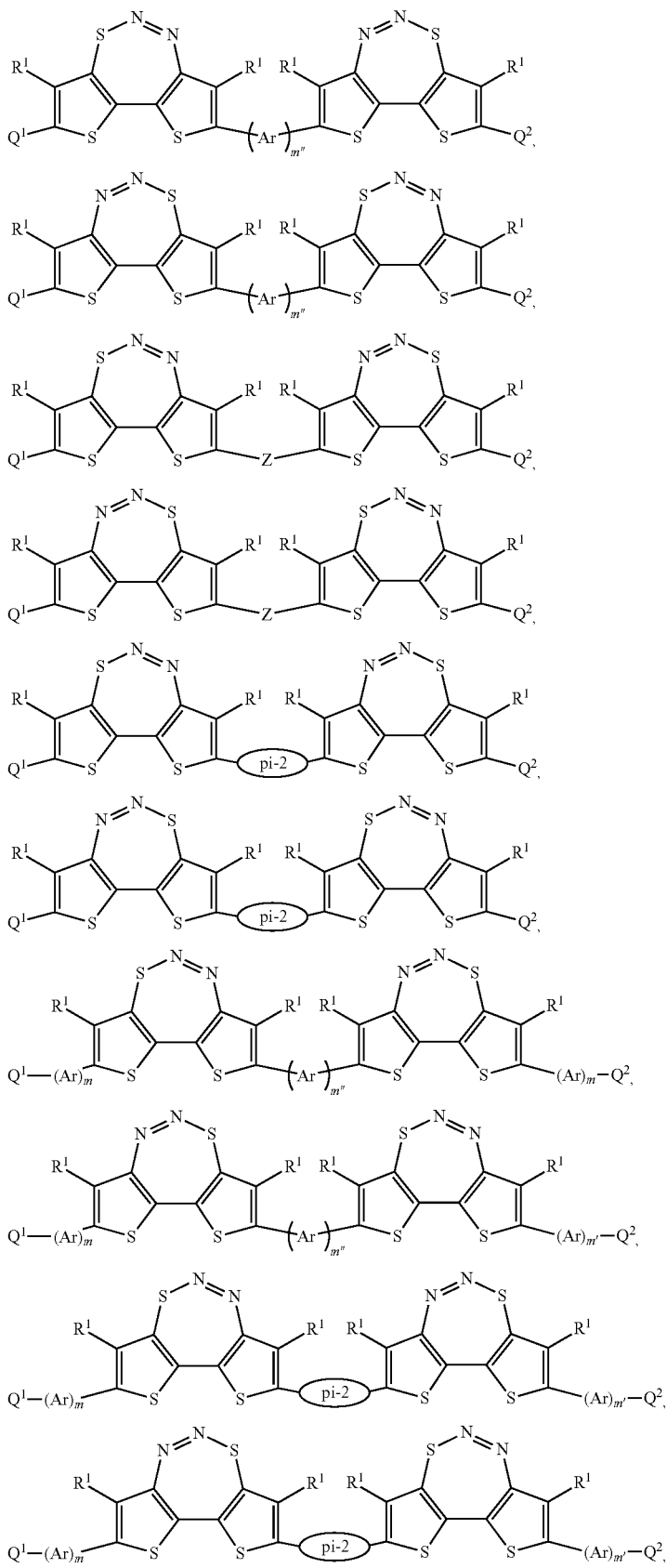

-continued

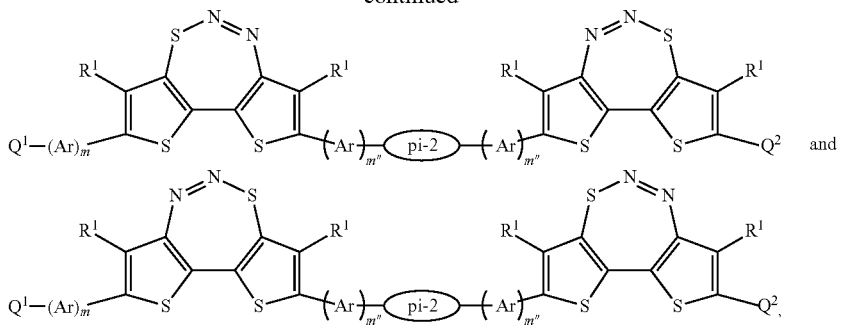

wherein:

$Q^1$ and $Q^2$ independently are selected from the group consisting of H, $R^2$, and $C(O)R^2$, wherein $R^2$ is a $C_{1-40}$ alkyl or haloalkyl group;

pi-2 is an optionally substituted conjugated polycyclic moiety;

Ar, at each occurrence, is independently an optionally substituted 5- or 6-membered aryl or heteroaryl group;

Z is a conjugated noncyclic linker;

m and m' independently are 0, 1, 2, 3, 4, 5 or 6, provided that at least one of m and m' is not 0;

m" is 1, 2, 3, 4, 5 or 6; and p and p' independently are 0 and 1, provided that at least one of p and p' is 1.

19. An electronic, optical or optoelectronic device comprising a semiconductor component, the semiconductor component comprising a compound of any one of claim 1.

20. An organic photovoltaic device comprising an anode, a cathode, optionally one or more anode interlayers, optionally one or more cathode interlayers, and in between the anode and the cathode a semiconductor component comprising a blend material, the blend material comprising an electron-acceptor compound and an electron-donor compound, the electron-donor compound being a compound of any one of claim 1.

21. The device of claim 20, wherein the electron-acceptor compound is a fullerene compound.

22. The device of claim 20, wherein the electron-acceptor compound is an electron-transporting polymer.

23. An organic thin film transistor comprising a substrate, a thin film semiconductor, a dielectric layer, a gate electrode, and source and drain electrodes, wherein the thin film semiconductor comprises a compound of any one of claim 1.

* * * * *